(12) United States Patent
Vergetis et al.

(10) Patent No.: US 11,948,667 B2
(45) Date of Patent: Apr. 2, 2024

(54) SYSTEM AND INTERFACES FOR PROCESSING AND INTERACTING WITH CLINICAL DATA

(71) Applicant: Intelligencia Inc., New York, NY (US)

(72) Inventors: Evangelos Vergetis, New York, NY (US); Dimitrios Skaltsas, New York, NY (US)

(73) Assignee: Intelligencia Inc., New York, NY (US)

( * ) Notice: Subject to any disclaimer, the term of this patent is extended or adjusted under 35 U.S.C. 154(b) by 111 days.

(21) Appl. No.: 16/793,565

(22) Filed: Feb. 18, 2020

(65) Prior Publication Data
US 2020/0321083 A1   Oct. 8, 2020

Related U.S. Application Data

(60) Provisional application No. 62/821,014, filed on Mar. 20, 2019.

(30) Foreign Application Priority Data

Feb. 18, 2019  (GR) .............................. 20190100084

(51) Int. Cl.
  G16H 10/20   (2018.01)
  G06N 20/00   (2019.01)
  G16H 50/70   (2018.01)

(52) U.S. Cl.
  CPC ............. G16H 10/20 (2018.01); G06N 20/00 (2019.01); G16H 50/70 (2018.01)

(58) Field of Classification Search
  CPC ........ G16H 10/20; G16H 50/70; G16H 50/20; G16H 70/40; G06N 20/00
  See application file for complete search history.

(56) References Cited

U.S. PATENT DOCUMENTS

2009/0132276 A1   5/2009  Petera
2009/0276287 A1 * 11/2009  Firouzbakht ....... G06Q 30/0202
                                                   705/7.31
(Continued)

FOREIGN PATENT DOCUMENTS

WO   WO-2017210502 A1 * 12/2017 ........... G06K 9/6218

OTHER PUBLICATIONS

International Search Report and Written Opinion dated May 20, 2020 in connection with International Application No. PCT/US2020/018583.

(Continued)

*Primary Examiner* — Michael Tomaszewski
*Assistant Examiner* — Shyam M Goswami
(74) *Attorney, Agent, or Firm* — Wolf, Greenfield & Sacks, P.C.

(57) ABSTRACT

A system is provided that is capable of processing clinical trial data from one or more sources, both structured and unstructured data, and integrate such data in a database for access by users. Further, such trial data is combined with other types of data to train an AI-based model, for the purpose of determining a probability of a particular trial outcome, among other insights. Further, the system can provide insights into optimizing this probability, for example by optimizing elements of the clinical trial design. Further, the system stores the acquired data from multiple sources and provides search, comparison, and reporting capability within a single interface.

15 Claims, 49 Drawing Sheets

(56) References Cited

U.S. PATENT DOCUMENTS

| | | |
|---|---|---|
| 2010/0228699 A1 | 9/2010 | Webber et al. |
| 2015/0286802 A1 | 10/2015 | Kansara |
| 2019/0311299 A1* | 10/2019 | Lindner .............. G06F 21/6209 |
| 2019/0370616 A1 | 12/2019 | Eser et al. |
| 2020/0042923 A1* | 2/2020 | Zhou ...................... G16H 10/20 |
| 2020/0105413 A1* | 4/2020 | Vladimirova .......... G16H 20/30 |
| 2020/0350081 A9 | 11/2020 | Hernandez et al. |

OTHER PUBLICATIONS

[No Author Listed], Machine Learning in pharma: drug discovery and clinical trials. Pharma IQ. Nov. 26, 2018; 4 pages. Retrieved on Apr. 19, 2020 from https://www.pharma-iq.com/clinical/articles/machine-learning-in-pharma-drug-discovery-and-clinical-trials.

Huang et al., New Era in Drug Interaction Evaluation: US Food and Drug Administration Update on Cyp Enzymes, Transporters, and the Guidance Process. The Journal of Clinical Pharmacology. Mar. 31, 2008: 9 pages. Retrieved on Apr. 19, 2020 from https://accpl.onlinelibrary.wiley.com/doi/10.1177/0091270007312153.

Wong, Estimation of clinical trial success rates and related parameters. Diss. Massachusetts Institute of Technology. Sep. 2017; 48 pages. Retrieved on Apr. 19, 2020 from https://dspace.mit.edu/bitstream/handle/1721.1/113964/1023498646-MIT.pdf?sequence=1.

PCT/US2020/018583, May 20, 2020, International Search Report and Written Opinion.

Extended European Search Report dated Oct. 7, 2022 for European Application No. EP 20760084.2.

* cited by examiner

FIG. 3A

Fidelio ⓘ  |  Machine Learning  |  ∴ intelligencia.AI

Probability of FDA approval estimated at:
Phase 2 start

Drug Name
Gazyva

Active ingredient
Obinutuzumab

Therapeutic Area
Oncology

Indication
Chronic Lymphacytic Leukemia

Sponsor
Genentech

Lead Indication
True

Mechanism of Action
B-lymphacyte antigen CD20 inhibitor

Functionalities:

■ Machine Learning →

✎ Analytics

◨ Simulation

---

Probability of FDA approval

Assessment for Gazyva

69%

Average historic likelihood of FDA approval for drugs at start of Phase 2 development

Prediction Strength

Sensitivity analysis of the Machine-Learning outcomes

Confidence level

VERY HIGH

| HIGH |

MEDIUM

LOW

FIG. 5

VIEW BY INDICATION
View of marketed drugs

| INDICATION | YEAR | 2014 | 2015 | 2016 | 2017 | 2018 |
|---|---|---|---|---|---|---|
| Lung | | □ ○ | ○ | □ □ | ○ | |
| Breast | | | □ □ □ | □ □ | | |
| Colorectal | | | | | | |
| Prostate | | | | | | |
| Melanoma | | | | | | |
| Renal cell carcinoma | | | | | | |
| Urothelial bladder cancer | | | | | | |
| Head and neck cancer | | | | | | |
| Merkel cell carcinoma | | | | | | |
| MSI-H or dMMR cancer | | | | | | |
| Hodgkins lymphoma | | | | | | |
| Gastric cancer | | | | | | |
| Hepatocellular carcinoma | | | | | | |
| Cervical cancer | | | | | | |
| PMBCL | | | | | | |
| Cutaneous squamous-cell carcinoma | | | | | | |
| Other | | | | | | |

○ Pembrolizumab  □ Nivolumab  △ Durvalumab  ⚬ Atezolizumab  ♦ Avelumab  ✷ Other

From FIG. 9A

FIG. 9B

FILTER

CATEGORY ☑
- ☑ T-cell immunomodulator
- ☑ Other immunomodulator
- ☑ Cell therapy
- ☑ Oncolytic virus
- ☑ CD3-targeted bispecified mAb
- ☑ Cancer vaccine

INDICATION ☐
- ☐ Big four indications
  - ☐ Lung
  - ☐ Breast
  - ☐ Colorectal
  - ☐ Prostate
- ☐ Other Solid
  - ☐ Melanoma
  - ☐ Renal cell carcinoma
  - ☐ Urothelial bladder cancer
  - ☐ Head and neck cancer
  - ☐ Merkel cell carcinoma
  - ☐ MSI-H or dMMR cancer
  - ☐ Gastric cancer
  - ☐ Hepatocellular carcinoma
  - ☐ Cervical cancer
  - ☐ PMBCL
  - ☐ Cutaneous squamous-cell carcinoma
  - ☐ Other solid
- ☐ Liquid
  - ☐ Leukemia
  - ☐ Lymphoma
  - ☐ Other solid
- ☐ Other
- ☐ Unspecified

SPONSOR ☐
- ☐ Industry
  - ☐ Top-30
  - ☐ Mid size
  - ☐ Other
- ☐ Non-industry

TARGET ☐
- ☐ PD-1
- ☐ CD19
- ☐ PD-L1
- ☐ HER2
- ☐ IDO1
- ☐ STAT3
- ☐ CTLA-4
- ☐ CD40
- ☐ CSFR1
- ☐ Other
- ☐ Unspecified

[+ FULL LIST]

PHASE ☐
- ☐ Pre-clinical
- ☐ Phase 1
- ☐ Phase 1/2
- ☐ Phase 2
- ☐ Phase 3
- ☐ Phase 4

TRIAL TYPE ☐
- ☐ Combination Therapy
- ☐ Monotherapy

GEOGRAPHY ☐
- ☐ US
- ☐ Europe
- ☐ China
- ☐ Japan
- ☐ Other

MOLECULE TYPE ☐
- ☐ mAb
- ☐ Small molecule
- ☐ Bispecific
- ☐ Unspecified

☐ SELECT ALL  ☐ CLEAR                CANCEL    [APPLY]

From FIG. 11B

FIG. 11C

VIEW BY ◉ DRUGS ○ TRIALS

INDICATION
Drugs by phase of development

| | | |
|---|---|---|
| Top 30 | 43 \| 325 \| 73 \| 48 \| 26 | 1024 |
| Mid | 89 \| 69 \| 40 \| 58 \| 33 | 846 |
| Small | 32 \| 126 \| 73 \| 40 \| 33 | 980 |
| Non-industry | 32 \| 88 \| 69 \| 40 \| 21 | 71 |

○ Top 4  ○ Other solid  ⊙ Liquid  ⊘ Other  ⊙ Unspecified

TARGET
View by target

[CTLA-4]

| | | |
|---|---|---|
| Top 30 | 53 \| 43 \| 73 \| 325 \| 113 \| 18 \| 33 \| 26 \| 58 \| 9 \| 58 | 1024 |
| Mid | 113 \| 89 \| 69 \| 40 \| 73 \| 18 \| 33 \| 58 \| 45 \| 29 \| 32 | 846 |
| Small | 53 \| 43 \| 73 \| 325 \| 113 \| 18 \| 33 \| 26 \| 58 \| 9 \| 58 | 980 |
| Non-industry | 53 \| 43 \| 73 \| 325 \| 113 \| 18 \| 33 \| 26 \| 58 \| 9 \| 89 | 71 |

⊗ PD-1   ⊘ CD19   ⊙ PD-L1   ⊙ HER2   ⊙ IDO1
○ STAT3  ⊙ CTLA-4 ⊙ CD40    ○ CSFR1  ○ Other  ○ Unspecified From FIG. 18B

FIG. 18C

SYSTEM AND INTERFACES FOR PROCESSING AND INTERACTING WITH CLINICAL DATA

RELATED APPLICATIONS

This application claims priority under 35 U.S.C. § 119(e) to U.S. Provisional Application Ser. No. 62/821,014, filed Mar. 20, 2019, entitled "SYSTEM AND INTERFACES FOR PROCESSING AND INTERACTING WITH CLINICAL DATA", which is herein incorporated by reference in its entirety. Foreign priority benefits are claimed under 35 U.S.C. § 119 to Greek Patent Application No. 20190100084, filed Feb. 18, 2019, entitled "SYSTEM AND INTERFACES FOR PROCESSING AND INTERACTING WITH CLINICAL DATA," which is herein incorporated by reference in its entirety.

NOTICE OF MATERIAL SUBJECT TO COPYRIGHT PROTECTION

Portions of the material in this patent document are subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

There are computer systems that exist that allow users to view clinical trial data. However, it is appreciated that much of the data relating to clinical trials comes from many different sources, and many different organizations produce such data. For example, ClinicalTrials.gov is a database of privately and publicly funded clinical studies around the world. As another example, PUBMED is a database of citations, abstracts, and full text versions of biomedical literature from MEDLINE and additional life science journals.

SUMMARY

According to some embodiments, a software-based system and tools are provided that are adapted to process clinical trial data from one or more sources, both structured and unstructured data, and integrate such data in a database for access by users.

Further, in some embodiments, such trial data is combined with other types of data to train an AI-based model, for the purpose of determining a probability of a particular trial outcome. For instance, an AI model may be trained on one or more structured and/or unstructured data sources relating to clinical trials in order to train a model that can determine whether a candidate clinical trial will be successful for the purpose of de-risking clinical development. In some embodiments, it is appreciated that the clinical trial process is expensive in both time and money and is wrought with risk. Because of this, analytical tools that can predict outcomes of particular clinical trials and provide suggestions on how a particular trial may be improved would be most valuable. Such predictive analytics, may for example, instruct a company on changing one or more parameters of a clinical trial in order to affect the outcome of the trial (e.g., produce a positive outcome such as receiving FDA approval for a drug).

Further, in some embodiments, a unique database/data architecture is provided that maps the features/data that are captured across various data sources. In particular, parameters relating to one or more of clinical trial outcomes, regulatory parameters, company experience information, drug molecule characteristics, gene expression, indication characteristics, and/or clinical trial design characteristics may be captured and stored in a multidimensional database. Such a database may be used to train one or more AI models for the purpose of creating a predictive model for clinical trial outcomes. In some embodiments, a portal may be provided that allows users and/or processing entities to query current clinical trial data through a single interface.

In some embodiments, one or more software as a service (SaaS) tools are provided that allow users to access predictive analytics relating to clinical trial outcomes. In some embodiments, machine learning techniques are applied to solve clinical trial design problems with a focus on de-risking the clinical development process. In some embodiments, a computer-based system is provided that is configured to determine, in real time, estimates for a probability of regulatory approval for drugs. For instance, the system may be adapted to provide a probability estimate for drugs that are in a particular phase or juncture of a clinical trial. For example, the system may be adapted to determine a probability at Phase 1, Phase 2, or Phase 3 or any intermediary point of a clinical trial.

In some embodiments, machine learning algorithms may be provided that are trained on actual outcomes using one or more of the parameters discussed above. In some embodiments, the system is configured to develop those estimates based on a comprehensive set of multiple parameters (e.g., 50 or more drivers, 90 or more, etc.). According to some aspects, the system provides a comprehensive view of the relative strength of the predictive drivers behind those estimates, along with recommendations for maximizing regulatory approval. Further, in some embodiments, the system may include one or more user interface controls that provide insights into variables to change so that the probability of regulatory approval is maximized, and also allow a user to selectively modify AI-driven simulations of different clinical development scenarios and view modified probability outcomes.

In some embodiments, various implementations may have one or more of the following features. For instance, the system may generate and maintain unique ID information that link various data across the various data sources. In particular, in some embodiments, a unique relational database/data architecture is used to map the features/data that is captured across various data sources. For example, the system is capable of identifying unique immuno-oncology targets and retrieve relevant drugs and all the unique drug-indication pairs. In some embodiments, the system is configured to identify a lead indication for each active ingredient for a drug as well as important trials that lead to the regulatory outcome for that drug.

In some embodiments, the system is adapted to automatically link each asset (e.g., a drug-indication pair) to clinical trial design, setup, execution, targeted gene, regulatory features, through unique IDs that the system has generated. Further, the system may be adapted to automatically link each indication to EFO and mesh terms and automatically retrieve indication group data for prevalence and fatalities.

In some implementations, the system is configured to generate secondary features from primary data like number of patients per trial site or country groups that the trials took place in. In some implementations, the system takes into account historical success rates for the different indications to update probability estimates. Further, the system is capable of referencing drugs to corresponding publications (e.g., at PubMed) through automated query algorithms.

In some embodiments, a systematic methodology is provided for capturing different types of outcomes (e.g., Objective Response Rate, Overall Survival, Progression-free Survival, etc.). In some implementations, outcome data of clinical trials may be derived from one or more sources, such as publications (e.g., scientific articles available in PubMed, etc.). Such information may be created using one or more automatic methods (e.g., AI classification) alone or in combination with expert curation (e.g., review by experts).

In some embodiments, the machine learning model is trained using one or more regulatory parameters. For example, specific designations/pathways from the FDA may be used, for example "orphan disease" to train the model. Further, others such as "breakthrough" designation, or other FDA designations such as "accelerated approval", "fast track" and "priority review" may be used. Further, the system may be trained based on the history of past approvals (e.g., for different indications).

In some embodiments, it is appreciated that company experience (e.g., number of trials the company has conducted in the specific therapeutic area and/or indication) is highly indicative as to the probability of success. In addition to the predictive nature of an AI-driven model in some embodiments (i.e., estimating a probability of progressing to the next phase of development and/or regulatory approval), the computer system can also provide insights into how to maximize this probability, for example by selectively changing elements of the clinical trial design (for example endpoints, number of patients, arms, comparators, number of sites, etc.).

According to some aspects, a system is provided comprising a database adapted to store a plurality of sets of data relating to clinical trials of a plurality of drugs, an analytics engine adapted to determine, for a particular one of the plurality of drugs, a likelihood that the clinical trial associated with the particular drug and a particular indication will be successful, and an interface adapted to identify, to an entity, a measure of the likelihood. In some embodiments, the analytics engine includes at least one AI-based model optimized to maximize the likelihood.

In some embodiments, the analytics engine is adapted to selectively change one or more parameters of the clinical trial design to maximize the likelihood. In some embodiments, the analytics engine is adapted to modify at least one of one or more parameters of the clinical trial design including, without limitation, a number of patients in the clinical trial, a number of arms of the clinical trial, a number of comparators, a number of sites, and/or a number and type of endpoints in the clinical trial.

In some embodiments, the system further comprises a component adapted to retrieve data associated with the plurality of drugs and corresponding clinical trials from one or more data sources. In some embodiments, the interface includes one or more input controls that permit a user to modify one or more parameters of the clinical trial associated with the particular drug, and responsive to the one or more modified parameters, the analytics engine being further adapted to determine, for the particular one of the plurality of drugs, a modified likelihood that the clinical trial associated with the particular drug will be successful, and wherein the interface adapted to identify, to an entity, a measure of the modified likelihood. In some embodiments, the system further comprises at least one user interface control that when selected, causes the interface to modify one or more parameters of the clinical trial associated with the particular drug.

In some aspects, a method is provided comprising storing, by a database, a plurality of sets of data relating to clinical trials of a plurality of drugs, determining, by an analytics engine, for a particular one of the plurality of drugs, a likelihood that the clinical trial associated with the particular drug and a particular indication will be successful, and identifying via an interface to an entity, a measure of the determined likelihood. In some embodiments, the method further comprises an act of maximizing the likelihood using at least one AI-based model. In some embodiments, the method further comprises an act of selectively changing one or more parameters of the clinical trial design to maximize the likelihood.

In some embodiments, the method further comprises an act of modifying at least one of one or more parameters of the clinical trial design including, without limitation, a number of patients in the clinical trial, a number of arms of the clinical trial, a number of comparators, a number of sites, and/or a number and type of endpoints in the clinical trial.

In some embodiments, the method further comprises an act of retrieving data associated with the plurality of drugs and corresponding clinical trials from one or more data sources. In some embodiments, the method further comprises an act of permitting a user within an interface having one or more input controls to modify one or more parameters of the clinical trial associated with the particular drug, and responsive to the one or more modified parameters, determining, for the particular one of the plurality of drugs, a modified likelihood that the clinical trial associated with the particular drug will be successful, and identifying, to an entity, a measure of the modified likelihood. In some embodiments, the method further comprises an act of permitting a user to select at least one user interface control that when selected, causes the interface to modify one or more parameters of the clinical trial associated with the particular drug.

In some aspects, a non-volatile computer-readable medium is provided, the medium being encoded with instructions for execution on a computer system, the instructions when executed, provide a system comprising a database adapted to store a plurality of sets of data relating to clinical trials of a plurality of drugs, an analytics engine adapted to determine, for a particular one of the plurality of drugs, a likelihood that the clinical trial associated with the particular drug and a particular indication will be successful, and an interface adapted to identify, to an entity, a measure of the likelihood.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of a particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

FIGS. 3A-3B shows an example user interface showing machine learning information according to some embodiments;

FIG. 5 shows an example user interface showing analytics controls and features according to some embodiments;

FIGS. 9A-9B show an example user interface showing drug details according to some embodiments;

FIGS. 11A-11C show an example user interface showing the use of filters according to some embodiments;

FIGS. 18A-18C show an example user interface an example dashboard view that provides content based on the stakeholder according to some embodiments;

DETAILED DESCRIPTION

Figure 1:
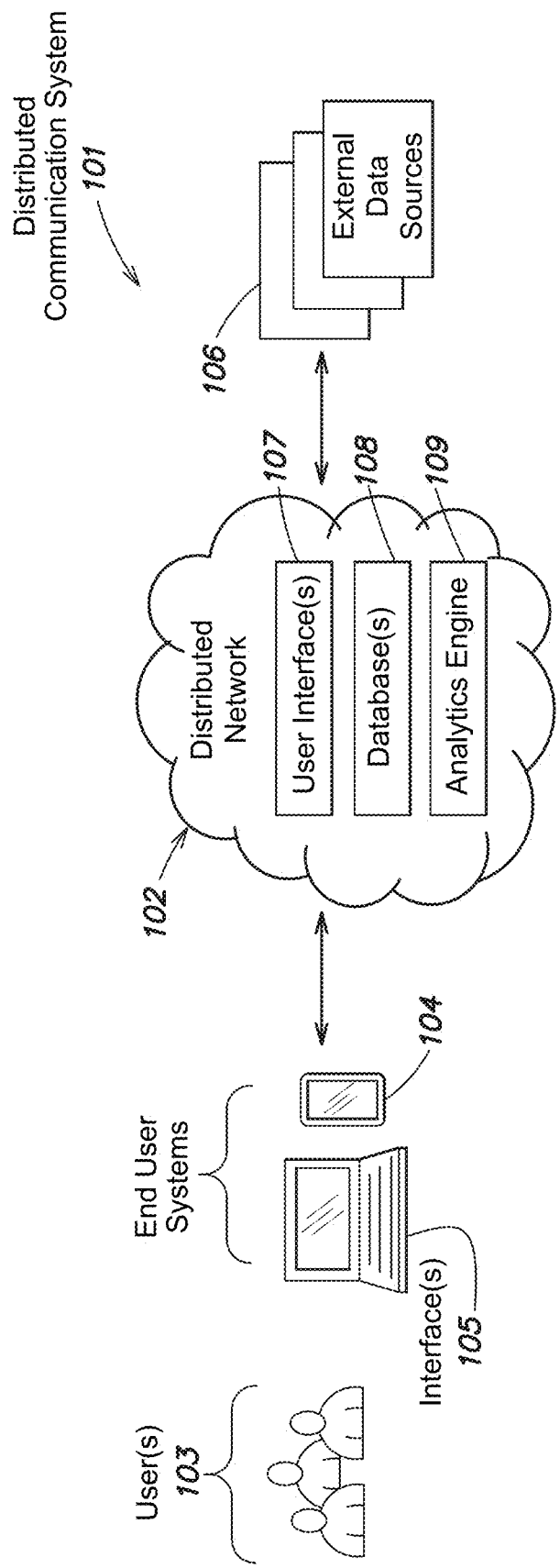
FIG. 1 shows a block diagram of a distributed computer system capable of implementing various embodiments.

According to one implementation, a system is provided that is capable of processing clinical trial data from one or more sources, both structured and unstructured data, and integrate such data in a database for access by users. Further, in some embodiments, such trial data is combined with other types of data to train an AI-based model, for the purpose of determining a probability of a particular trial outcome, among other insights. Further, the system stores the acquired data from multiple sources and provides search, comparison, and reporting capability within a single interface.

In particular, in some embodiments described herein, a computer-based system is provided that predicts and presents an indication to a user of a probability that a drug in clinical development will progress to the next phase of development (e.g., from Phase 2 to Phase 3), and/or receive FDA approval. In some implementations, the system applies machine learning to optimize parameters of the clinical trial design.

Further aspects relate to how data is collected and stored by the system. For example, in some implementations, unique methodology may be used that links dozens of data sources (e.g., in the public domain) to capture the variables that are used by the analytics. Further, other aspects relate to a process for codifying outcomes of previous clinical trials. Although some data is in the public domain (e.g., academic publications) it is appreciated that it is unstructured and not easily accessed through common methods. In some embodiments, a process is provided for processing such unstructured data, extracting relevant data, and capturing the data in a normalized format using a systematic methodology.

Other aspects relate to analytics for processing such data. In some embodiments, the system employs a unique methodology for processing (by machine learning algorithms) variables/features across multiple different categories, which can include:
- Clinical outcomes of the drug reported in previous phases (e.g. overall response rate (ORR))
- Regulatory (e.g., specific designations/pathways from the FDA, for example "orphan disease")
- Company experience (e.g., number of trials the company has conducted in the specific therapeutic area and/or indication)
- Drug/molecule characteristics (e.g. gene-disease association scores)
- Clinical trial design characteristics (e.g. number of patients, number of arms, allocation, etc.)

Clinical trial setup and execution (e.g. countries/sites, etc.)

Further, the system is configured to apply these machine learning algorithms on the data captured to perform one or more of the following features:

Identify predictive signals, and their respective strength, that drive a probability that a drug in clinical development will receive FDA approval Estimate the probability that a drug in clinical development will receive FDA approval Rank drugs in a certain portfolio by most likely to receive FDA approval Inform the design of clinical trials, based on simulation scenarios that have parameters that are modifiable by a user Further, various aspects relate to a common user interface where users can search, compare and report on clinical trials, along with any insights determined by the system.

FIG. 1 shows a block diagram of a distributed computer system 101 capable of implementing various aspects consistent with principles embodied by the present invention. In particular, distributed system 100 includes one or more computer systems (e.g., end user systems 104) operated by a user (e.g., users 103) and the system is accessed by the end user computer systems through a communication network (e.g., the Internet). Generally, users may access the distributed system through a client application that is executed on one or more of end systems (e.g., end user systems 104). End user systems 104 may be, for example, a desktop computer system, mobile device, tablet or any other computer system having a display.

As discussed, various aspects of certain embodiments described herein relate to accessing clinical trial data through a distributed network (e.g., distributed network 102). The distributed system may comprise one of ore components which may execute on one or more computer systems. For instance, user interface components (e.g., user interface(s) 107) may be accessed through one or more end systems. The interfaces may take the form of an app, website or other interface type. Further, the distributed system may include one or more databases (e.g., database(s) 108) adapted to store one or more data elements associated with a clinical trial and/or related information that can be used by the system. In some embodiments, the elements are obtained from one or more external data sources (e.g., sources 106) such as one or more of the data sources described in more detail below. Such information may include, for example, clinical trial data, company information, drug information, regulatory information, among others.

The system may also include an analytics engine (e.g. engine 109) which may include, for example, one or more models such as statistical models that may be trained to determine one or more outcomes based on the tested input. As discussed above, an analytics engine may be trained on one or more database elements that are received from one or more external data sources. For instance, the data may be relational, documents, files, or any other type of structured or unstructured data.

Some embodiments described herein relate to interfaces (e.g., interfaces 105) through which the user can interact with the distributed communication system 101 to obtain clinical trial information. To this end, users may access system via the end user system (e.g., system 104). As discussed, users may access the system for the purpose of viewing and interacting with clinical trial data.

Figure 2A:
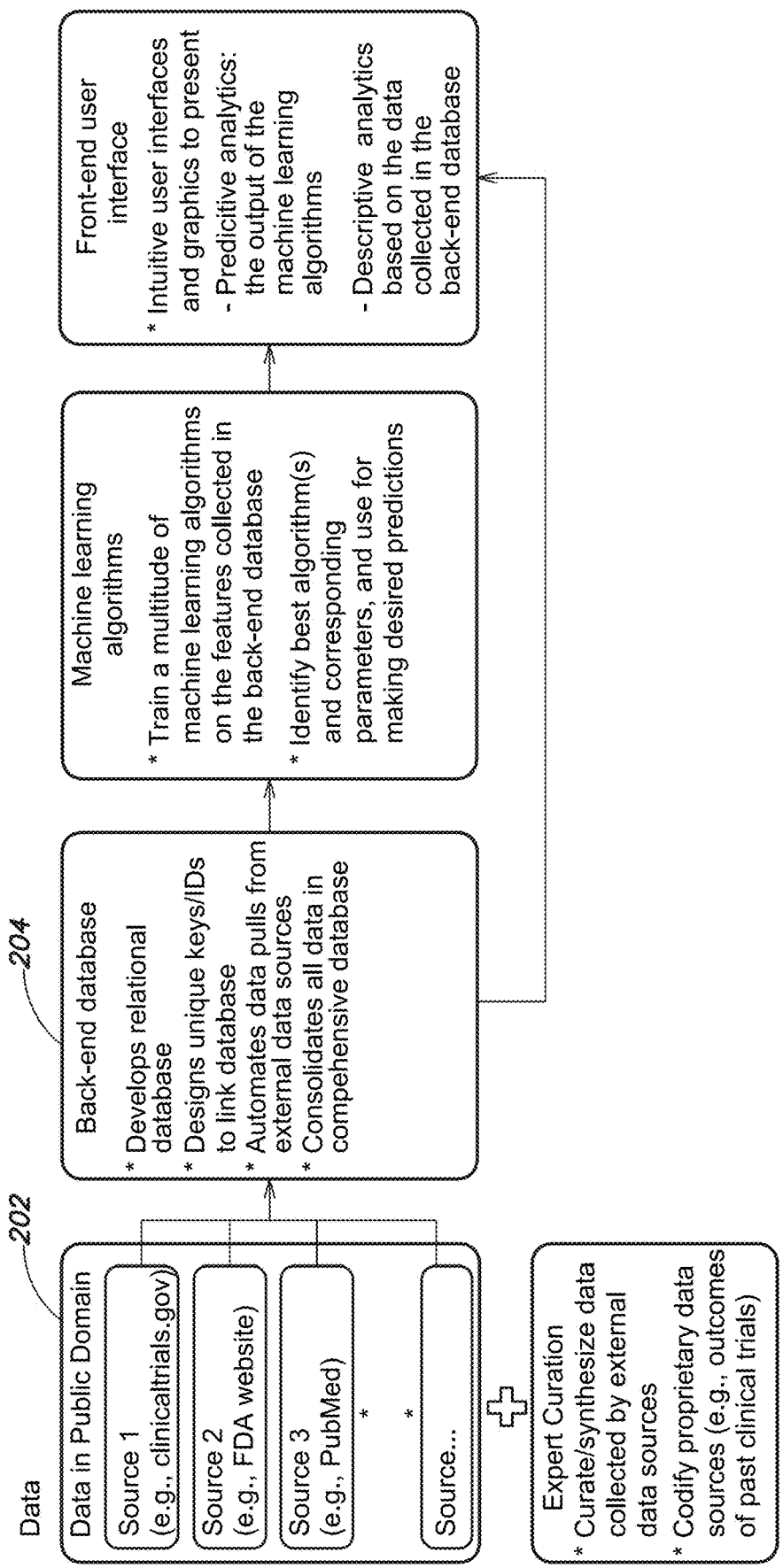
FIGS. 2A-2B show block diagrams showing a detailed implementation of a distributed system according to some embodiments.
Figure 2B:
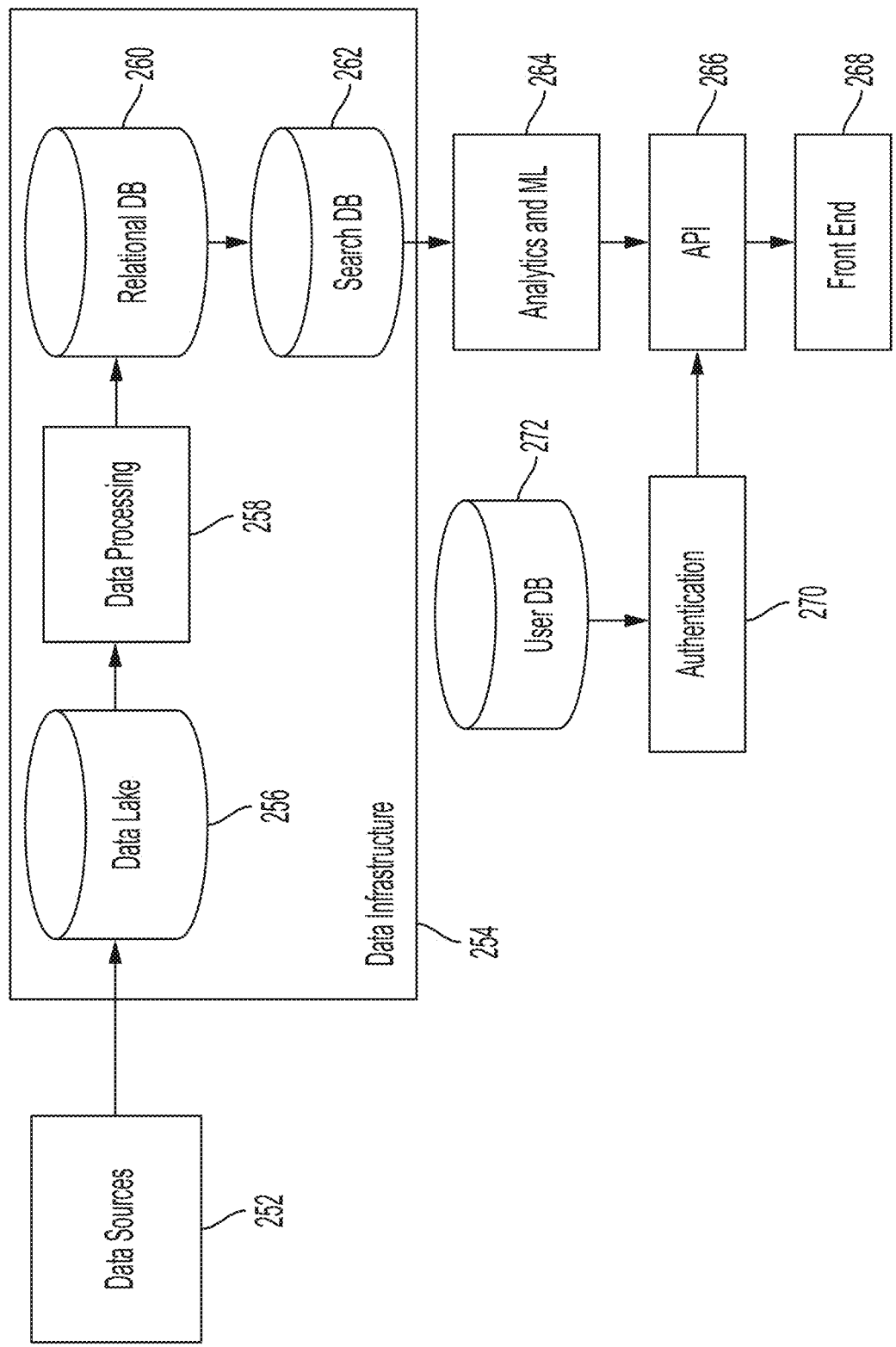

FIGS. 2A-2B show block diagrams showing a detailed implementation of a distributed system according to some embodiments. In particular, FIG. 2A shows a system wherein data 202 available within a number of sources 1, 2, 3 and so on within the public domain (e.g., clinical trials-.gov, FDA website, PubMed, etc.) are sourced within a backend database 204. In some instances, the database may be relational, but may be of any other type (e.g., NoSQL, document, etc.). The system is configured to design unique keys/IDs that link each of these database elements. The system automates data pulls from the external data sources and consolidates all available data within the database. In this manner, multiple sources need not be accessed independently.

FIG. 2B shows a system architecture, according to some embodiments. The data sources 252 (e.g., external data sources 106 in FIG. 1, data 202 in FIG. 2A, etc.) are collected and stored into the data infrastructure 254 as raw data (e.g., in a data lake 256). As described herein, the data infrastructure 254 can be used to provide a proprietary, curated database with dozens and/or hundreds of features for different clinical trials, drugs, genes, companies, and/or the like. The data lake 256 can be, for example, cloud storage. The data lake 256 can store both unstructured data (e.g., XML, OWL, RDF, JSON, CSV, etc.) and/or structured data (e.g., PostgreSQL/MySQL dumps, etc.).

The data infrastructure 254 includes data processing 258 that processes the data in the data lake 256 to generate the relational database 260. The data processing 258 can include tasks for making the data consistent. In some embodiments, terms such as drug names, indications, targets, company names, etc., can be made consistent across all of the external databases. In some embodiments, a set of ontologies or classifications can be used to make disparate terms across the data/databases consistent. For example, different drugs can be classified based on modalities or technologies (e.g., small molecule, biologic, gene therapy, DNA damage repair, antisense, etc.), target genes, mechanisms of action, and/or the like. In some embodiments, errors can be checked in the data, such as a clinical trial coded as both a randomized trial and a single arm trial. In some embodiments, the time dimension of available data can be taken into account when creating the data infrastructure (e.g., to avoid forward-looking bias. For example, a drug may be designated a "breakthrough therapy" by the FDA during Phase 3, but the designation was not known earlier in development, so the designation can be excluded when making a PTRS assessment during Phase 2 (or earlier).

The relational database 260 can be, for example, a database that leverages a normalized model, such as PostgreSQL. The relational database 260 can be used to provide a search database 262. In some embodiments, the search database 262 can be used to provide analytical information, such as aggregation information and/or statistical information (e.g., using the ClickHouse open source distributed database management system). The search database 262 can be used to provide data searching capabilities (e.g., using elasticsearch).

The data infrastructure 254 provides data used for analytics and ML 264. The analytics and ML 264 can include, for example, various scripts and analytics tools, such as python scripts, SciPy tools, NumPy library tools, pandas tools, Dask tools, and/or the like. According to some embodiments, machine learning algorithms are provided that are trained on features collected within the backend database, as discussed further herein. In some embodiments, the best algorithms are identified along with their corresponding parameters which are then used to make desired predictions (e.g., prediction of success of a candidate clinical trial). Further, the system may include one or more front end user interfaces which includes graphics and easily used controls to display predictive analytics developed from output of the machine learning algorithms. Further, descriptive analytics may be developed based on the data collected within the backend database.

In some embodiments, the data processing 258 can include automated data processing. For example, in some embodiments the automated data processing can include PostgreSQL scripts for structured data, elasticsearch for unstructured data and/or full text data, distributed multi-dimensional array processing (e.g., NumPy/Pandas/Dask), and/or the like.

In some embodiments, the data processing 258 can include receiving data processing information from one or more users. For example, data processing 258 can receive data entry, such as from internal sources, as well as expert sources (e.g., by biological scientists, PhD teams, etc.). It should be appreciated that for example, that one or more humans and/or experts can curate/synthesize data collected by external data sources. In some embodiments, they codify proprietary data sources such as outcomes of clinical trials which can be used to form the database and/or train the machine learning algorithms.

The results of the analytics and ML 264 are provided to users through the front end interfaces 268 via the API 266. The API 266 layer can include various tools such as Python scripts, Node.js web services, a graphics rendering back-end service, load balancing (e.g., NGINX), and/or the like. The API 266 can provide user authentication 270 (e.g., such as a single sign-on (SSO)). The user authentication 270 can leverage a user database 272 (e.g., a structured database, such as PostgreSQL) that includes information on users, accounts, and/or the like. The front end interfaces 268 can be provided using various tools, such as D3.js visualization tools, React user interface tools, and/or the like.

Figure 3B:
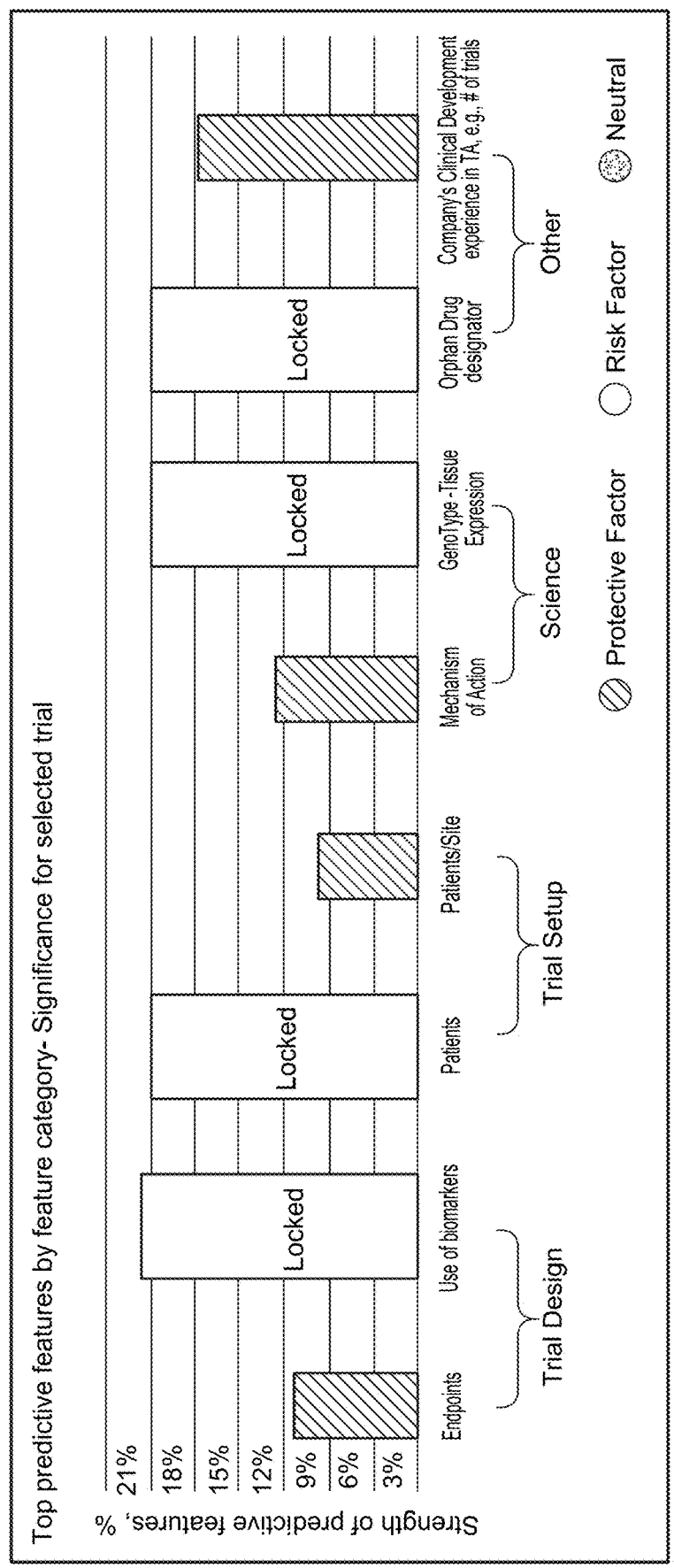

FIGS. 3A-3B show an example user interface showing machine learning information according to some embodiments. For example, the system may provide one or more interfaces to access machine learning characteristics associated with particular clinical trial. For example, as shown in FIG. 3A, a clinical trial with drug "Gazyva" having an active ingredient "Obinutuzumab" used for Leukemia treatment may be evaluated using a trained machine learning model. Notably, the interface may include the calculation of a probability of FDA approval for the clinical trial of Gazyva. In this particular example, the probability may relate to FDA approval estimated at a phase 2 start. The system may also estimate an average historical likelihood of FDA approval for drugs at the start of phase 2 development. In one implementation, the probability may be expressed as a percentage likelihood that the result will occur. Further, in some embodiments, the interface may be adapted to show the top predictive features by future category and their significance for a selected trial. More particularly, the interface may show certain aspects of a future category such as trial design, trial set up, science, or other feature category along with their strength of predictive features. This value may be expressed, for example, as a percentage of strength. For instance, in the example shown in FIG. 3B, a company's clinical development experience may be shown to be a highly predictive feature associated with the approval probability. Furthermore, the interface may include a confidence measure that indicates the sensitivity of the machine learning outcomes (e.g., as expressed by a very high to low sensitivity indication).

Figure 4:
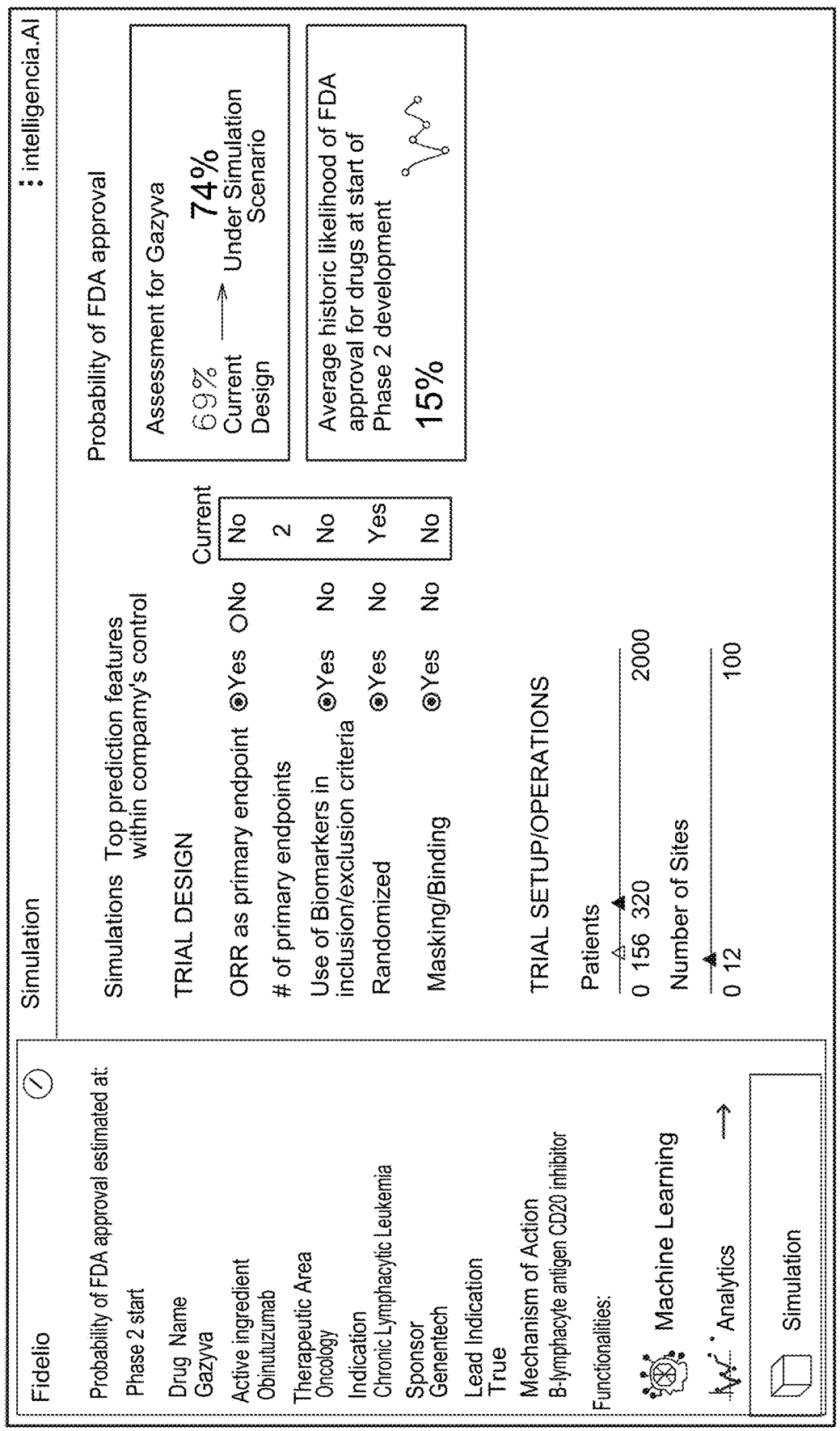
FIG. 4 shows an example user interface showing simulation controls and results according to some embodiments.

FIG. 4 shows an example user interface showing simulation information according to some embodiments. In particular, FIG. 4 shows an interface that include controls to adjust the simulation to produce the desired improved probability of FDA approval value. For instance, one or more predictive features may be within a company's control, and therefore "what if" scenarios may be tested against the model using various different trial design inputs. For example, the number of endpoints, number of patients, number of sites, type of trial, among other information may be used to adjust the simulation in order to improve the probability that a particular clinical trial will be successful (e.g., that FDA approval may be received). In some embodiments, the platform identifies variables that have a strong impact on the estimated probability of approval of a clinical trial. One or more techniques can be used to rank different variables used in an ML algorithm based on their importance/impact, such as by using univariate techniques (e.g., such as SelectKBest, which is a univariate technique that utilizes ANOVA F-values and chi-squared statistics for futures), multivariate techniques (e.g., Recursive Feature Elimination (RFE), which is a multivariate technique that utilizes coefficients from a logistic regression on the features to select the most important features by removing the least important features at each iteration), and/or the like. Such techniques can be run after the ML algorithm(s) are trained to determine a prioritized list of the most impactful variables, together with an associated weight that reflects the importance of each variable in the overall ML algorithm. The platform can run several permutations of different values for those identified variables to calculate the extent to which the probability can be increased.

Figure 5:
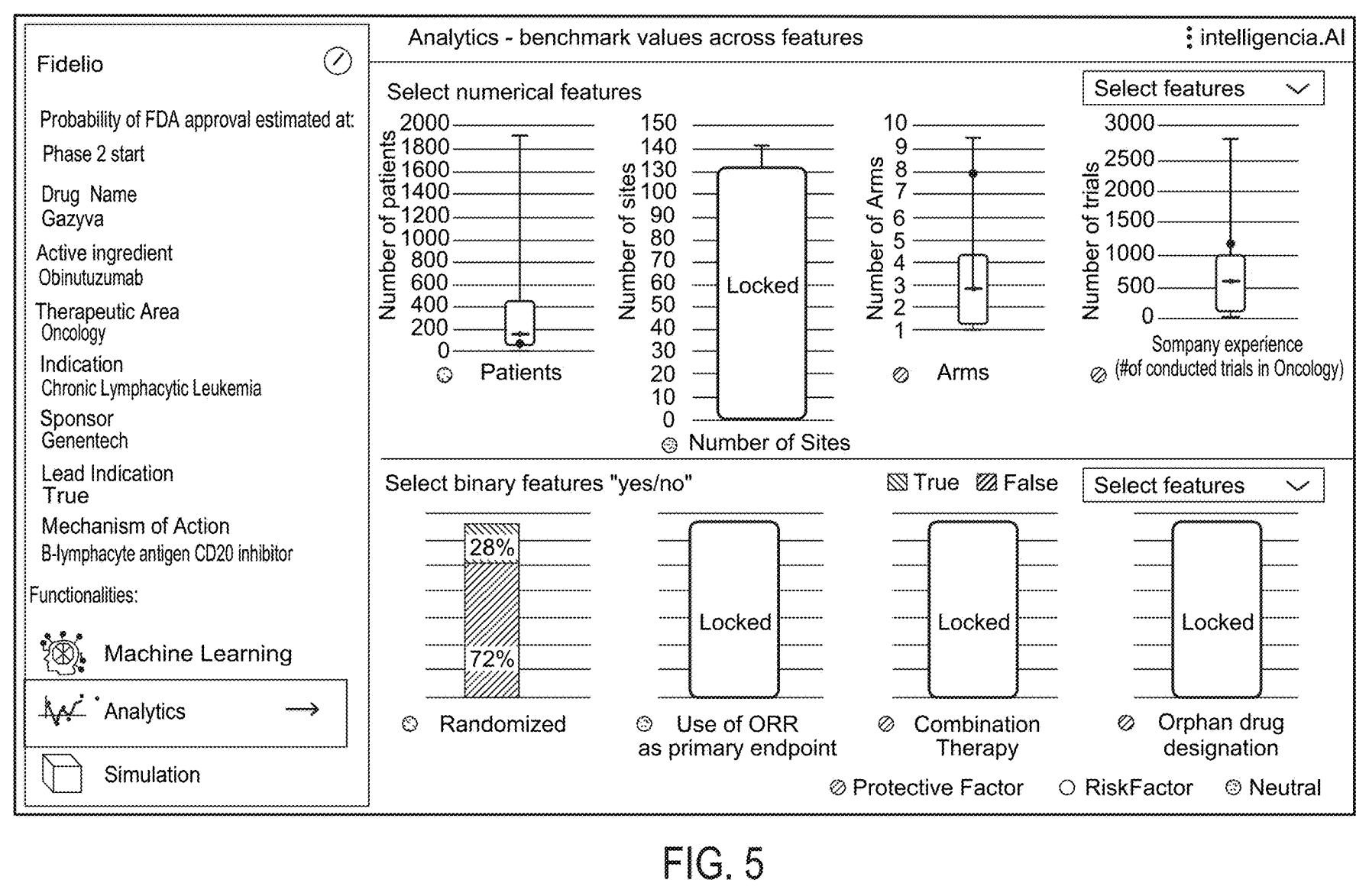

The interface may include a machine learning tab that allows a user to select such information. For example, the user may proceed to a further user interface (e.g., as shown in FIG. 5) that displays some more detail relating to the analytics performed by the system. Using the same example in FIG. 3 for the clinical trial with drug "Gazyva" having an active ingredient "Obinutuzumab," the interface may include one or more controls that allows the user to adjust certain aspects of the clinical trial. For example, the system may include a control that allows the user to select the number of patients associated with the trial, number of arms, company experience, etc. Further, the interface may include one or more controls that allow the user to adjust binary features such as yes/no inputs for particular features. Another control may permit the user to display which features could be controlled either within the numerical features or binary features windows.

Data and Analytics

As discussed above, a unique database/data architecture is provided that maps the features/data that are captured across various data sources. It In particular, parameters relating to one or more of clinical trial outcomes, regulatory parameters, company experience information, drug molecule characteristics, gene expression, indication characteristics, and/or clinical trial design characteristics may be captured and stored in a multidimensional database. Such a database may be used to train one or more AI models for the purpose of creating a predictive model for clinical trial outcomes.

Data sources may include (but are not limited to) clinical trial outcome data, regulatory information, company experience information, drug molecule characteristics, gene expression, indication characteristics, clinical trial design characteristics, and/or clinical trial set-up and execution information. Clinical trial outcome data can include, for example, scientific articles/publications from PubMed, ClinicalTrials.gov, EudraCT, WHO ICTRP, company websites, Rosacea foundation, other websites, such as drugs.com, cancer.gov, cancer.org, etc., and/or the like. Regulatory information can include, for example, FDA website information, information from company websites, from other websites, such as drugs.com, cancer.gov, cancer.org, orphanet, check.orphan, friends of cancer research, etc., and/or the like. Company experience can include, for example, Clinicaltrials.gov, company financial statements, company websites, and/or the like. Drug molecule characteristics can include, for example, EBI/ChEMBL, Slapenrich, Phenodigm, Expression Atlas, Cancer Gene Census, EuropePMC, Uniprot, Eva Somatic, Drugbank, Geneontology, and/or the like. Gene expression can include, for example, Genotype-Tissue Expression from the NCBI, GTEX project, Gene-Disease Association Score from targetvalidations.org, and/or the like. Indication characteristics can include, for example, worldwide cancer statistics from WHO, U.S. cancer statistics from USCS, U.S. cancer statistics from the American Cancer Society, and/or the like. Clinical trial design characteristics can include, for example, scientific articles/publications from PubMed, Clinicaltrials.gov, company websites, and/or the like. Clinical trial set-up and execution can include, for example, Clinicaltrials.gov, EudraCT, WHO ICTRP, and/or the like.

Notably the system may be adapted to capture multiple features (e.g., over 90 features, over 135 features, etc.) relating to these categories across which the system 'catalogue' the outcomes of a trial, based on the example sources discussed above for clinical trial outcome data. For training the model, the system may capture (i) if each of those outcomes was measured or not, (ii) the value of the outcome (if it was measured), and (iii) any specific attributes of the value (e.g., if it was measured at 3 months, 6 months, etc.). Some of the information used to train the model may include one or more of the feature categories: overall response rate (ORR), overall survival (OS), progression-free survival (PFS), durability of response, safety, RECIST criteria, and/or the like.

As discussed herein, regulatory data (e.g., specific designations/pathways from the FDA, for example "orphan disease") may be used to train the model and impact the probability of approval. For instance, the following provides exemplary FDA features (note that this is not an exhaustive list, and other parameters may be used alone or in combination with any other parameter(s)): orphan disease, breakthrough designation, other FDA designations (e.g., Accelerated approval, Fast Track, Priority Review), history of past approvals (e.g. for different indications), and/or the like.

In some embodiments, company experience (e.g., number of trials the company has conducted in the specific therapeutic area and/or indication) may be used to train the model and impact the probability of approval. For instance, the following provides exemplary company experience features (note that this is not an exhaustive list, and other parameters may be used alone or in combination with any other parameter(s)): the number of trials conducted by the company in the specific disease area, number of successful trials, number of drugs approved in specific therapeutic area, total number of trials conducted by the company, company sales, if the product has been in-licensed or not, investigator experience, type of sponsor, licensed in/out, and/or the like.

In some embodiments, drug/molecule characteristics (e.g., gene-disease association scores) may be used to train the model and impact the probability of approval. For instance, the following provides exemplary drug/molecule characteristics features (note that this is not an exhaustive list, and other parameters may be used alone or in combination with any other parameter(s)): type of molecule, name of molecule, indication, mechanism of action, route of administration, gene/disease association score, and/or others (e.g., animal models, RNA expression, etc.).

In some embodiments, clinical trial design characteristics (e.g., number of patients, number of arms, allocation, etc.) may be used to train the model and impact the probability of approval. For instance, the following provides exemplary clinical trial design characteristics features (note that this is not an exhaustive list, and other parameters may be used alone or in combination with any other parameter(s)): number of patients, expected duration, inclusion/exclusion criteria, comparators, biomarkers, number of arms, allocation methodology, number of endpoints, types of endpoints, basket trial (yes/no), adaptive design (yes/no), part of multiple similar studies (yes/no), and/or the like.

In some embodiments, clinical trial setup and execution (e.g., countries/sites, etc.) may be used to train the model and impact the probability of approval. For instance, the following provides exemplary clinical trial setup and execution features (note that this is not an exhaustive list, and other parameters may be used alone or in combination with any other parameter(s)): number of sites, number of countries, list of countries, investigators, and/or the like.

Further, in addition to the categories above, the system may capture and use some basic information about the company and drug. For instance, information like company name, drug name, therapeutic area, phase of development, etc. may be captured and used by the system.

Figure 2C:
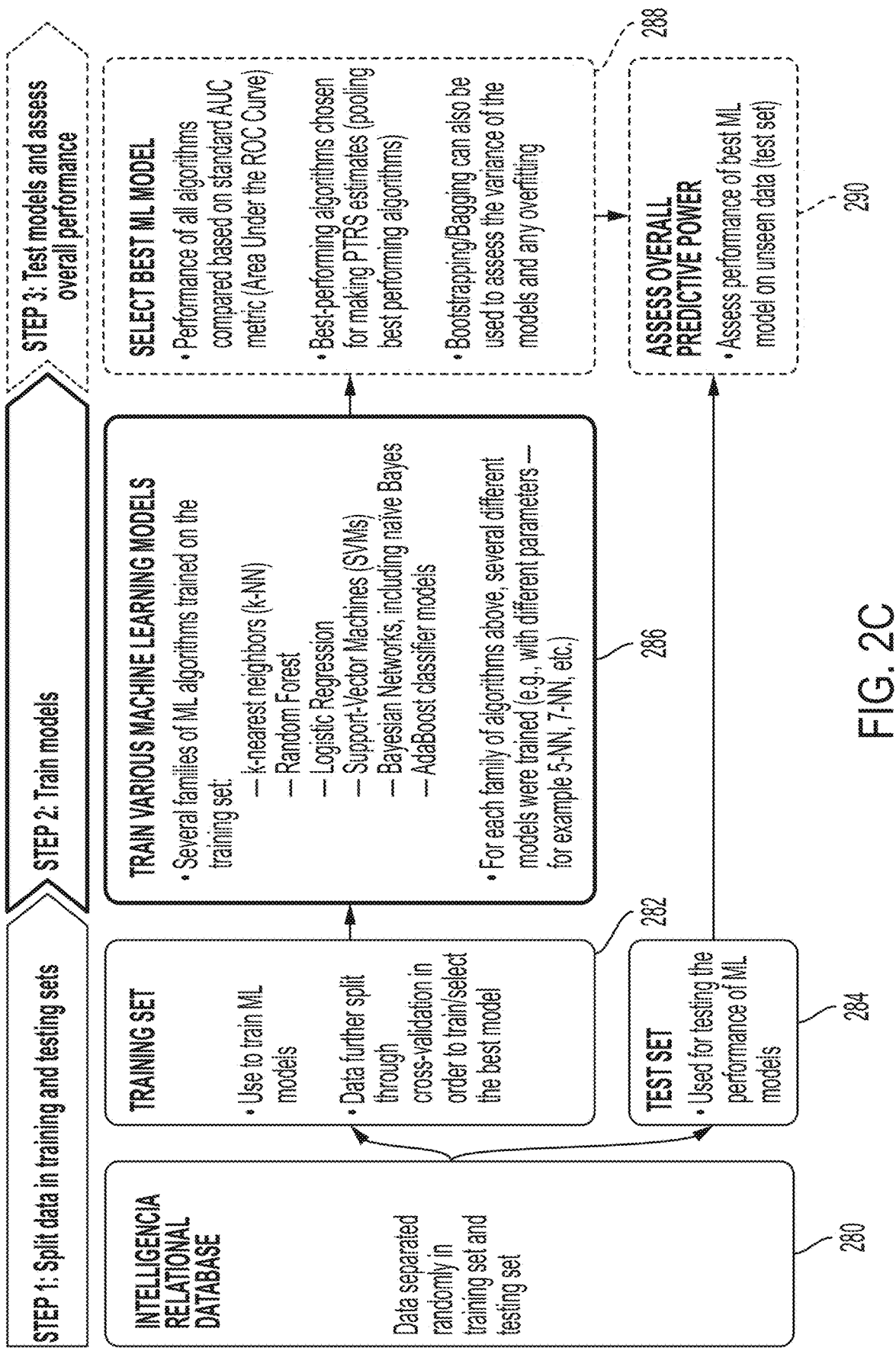
FIG. 2C shows an exemplary computerized process that can be used to train and test a set of ML models, according to some embodiments.

As discussed herein (e.g., in conjunction with analytics and ML 264), one or more machine learning (ML) algorithms may be used to analyze one or more data sets described above. FIG. 2C shows an exemplary computerized process that can be used to train and test a set of ML models, according to some embodiments. At step 1, the data from the back-end database 280 is split (e.g., randomly) into training and testing sets 282, 284 of data. In some embodiments, one of more of the following steps are involved to process the data. Initially, some preprocessing steps may be performed on the input data. For example, data pre-processing steps such as imputing missing data, standardizing variables, bin continuous variables, etc. may be performed. Further, the data set may be split in order to train, cross-validation, and test the machine learning (ML) model.

Further, the techniques may fill in missing data using various imputation methods corresponding to the category of each feature. For example, if certain data is missing from a particular trial, the system may automatically impute those features based on statistical methods that use information/values from other trials for which data is not missing, and adjusting those values for the trial with missing data based on all commonalities on all other characteristics. Also, the system may generate secondary features (e.g., number of patients per site, based on, for example, expert input from company employees and/or scientific advisors). Some data enrichment may be performed, for example, by the system, using rule-based, AI-based models, or other components.

In some embodiments, the techniques can include processing the data to prepare the data for training ML models. In some embodiments, the techniques can include binning. For example, for some ML models, the data can be preprocessed to avoid overfitting, such as by binning continuous variables (e.g., number of patients) into discrete groups (e.g., <20, 20-49, 50-99, 100-249, 250+, etc.). In some embodiments, the techniques can include imputation. For example, when features are missing for a particular trial, the techniques can include performing imputation (e.g., kNN imputation, unconditional mean imputation, etc.), listwise deletion and/or the like to generate a full data set. In some embodiments, to avoid data leakage, data processing (e.g., binning, imputation, and/or the like) can be performed within the cross-validation folds.

In some examples, a number of trials can be used to train the ML algorithms. For example, approximately 3,000 trials, approximately 4,000 trials, approximately 5,000 trials, approximately 6,000 trials, approximately 7,000 trials, approximately 10,000 trials, and/or some other number of trials can be used to train the ML algorithms.

In some embodiments, various types of database structures can be used to organize the data for training. For example, the data sets and/or different databases can be aligned on various dimensions. Such alignment can include different data-vectors that are of different lengths. A multi-dimensional data structure (e.g., a data cube) can be used to organize the data, such as by grouping it into different dimensions, indexing the data, and/or precomputing queries. Such data structures can hold large numbers of data points that can be used for training the ML algorithms. For example, the data structures can include thousands, hundreds of thousands, millions, billions, and/or more data points that can be used to train the ML algorithms. In some embodiments, for example, a data cube can be used to train the ML algorithms that includes more than one billion data points.

Referring further to FIG. 2C, the training set 282 is used to train the ML models (286). In some embodiments, the training set 282 is further split (e.g., through cross-validation) in order to train and/or select the best model(s). In some embodiments, one or several ML algorithms and/or families of ML algorithms can be trained using the training set 282. Examples include k-nearest neighbors (k-NN), Random Forest, Logistic Regression, Support-Vector Machines (SVMs), Bayesian networks (e.g., including naïve Bayes) AdaBoost classifier models, and/or other ML models. For each algorithm and/or family, the techniques can include training several different models (e.g., by varying the parameters of each model, such as 5-NN, 7-NN, etc.).

In some embodiments, at least one ML model may be trained to group feature values into different sizes per group associated with the outcome of the trial (e.g., to perform intelligent binning of the data). The system may then identify and select the variables that are likely to be most predictive (e.g., by using feature selection algorithms like SelectKBest). The system may then train multiple (e.g., 200+) models using different families of algorithms as described above (e.g., k-nearest neighbors, random forest, naïve Bayes, etc.).

At 288, the techniques include selecting one or more ML models by testing the models and assessing overall performance of the models. In some embodiments, the performance of the various trained ML models can be compared based on a metric, such as an Area under the ROC Curve (AUC) metric. For example, good performance can be a ML model with an AUC>0.85; OK/average performance can be a ML model with AUC>0.78, and/or the like. In some embodiments, the best performing algorithms are chosen for making PTRS (Probability of Technical and Regulatory Success) estimates (e.g., pooling the best performing algorithms). In some embodiments, bootstrapping methods can be used to assign a level of confidence to each of the PTRS predictions made by each best performing model (e.g., by assessing the variance of the models and any overfitting).

The test set 284 is used for testing the performance of the trained ML models (e.g., such that the best ML models can be assessed based on unseen data). The ML models are tested on the test set 284, and the top algorithms are chosen based on performance (290).

A combined model may be then created by using the top algorithms found from the previous step and that uses also different types of ML methods. The predictions of the algorithms are scaled, and sample predictions are made for trials that are still under development. Outcome probabilities are modeled for trials with changed characteristics than the original ones to optimize trial design. Also, the system outputs a comparison list between different drugs by outcome probability.

There are a number of predictive signals and their respective strength, that the system may determine, from the ML model which drive of probability that a drug in clinical development will receive FDA approval. In particular, the trained models that perform the best (based on methodology above) are used to identify which of the input variables have the highest impact on the outcome (PTRS). For example, one fairly strong predictive signal is whether the company has included ORR (objective response rate) as a primary endpoint for the trial. The algorithms may be used to rank the features in terms of their importance/"predictive power". In particular, the drugs of a certain portfolio may be ranked based on our predicted PTRS. It is appreciated that error ranges vary for each prediction/drug, and bootstrapping may be used to assign a "confidence level" to each of our estimates.

For any of these drugs, a user is permitted to vary the parameters of the study design (such as the number of patients, the number of countries, the biomarkers, etc.) using the interface and then the ML model recalculates and provides an updated PTRS based on each desired simulation scenario. As described herein, the platform can identify one or more variables that have a high impact. The platform can run several permutations of different values for those variables to determine the extent to which the probability can be increased (e.g., based on user selection of those parameters and/or automatically to provide the user with other options).

Additional Interfaces

Figure 6:
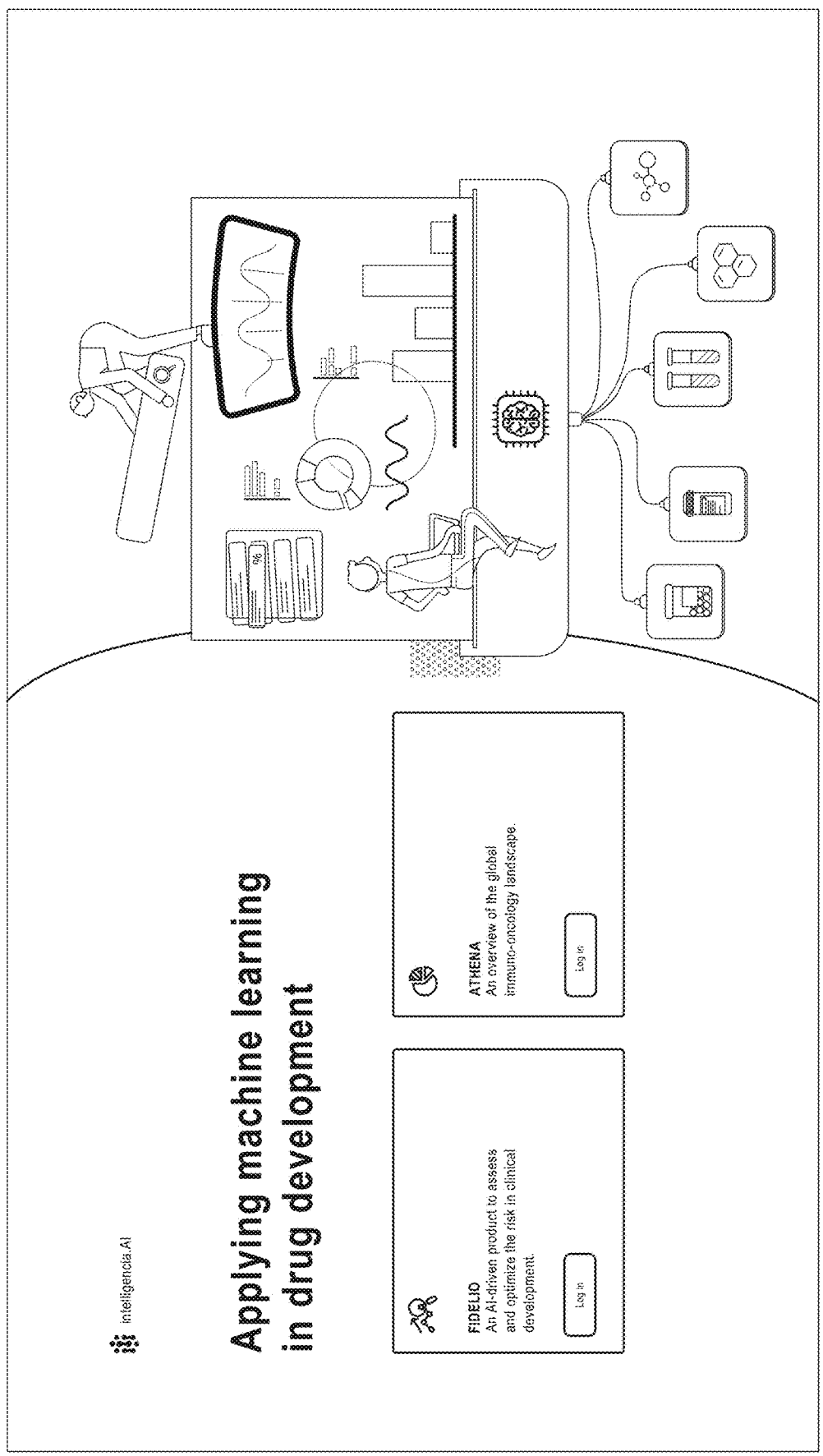
FIG. 6 shows an example user interface showing an introductory logic interface according to some embodiments.

FIGS. 6-21D show additional interfaces that permit the user to access, query and filter drug and clinical trial data. For instance, FIG. 6 shows an example user interface showing an introductory login interface according to some embodiments. The user interface is shown in FIG. 6 allows the user to login to view clinical trial information generally and/or gain access to AI driven results as discussed above with reference to FIGS. 3A-5. When selected, one or more controls may cause a login process to be initiated the interface.

Figure 7A:
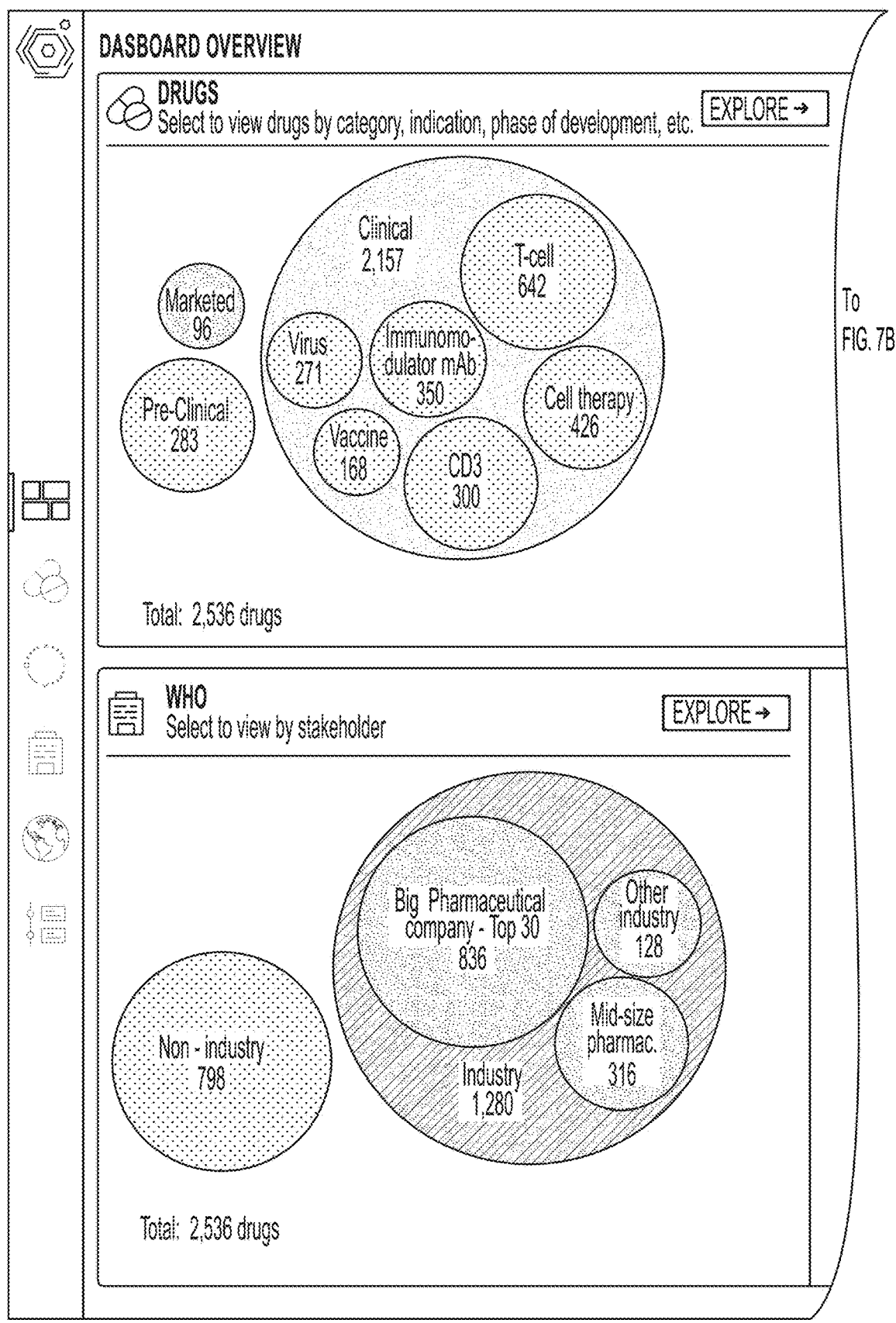
FIGS. 7A-7C show an example user interface showing an example dashboard view according to some embodiments.
Figure 7B:
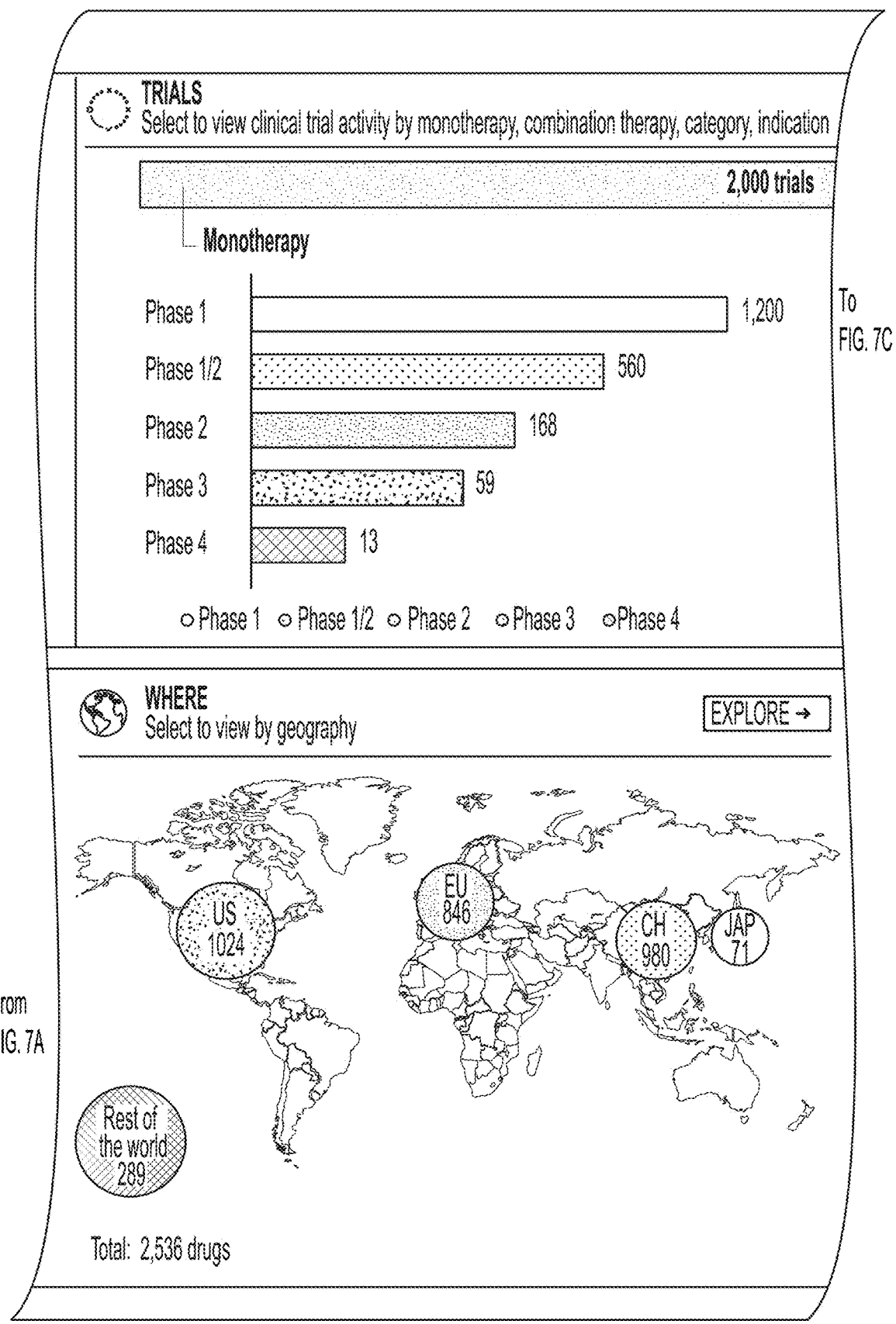
Figure 7C:
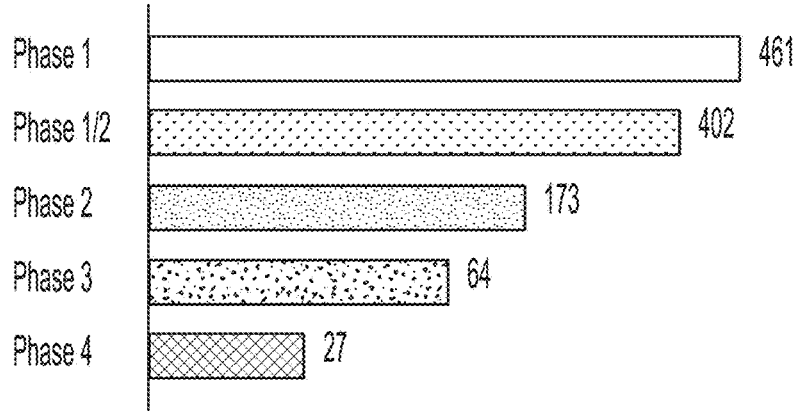
Figure 8A:
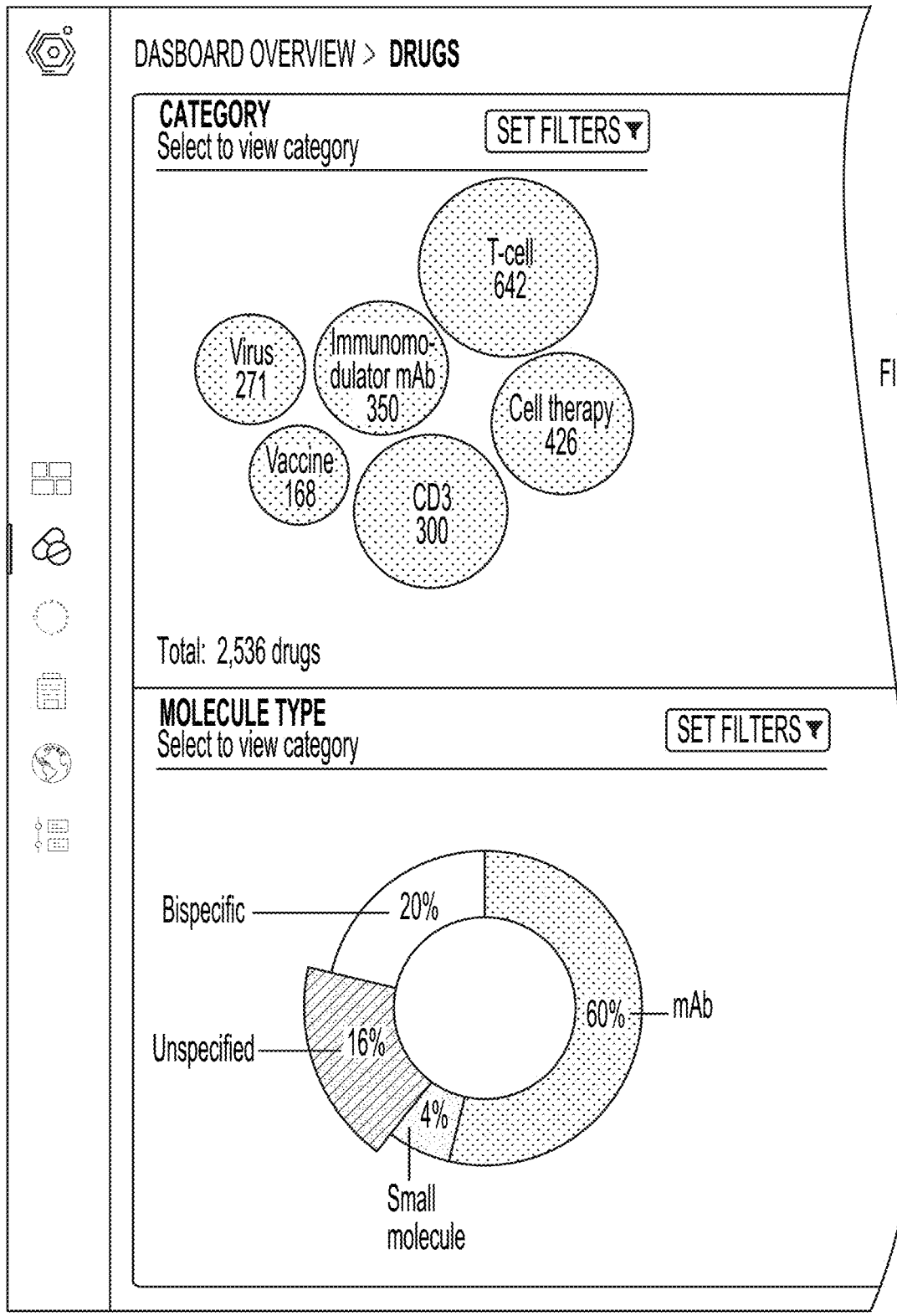
FIGS. 8A-8D show an example user interface showing another example dashboard view according to some embodiments.
Figure 8B:
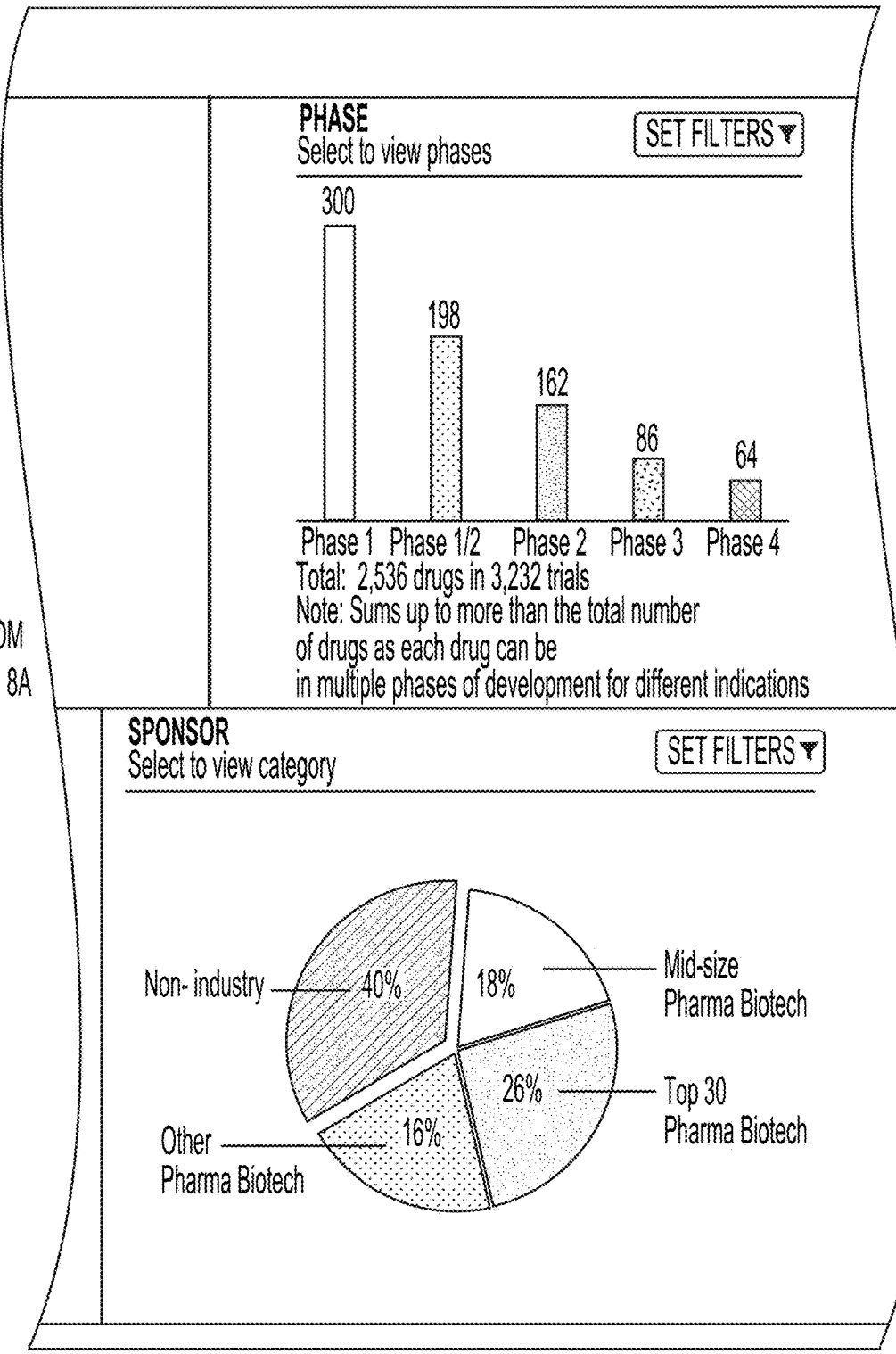
Figure 8C:
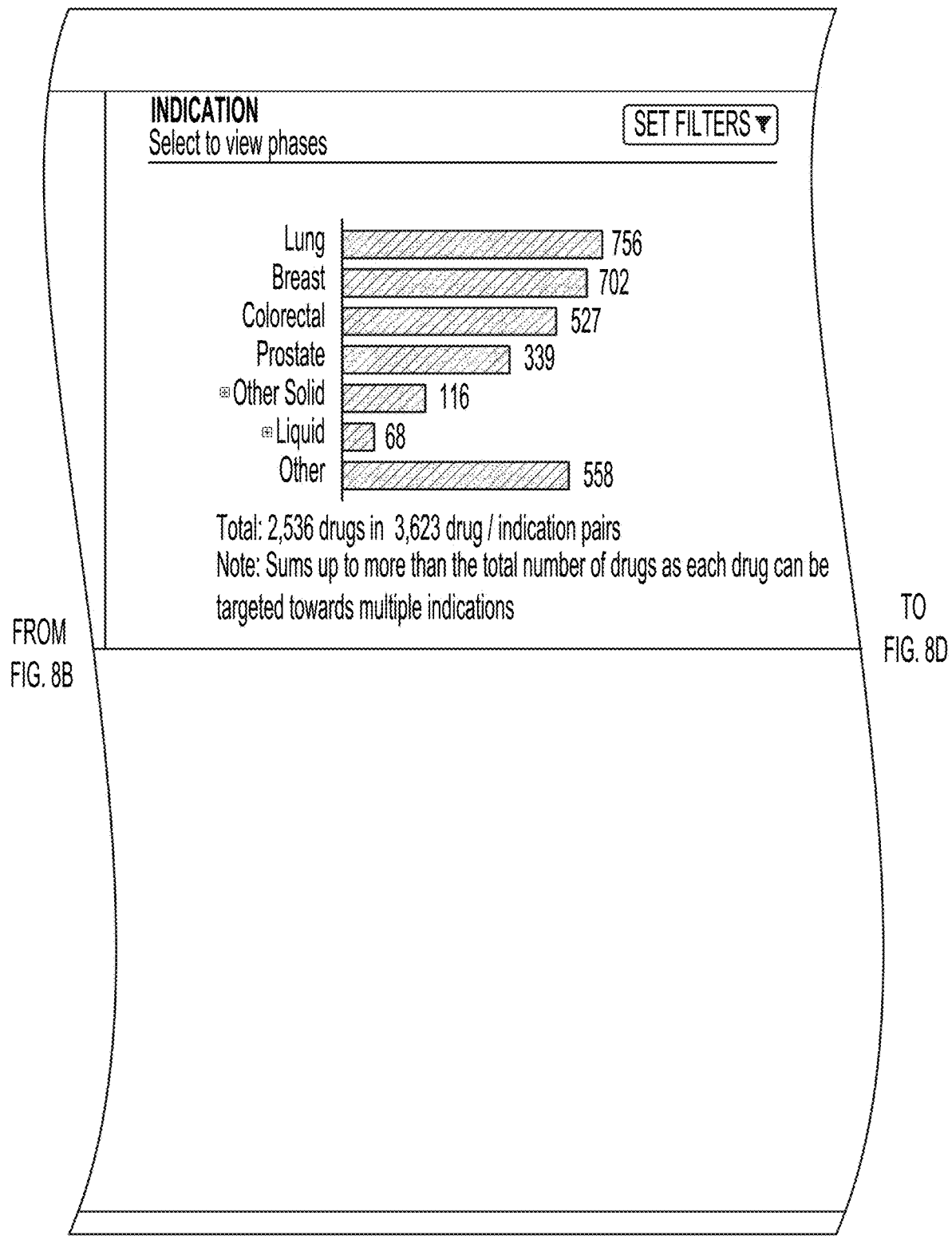
Figure 8D:
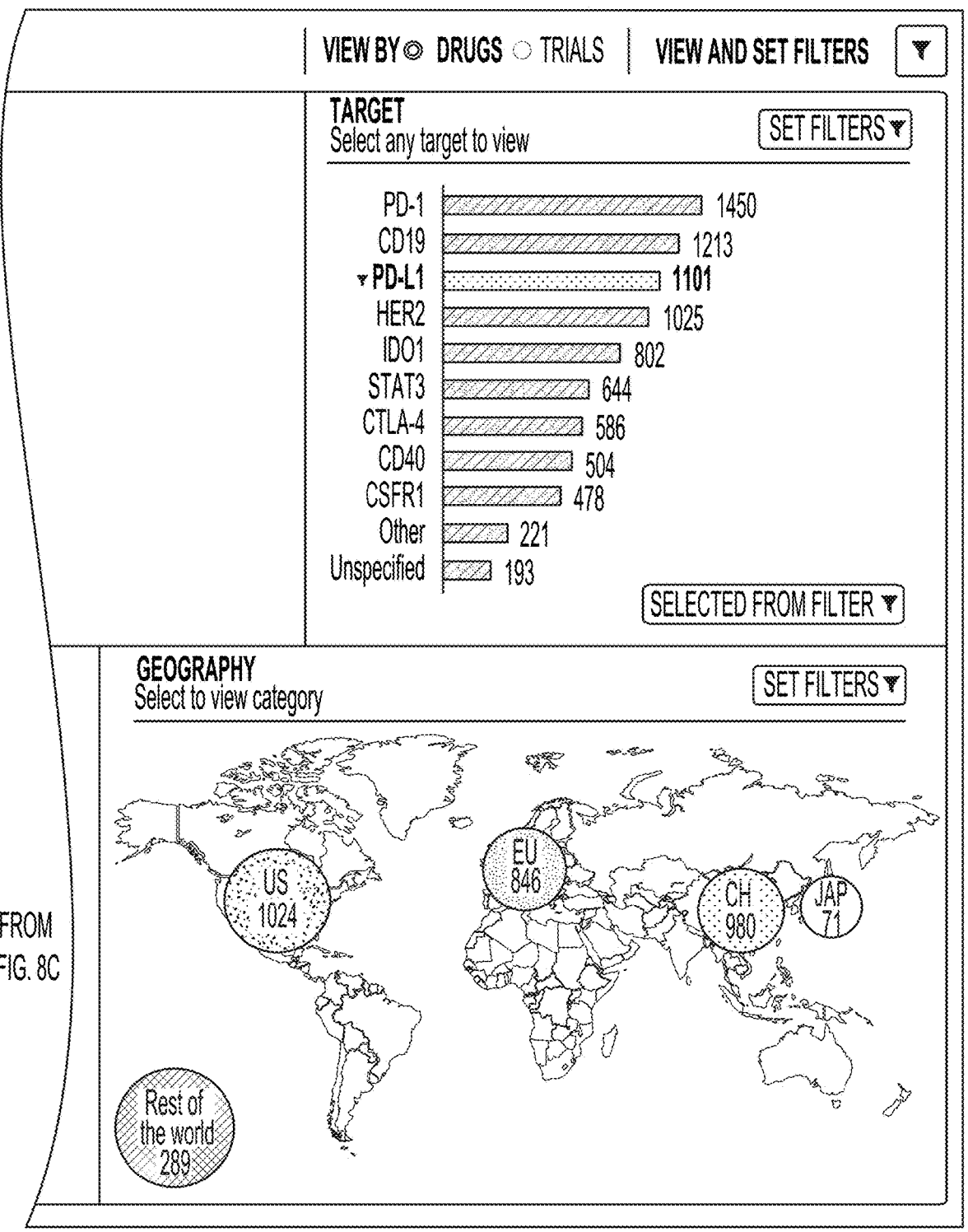

For example, once logged into the portal, the user can view clinical trial information generally, and can be presented with a dashboard view interface. FIGS. 7A-7C show an example user interface showing an example dashboard view according to some embodiments. Within the interface, the dashboard view may include a number of sub views that allow the user to selectively query the data and see results in real time. For example, one of the sub views may include drugs where the user may drill down into more particular information on drugs. The dashboard view may also include a trial area that allows the user to view clinical trial activity by monotherapy, combination therapies, category, indication, phase of development, and/or other parameters. The dashboard view may also include a "who" view that includes items relating to who is conducting the trials (e.g., stakeholder such as pharma companies or other industries), a "where" view that shows the geography of where clinical trials are being held, and a "when" view that allows the user to drug development over time. Through these dashboard views, user may more quickly locate clinical trial information without having to access multiple databases and sources.

FIGS. 8A-8D show an example user interface showing another example dashboard view according to some embodiments. For instance, in this example dashboard view, the user is permitted to view drug or trial information and can selectively set filters to be used. For example, within the interface, the user may be able to view and select different categories, select different medications, and the user can set different targets. Further, the user may be permitted to filter based on category of molecule type, sponsor, or geography, or any combination thereof between all these filters. In this way, the user interfaces can be highly adaptable to permit the user to drill down to the specific information that is required.

Figure 9A:
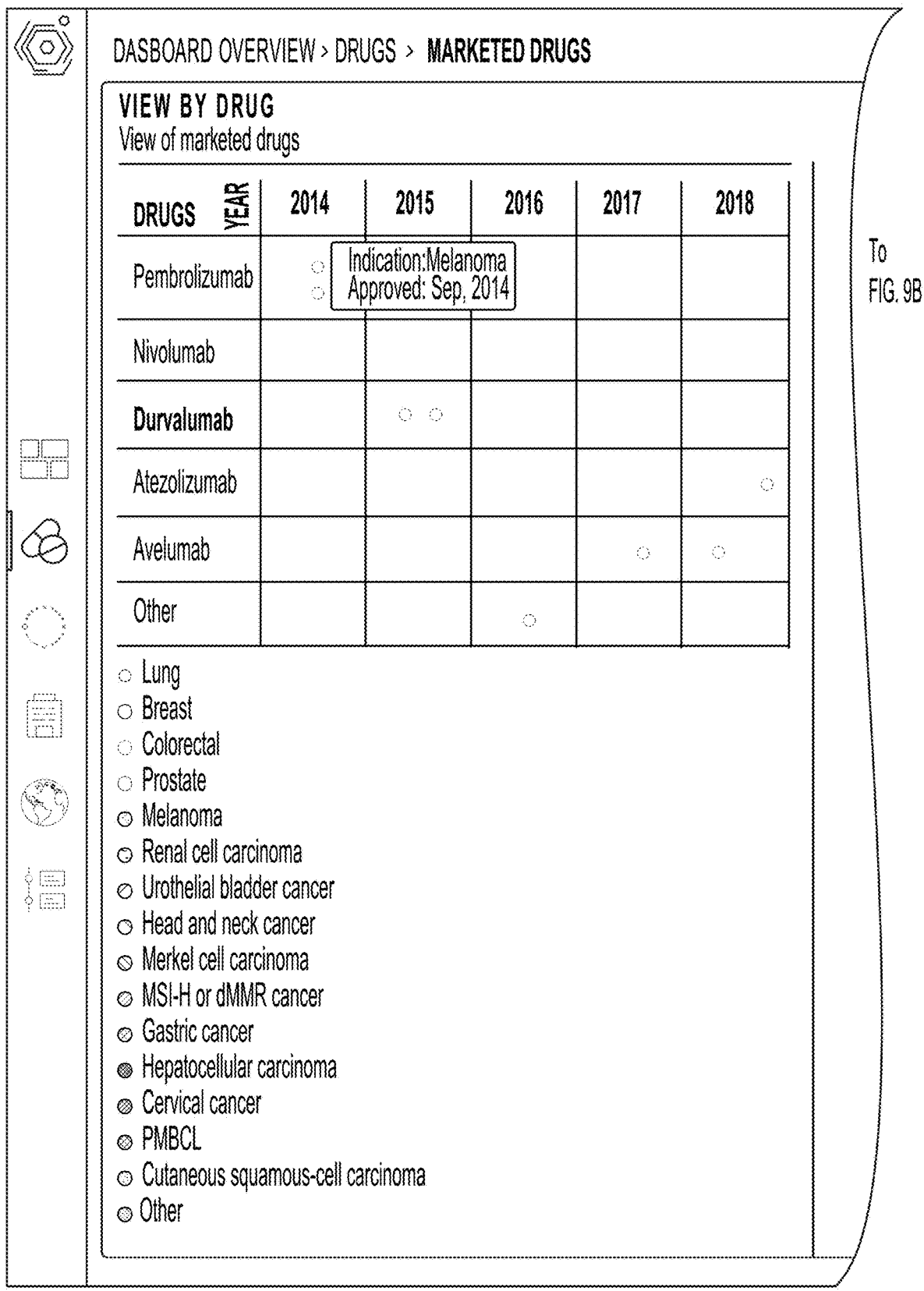
Figure 10A:
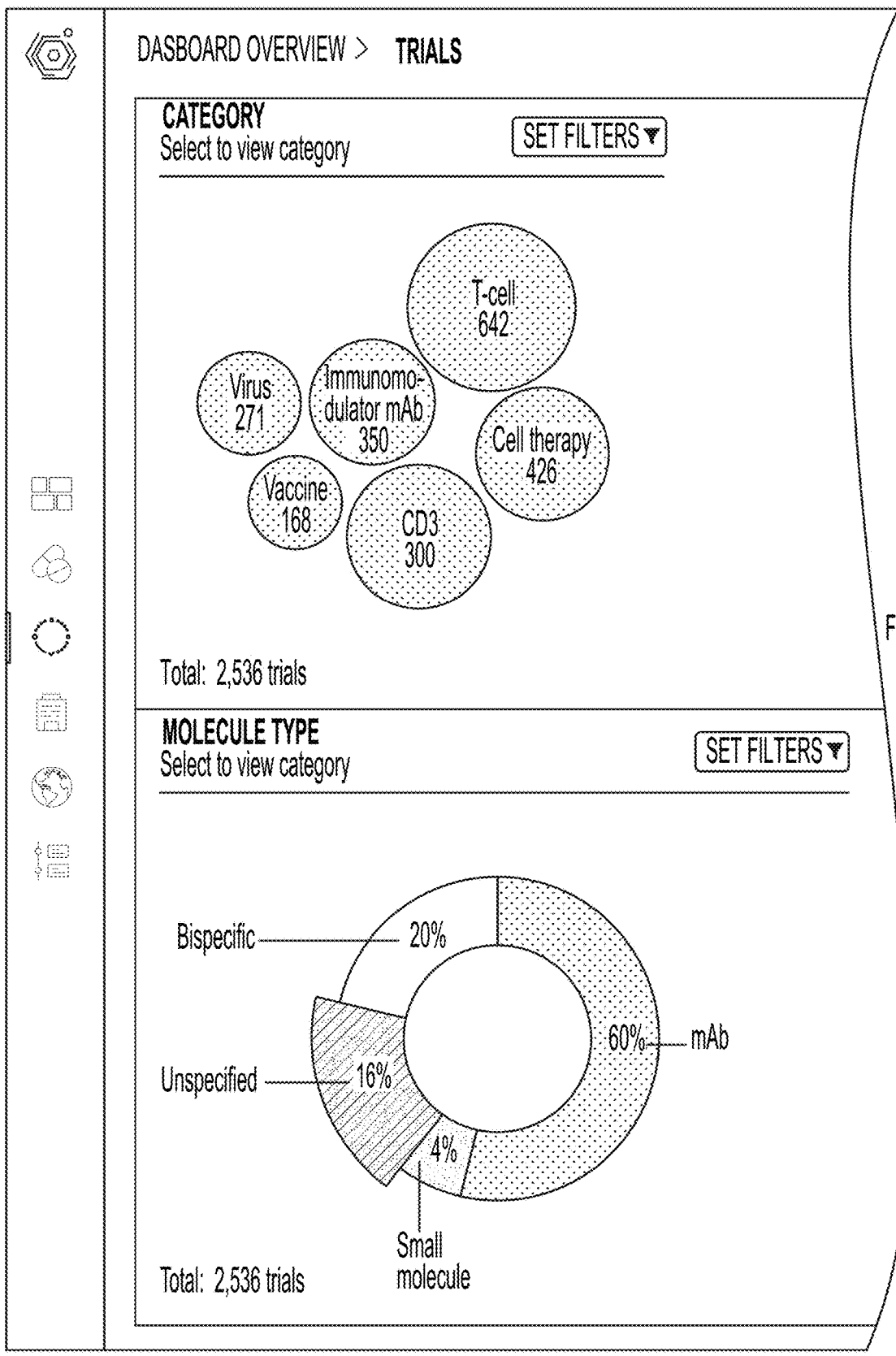
FIGS. 10A-10D show an example user interface showing trial details according to some embodiments.
Figure 10B:
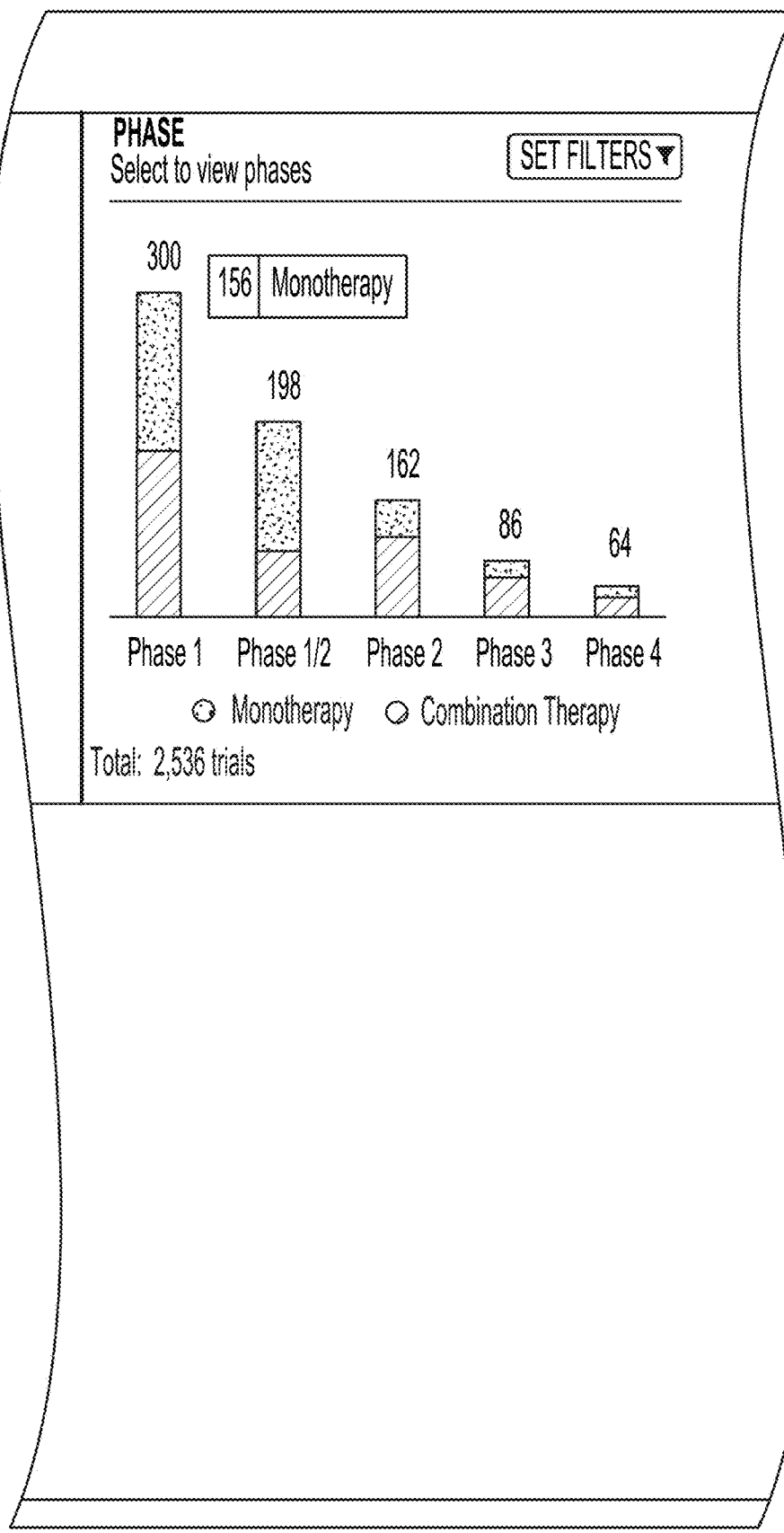
Figure 10C:
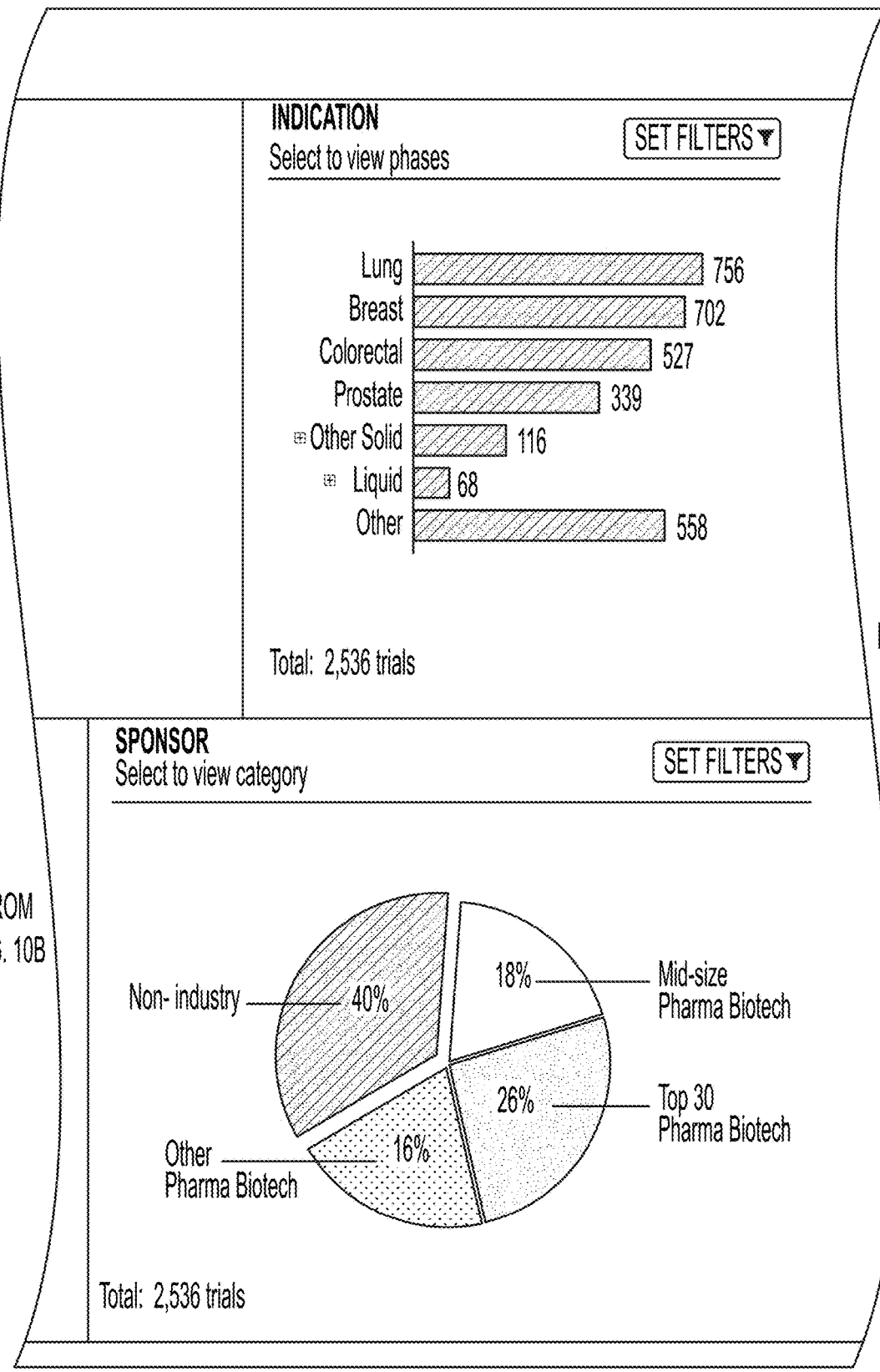
Figure 10D:
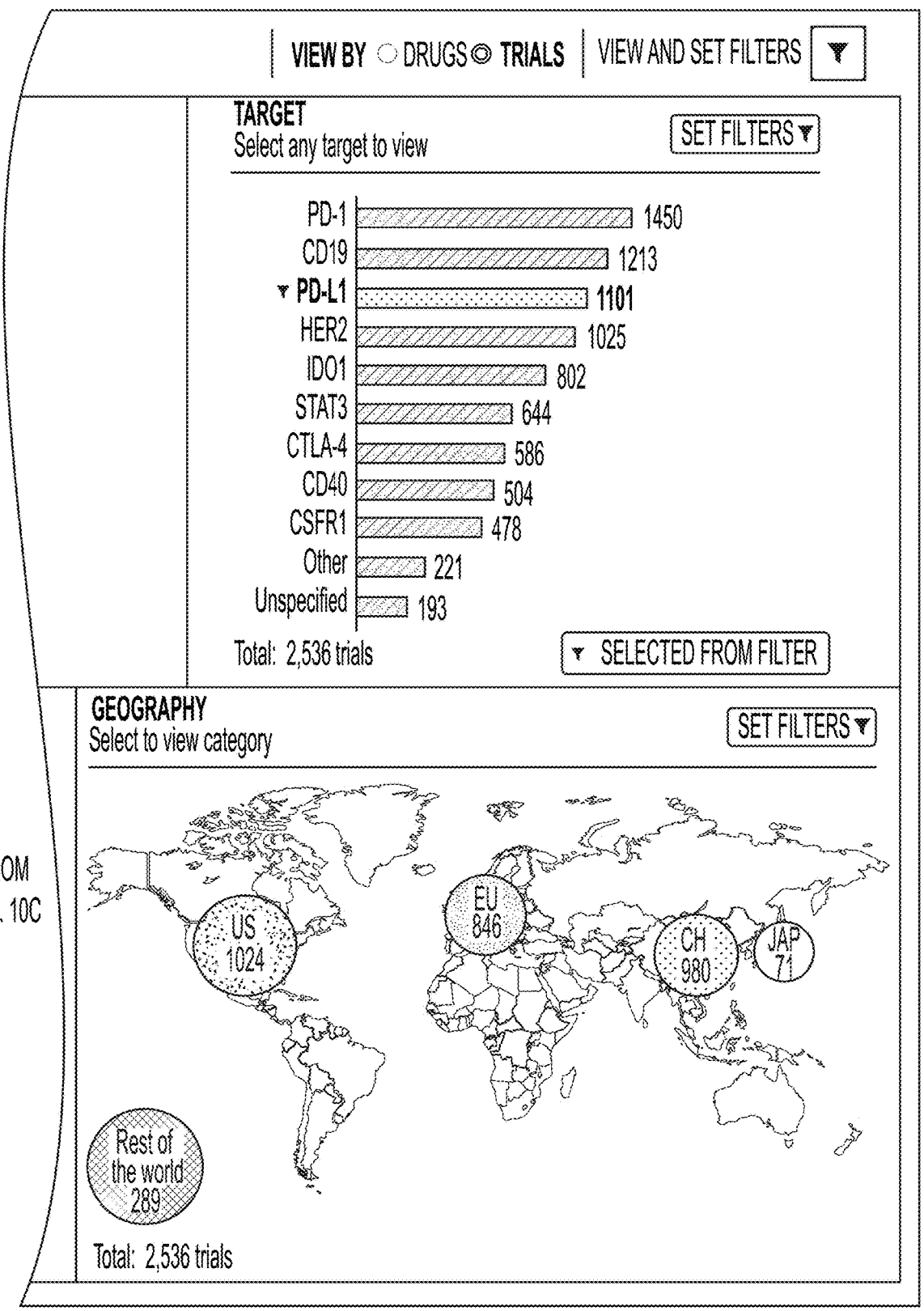

FIGS. 9A-9B an example user interface showing drug details according to some embodiments. As shown, user interface may permit the user to view detail about drugs (e.g., marketed drugs) along with their indications within a single interface.

FIGS. 10A-10D show an example user interface showing trial details according to some embodiments. As discussed above, user may be permitted to select information based on drugs or trials, and in a trials view, the user may perform similar filters in the various categories (e.g., phase, indications, targets, molecule types, sponsor, and geography).

Figure 11A:
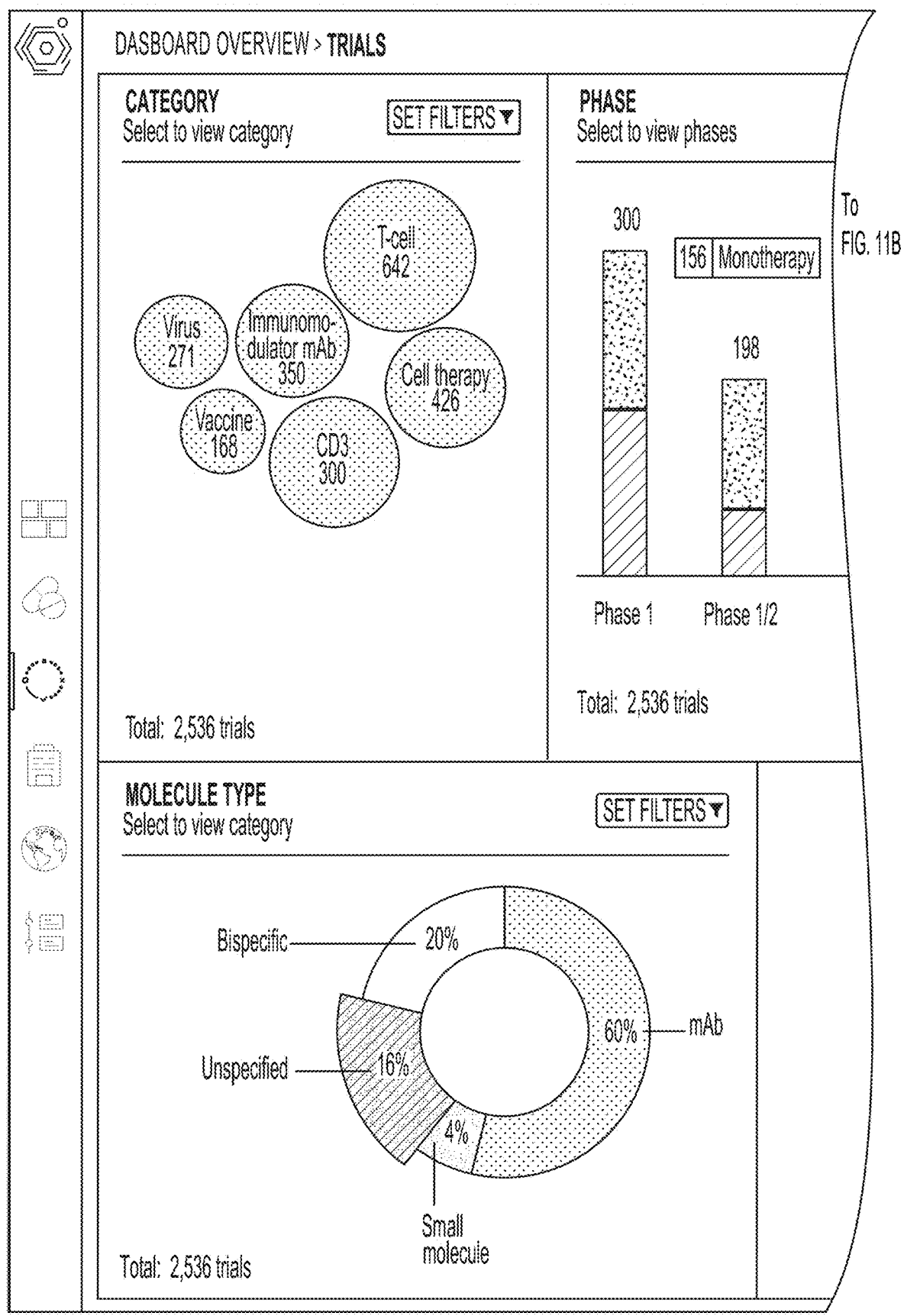
Figure 11B:
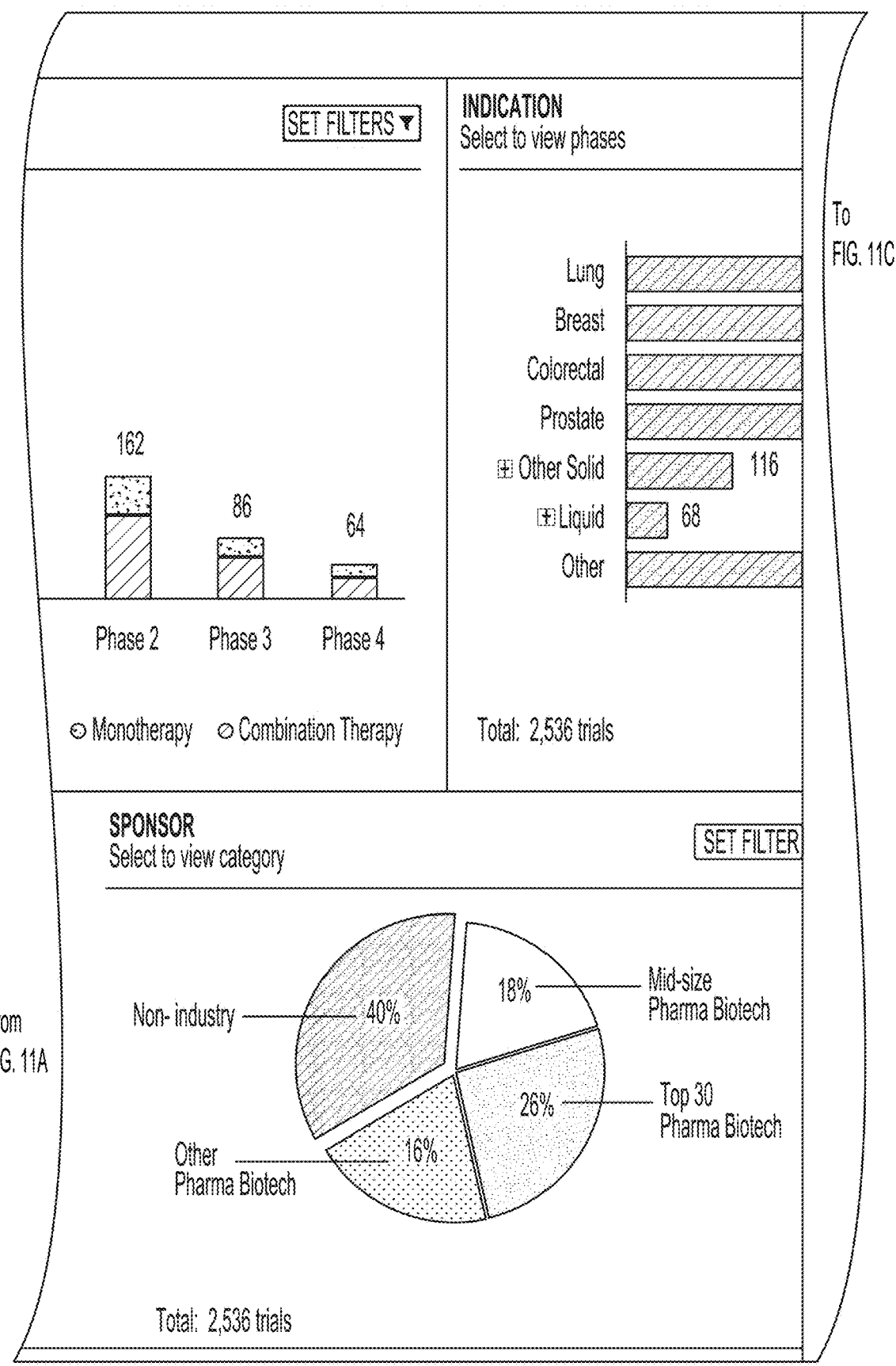

FIGS. 11A-11C show an example user interface showing the use of filters according to some embodiments. For example, within a trials section of the dashboard, the user may be provided one or more controls that permit the user to filter information within the interface. So, for example, the user may be permitted to selectively change the filters associated with each of the various views such as category, phase, indication, target, molecule type, sponsor, geography, or any other type of view.

Figure 12A:
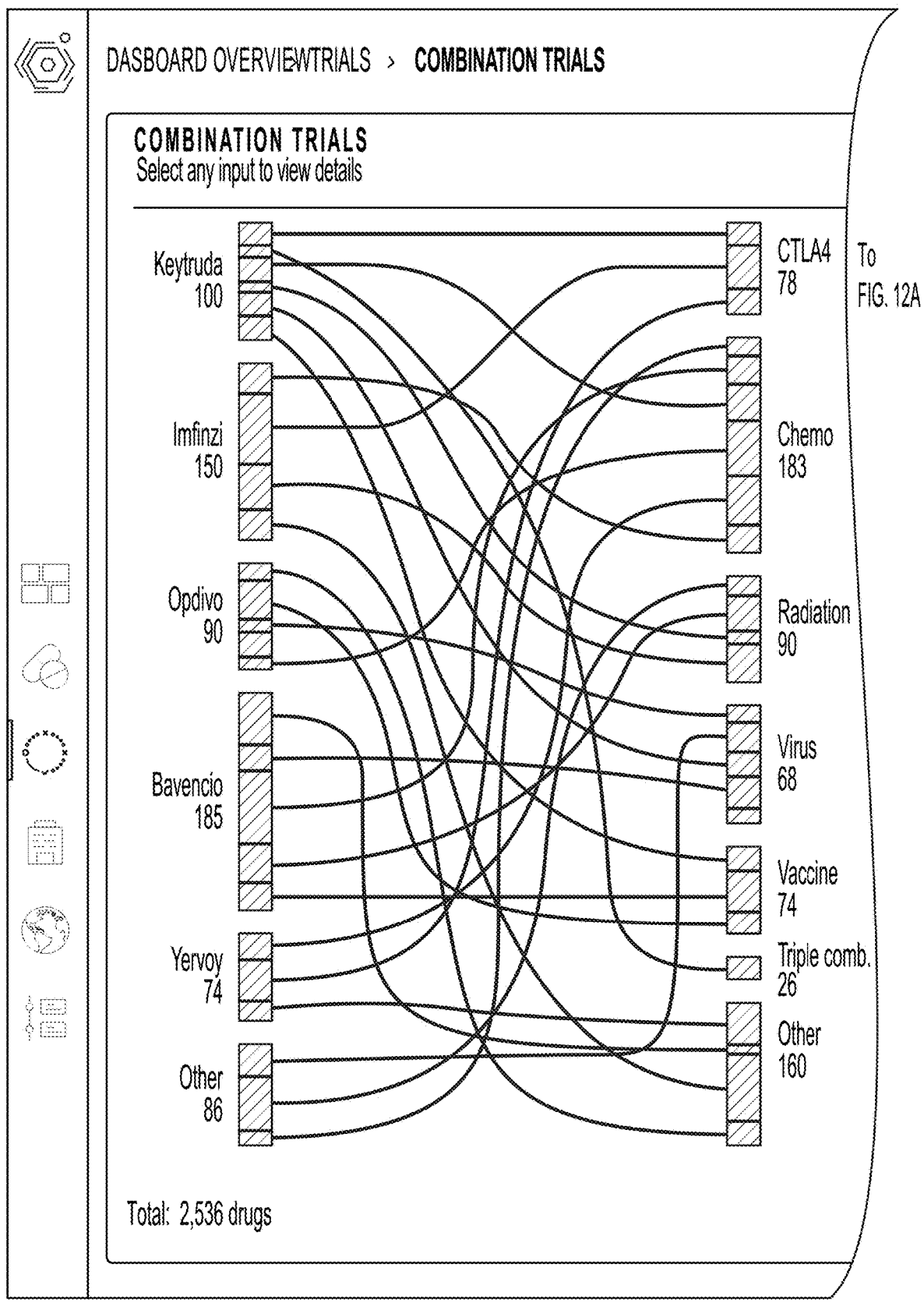
FIGS. 12A-12B show an example user interface showing combination trial information according to some embodiments.
Figure 12B:
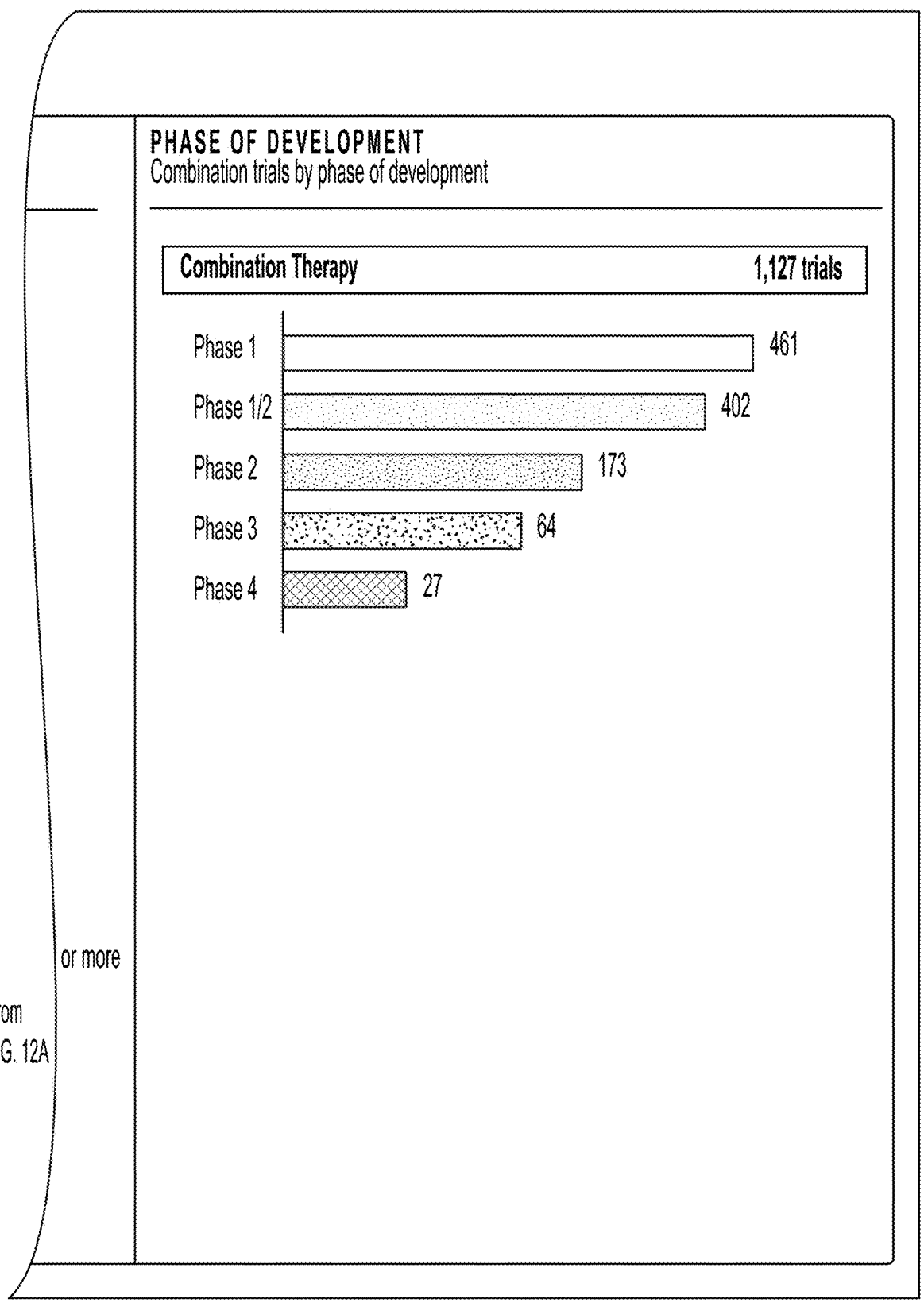
Figure 13A:
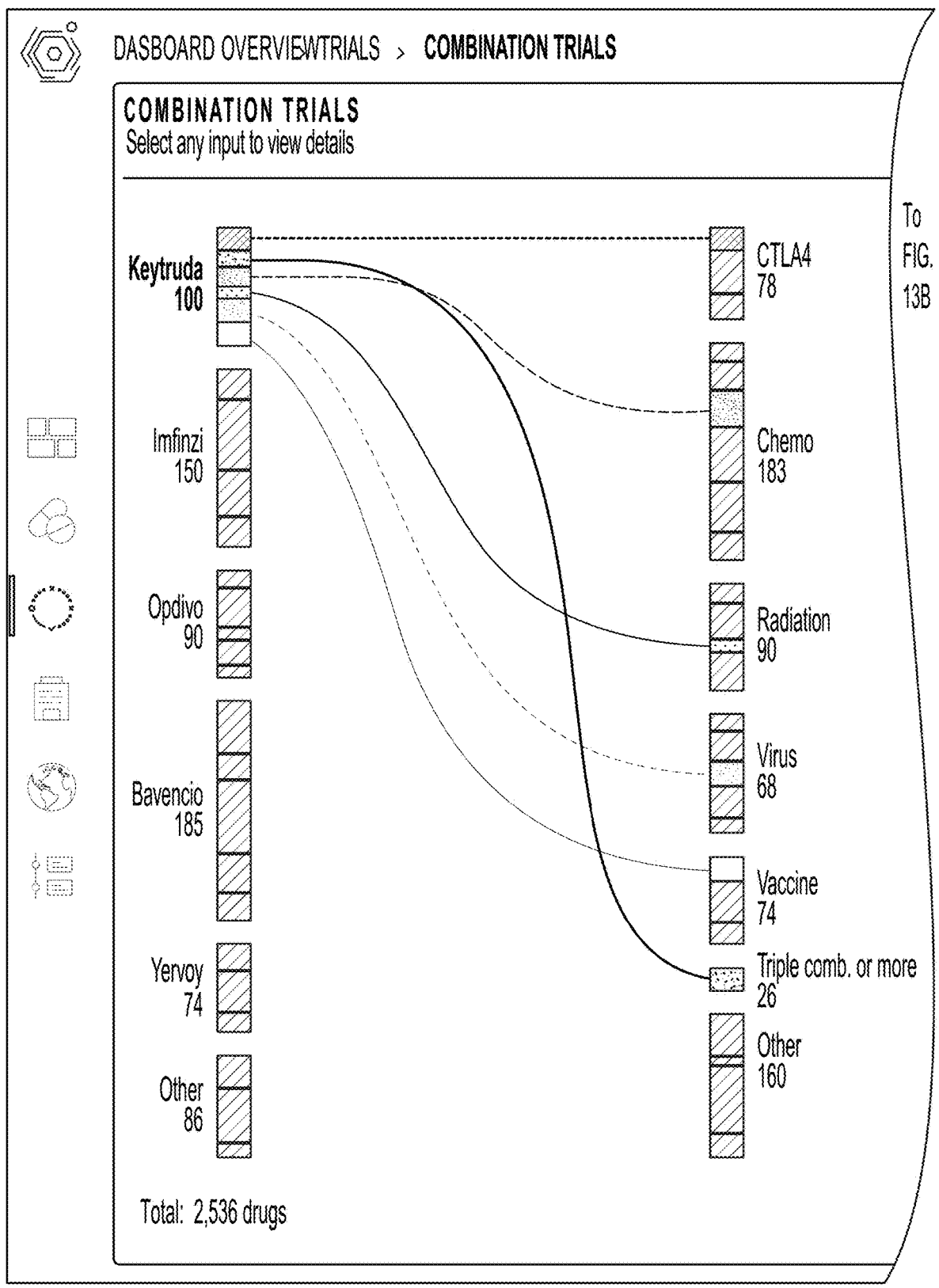
FIGS. 13A-13B show an example user interface showing combination trial information when a particular drug is selected according to some embodiments.
Figure 13B:
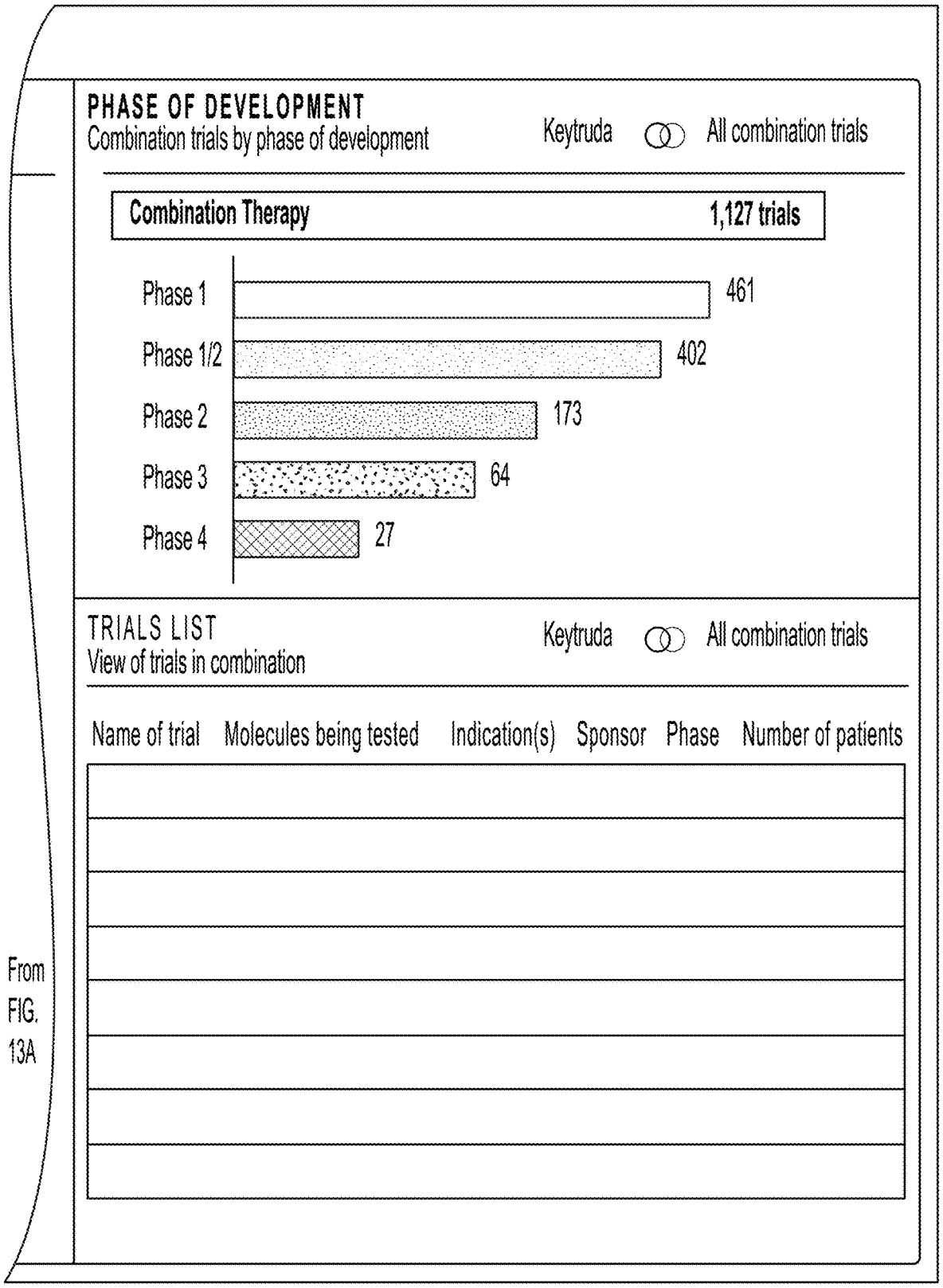
Figure 14A:
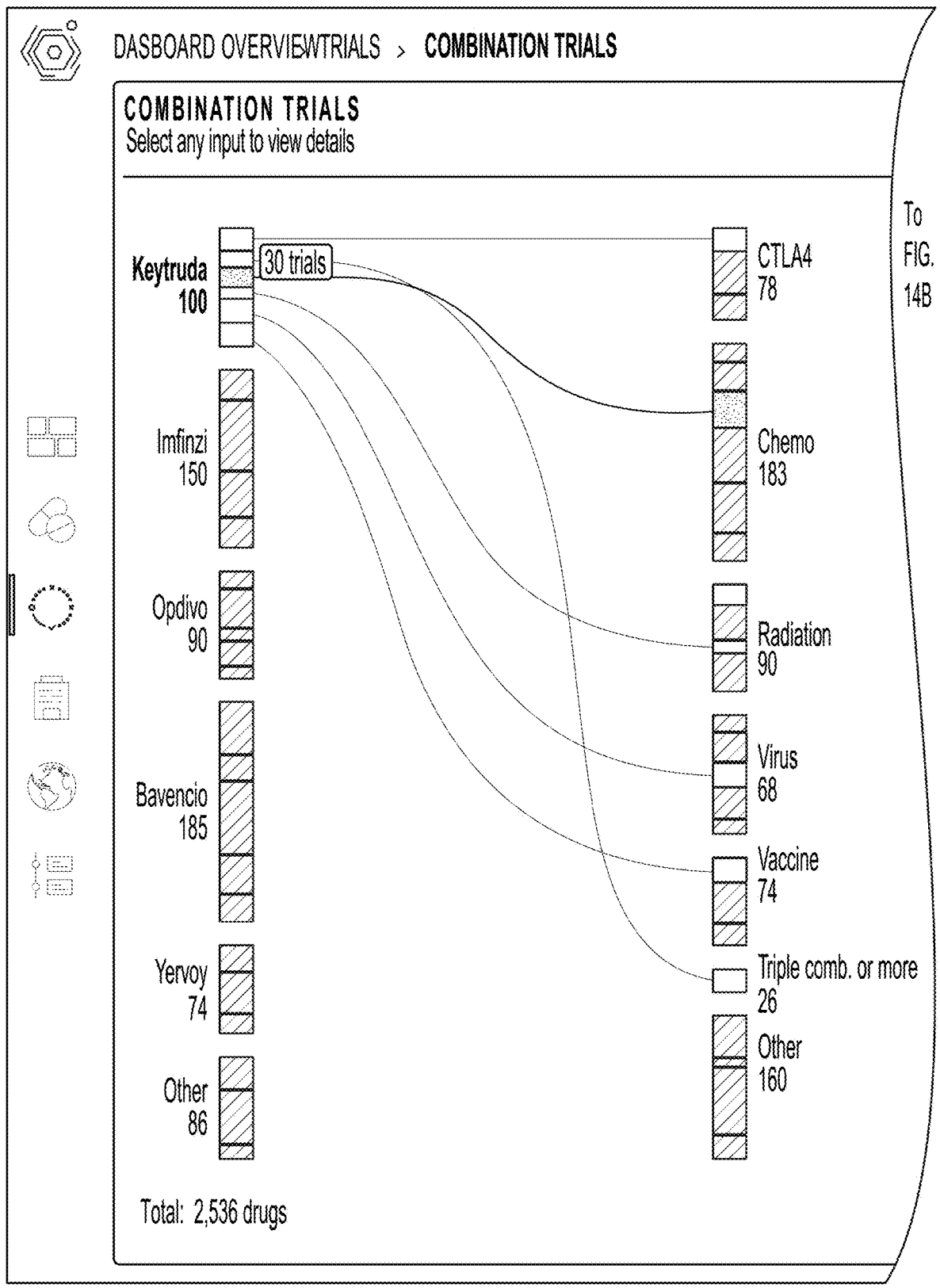
FIGS. 14A-14B show an example user interface showing combination trial information when a particular trial type is selected according to some embodiments.
Figure 14B:
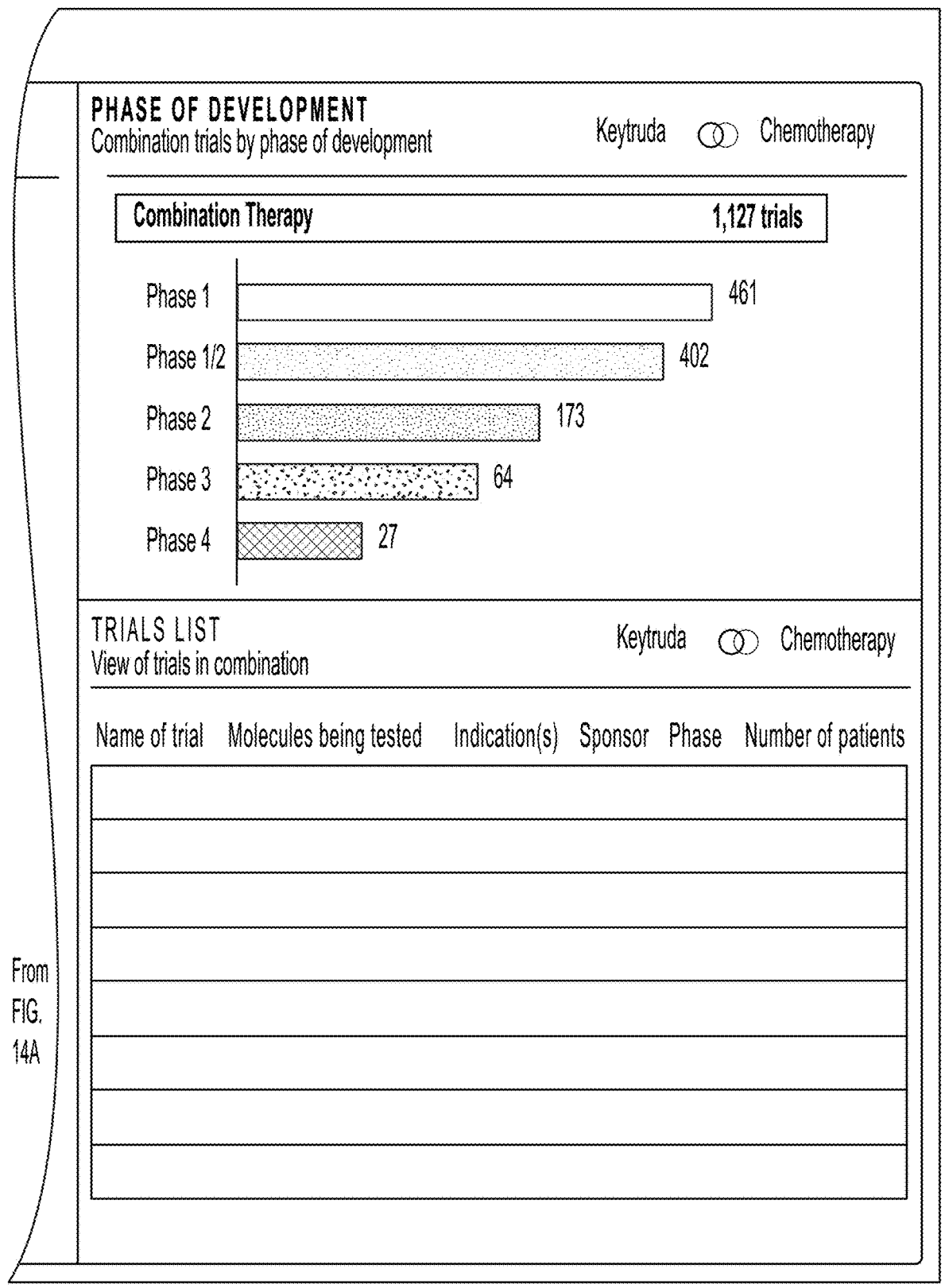
Figure 15A:
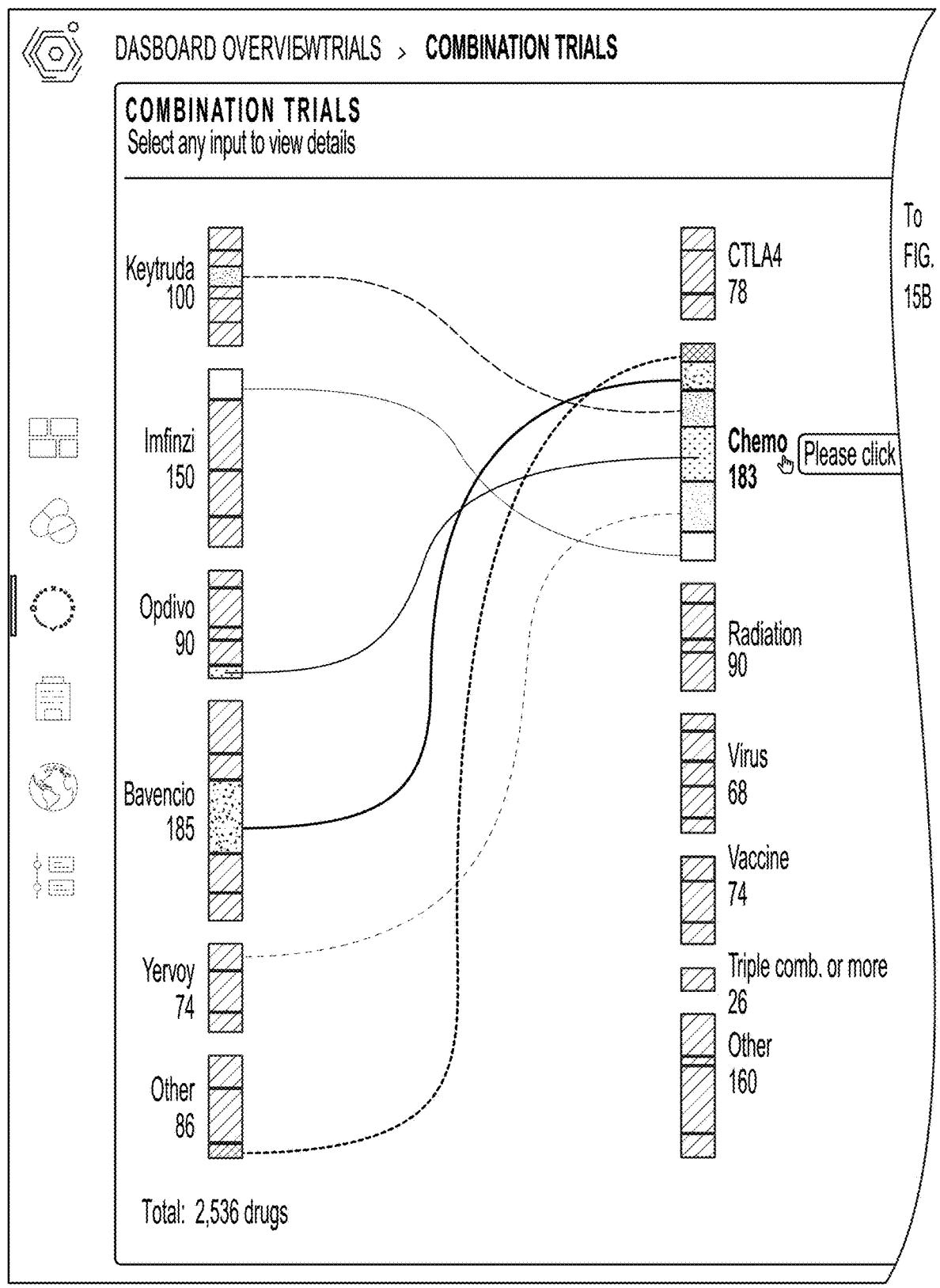
FIGS. 15A-15B show an example user interface showing combination trial information when a particular treatment type is selected according to some embodiments.
Figure 15B:
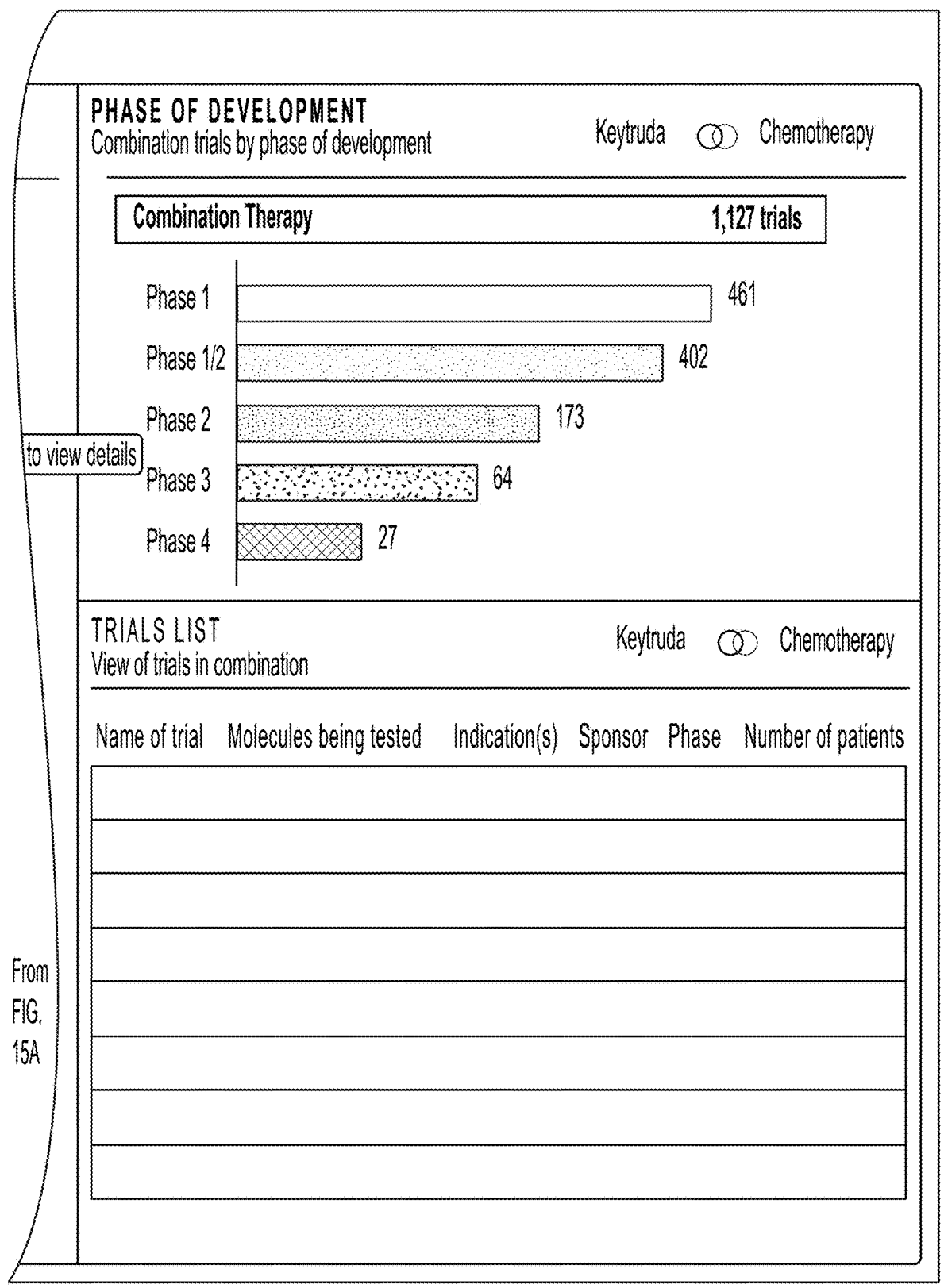

FIGS. 12A-12B show an example user interface showing combination trial information according to some embodiments. For example, within the interface, there may be presented a view that links particular drugs to other interventions which this particular drug is being (or has been) tested in combination with. Because the information is provided graphically in this manner, it is easily viewable to determine the relationship between specific drugs and other combination therapies. For example, FIGS. 13A-B show an example user interface showing combination trial information when a particular drug is selected according to some embodiments. As shown, the drug "Keytruda" is shown, and the view is updated to show the combination of therapy associated with particular trials. In this way, the user may more quickly visualize clinical trial data. In another example, FIGS. 14A-14B show an example user interface showing combination trial information when a particular trial type is selected according to some embodiments. For example, a particular trial type (e.g., chemo) is selected showing the number of trials. Further, within each of these views, there may include more detailed list of trial information that could be located more easily by a user. Conversely, FIGS. 15A-15B show an example user interface showing combination trial information when a particular treatment type is selected according to some embodiments. That is, by selecting a particular treatment, each of the related drugs involved in combination trials with this particular treatment may be more easily located.

Figure 16A:
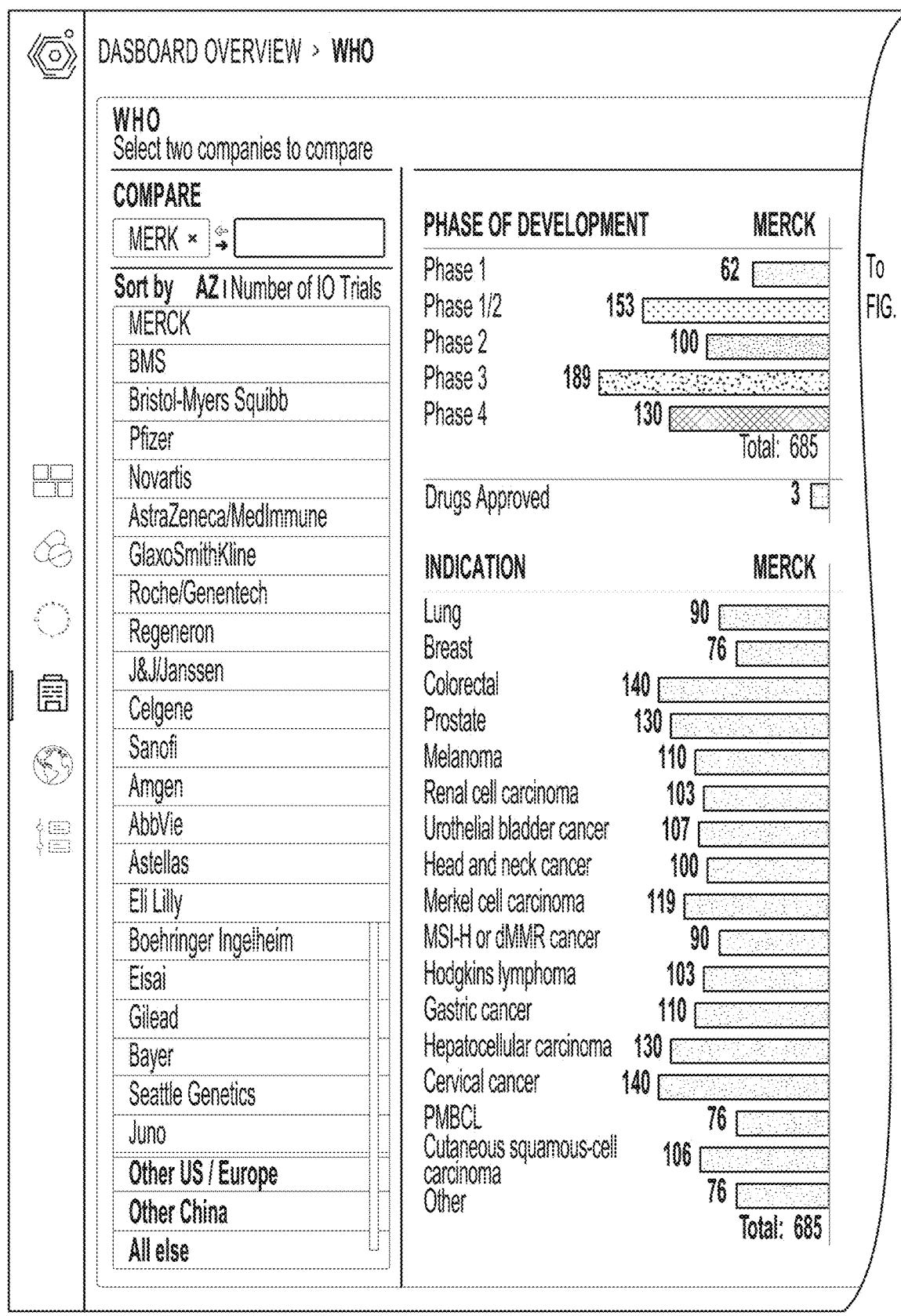
FIGS. 16A-16B show an example user interface showing controls that permit the user to search for clinical data relating to selected companies according to some embodiments.
Figure 16B:
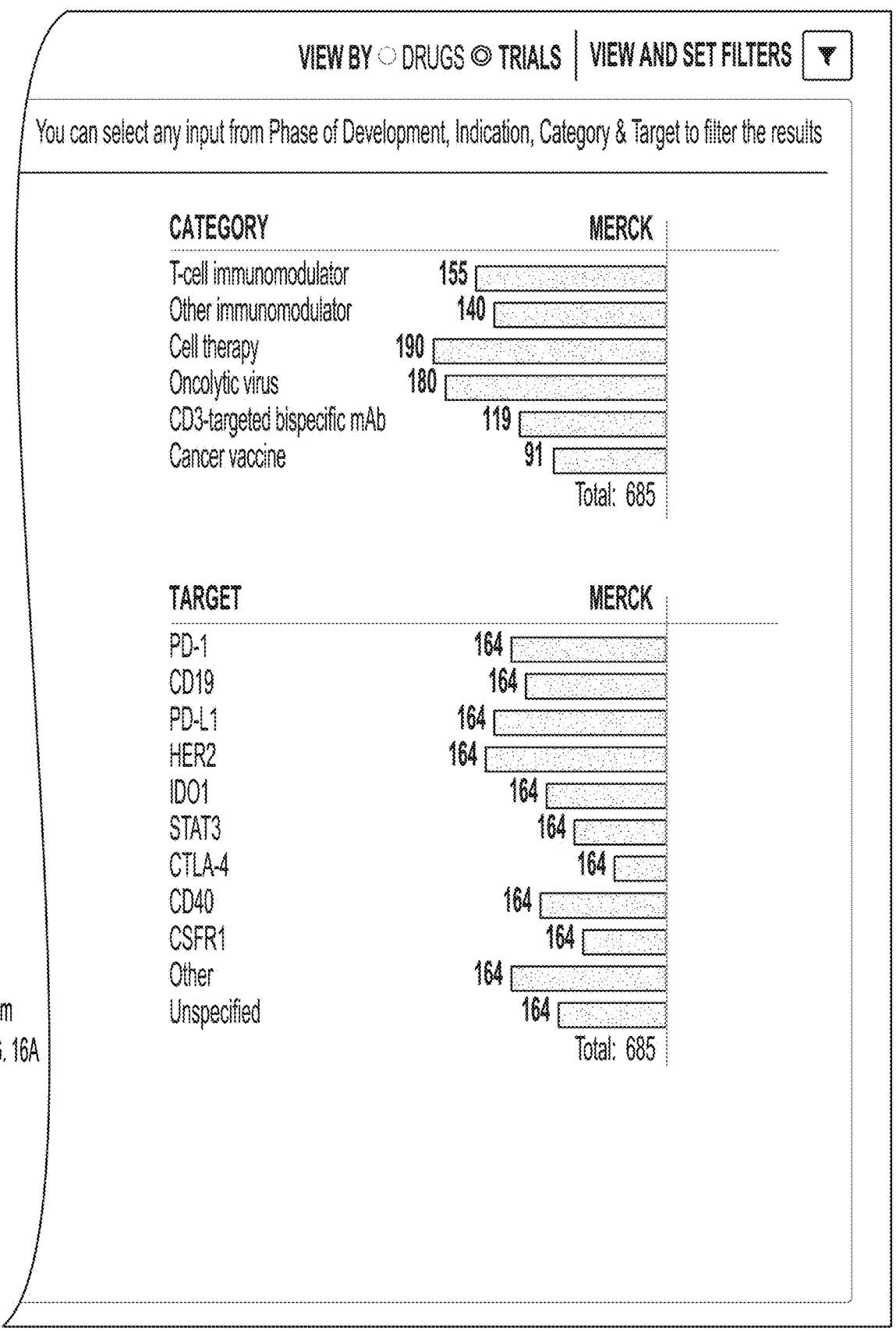
Figure 17A:
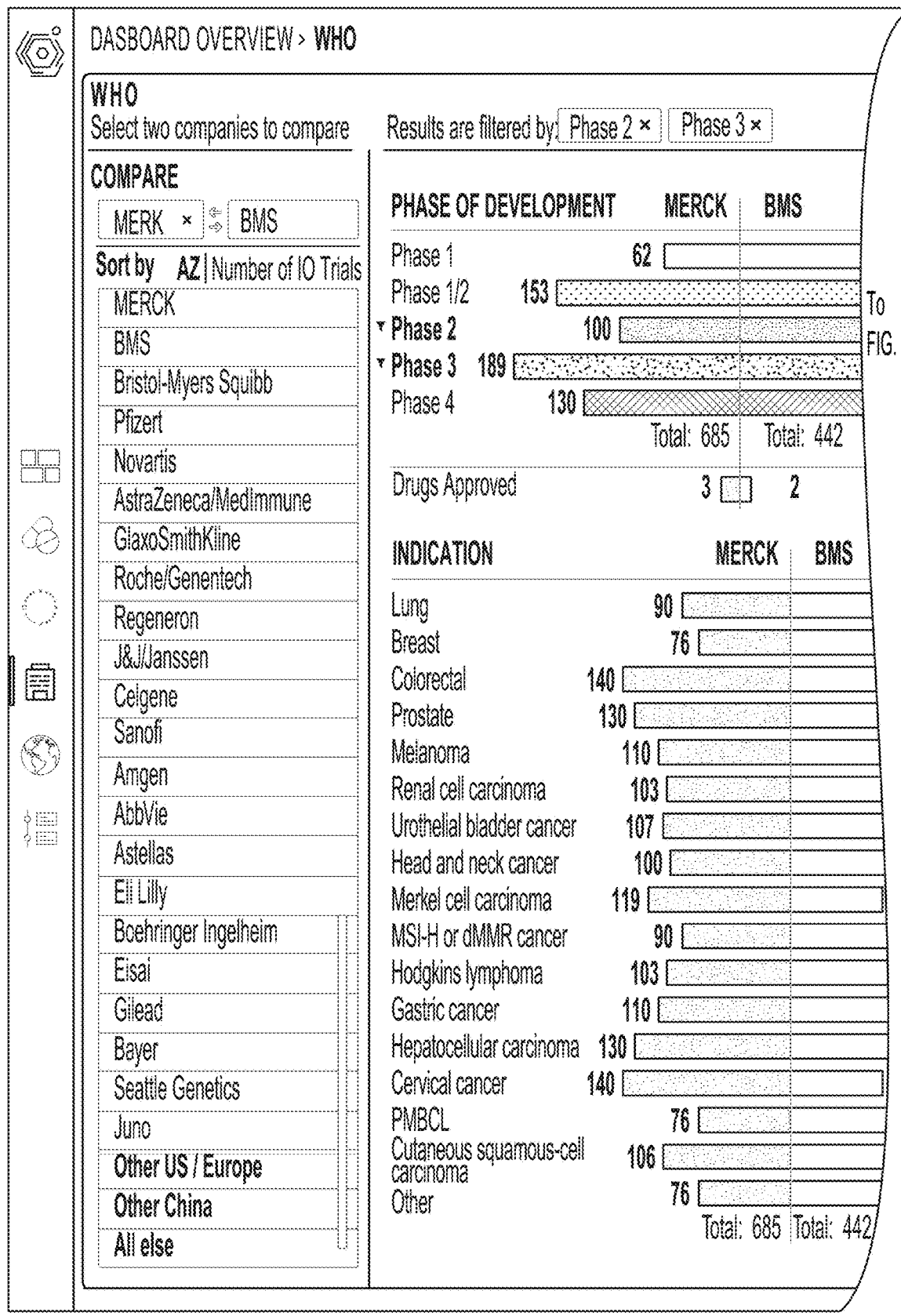
FIGS. 17A-17B show an example user interface showing controls that permit the user to compare clinical data relating to selected companies to be compared according to some embodiments.
Figure 17B:
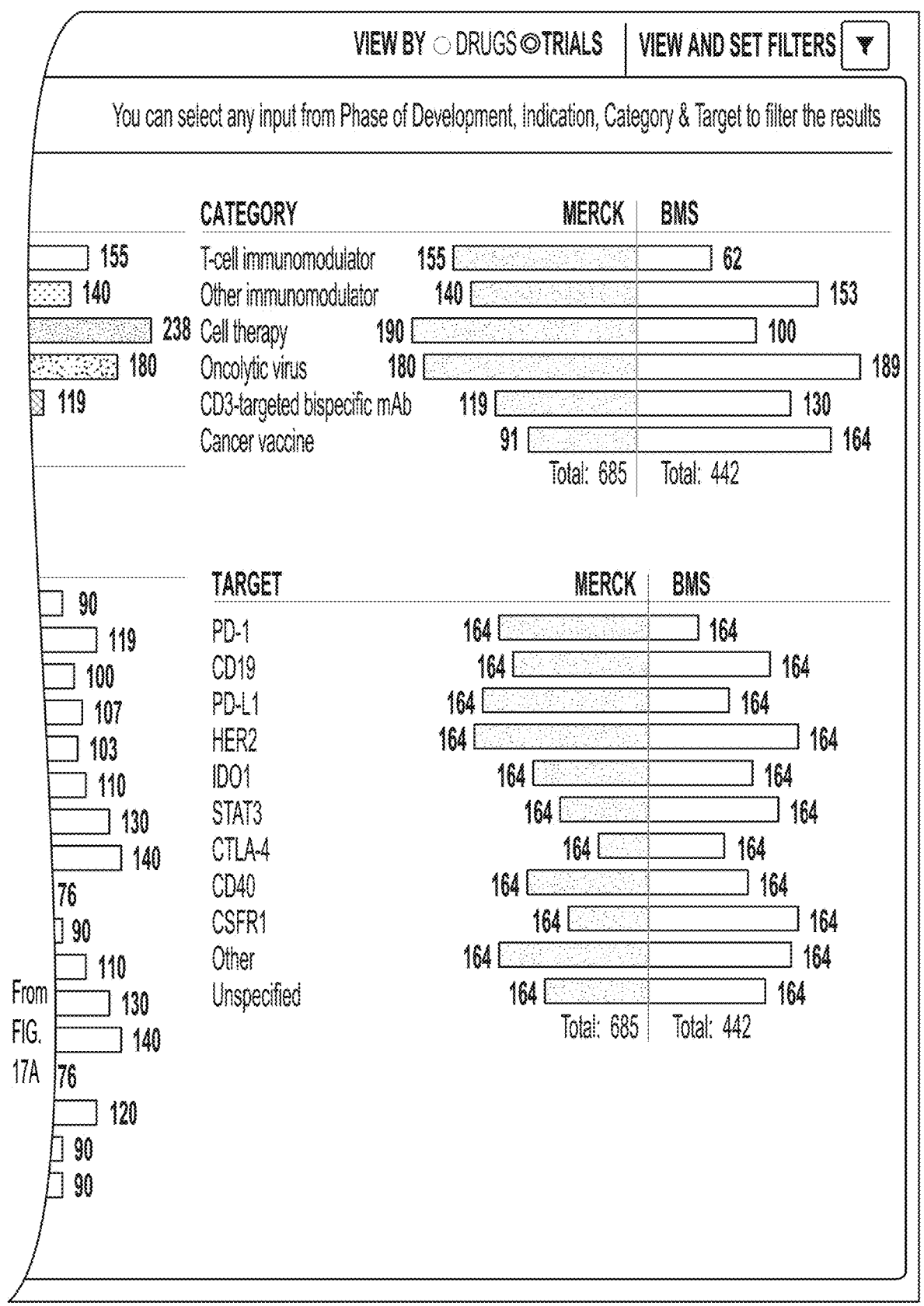

FIGS. 16A-16B show an example user interface showing controls that permit the user to search for clinical data relating to selected companies according to some embodiments. As discussed above, users may be permitted to locate information within a "who" interface. In a more detailed view, the user may be permitted to selectively locate information associated with one or more particular companies. In another example, FIGS. 17A-17B show an example user interface showing controls that permit the user to compare clinical data relating to selected companies to be compared according to some embodiments. In this view, the user enters "MERCK" and "BMS" in order to compare clinical trial data between both of these companies within a consolidated view. Further, results may be filtered in other dimensions such as by phase 2 and phase 3 trials.

Figure 18A:
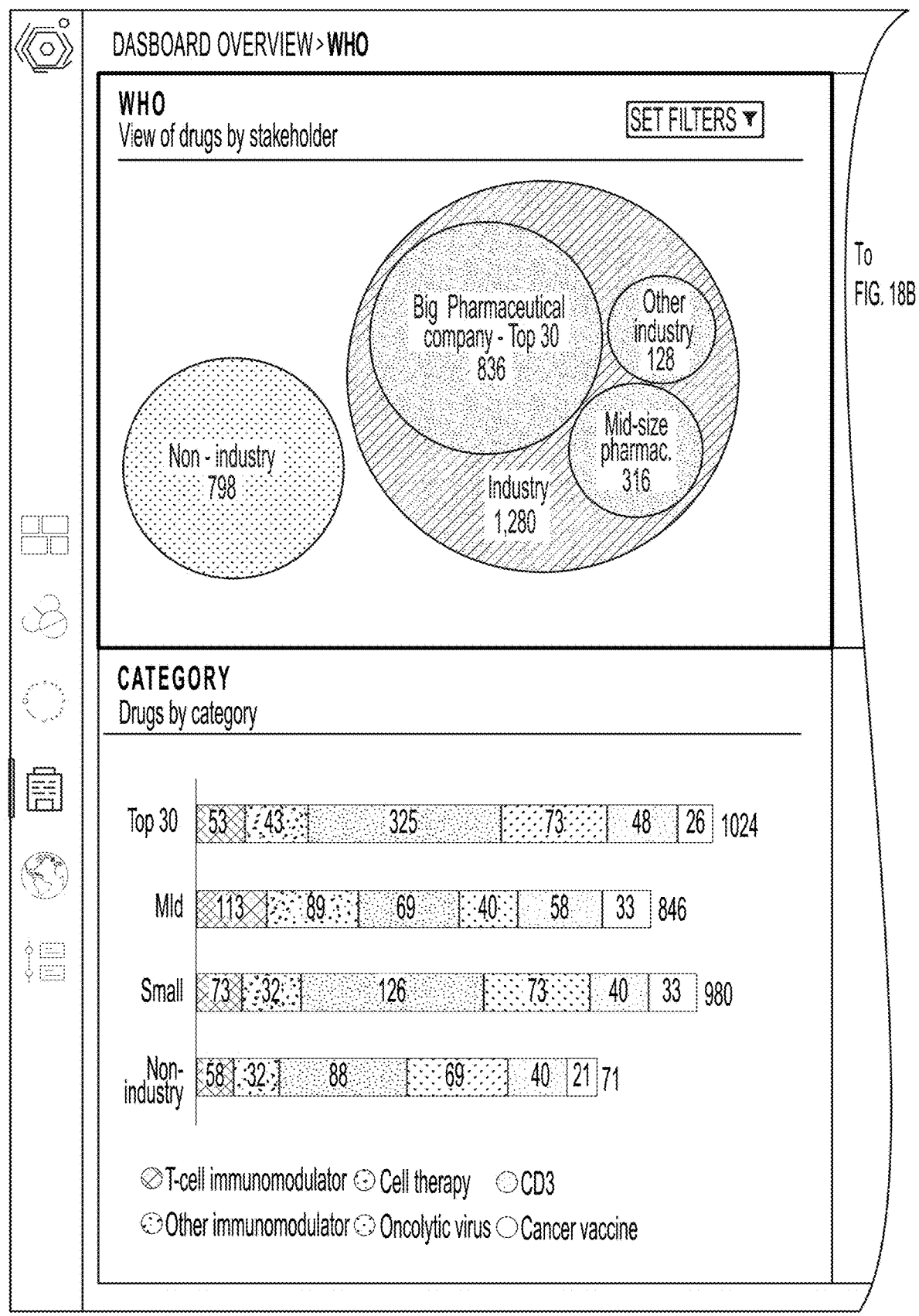
Figure 18B:
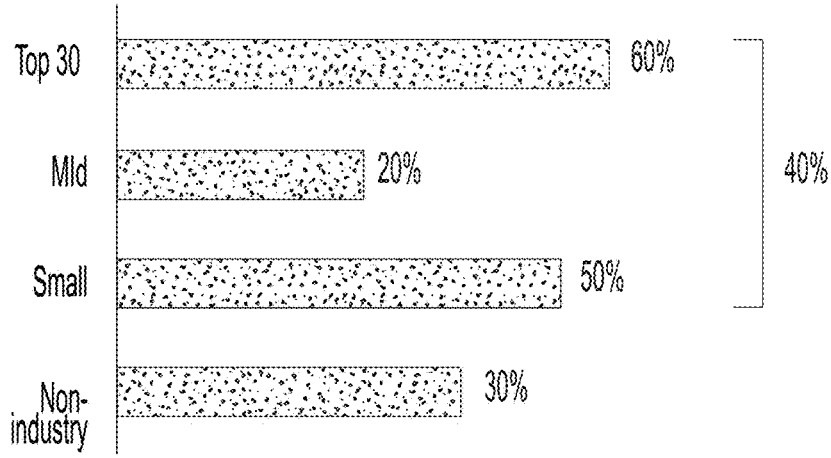
Figure 19A:
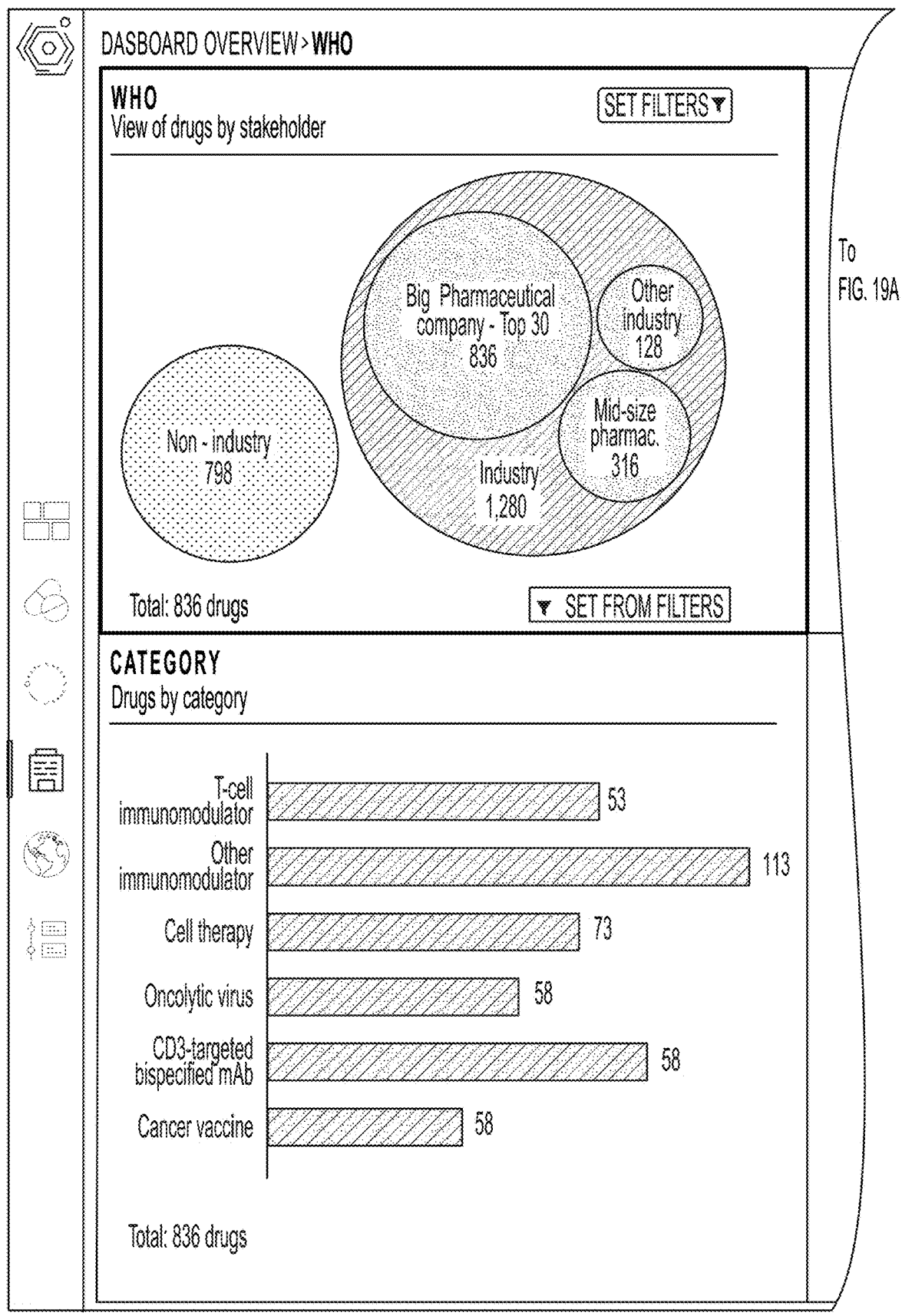
FIGS. 19A-19C show an example user interface an example dashboard view that provides content when a particular stakeholder is selected according to some embodiments.
Figure 19B:
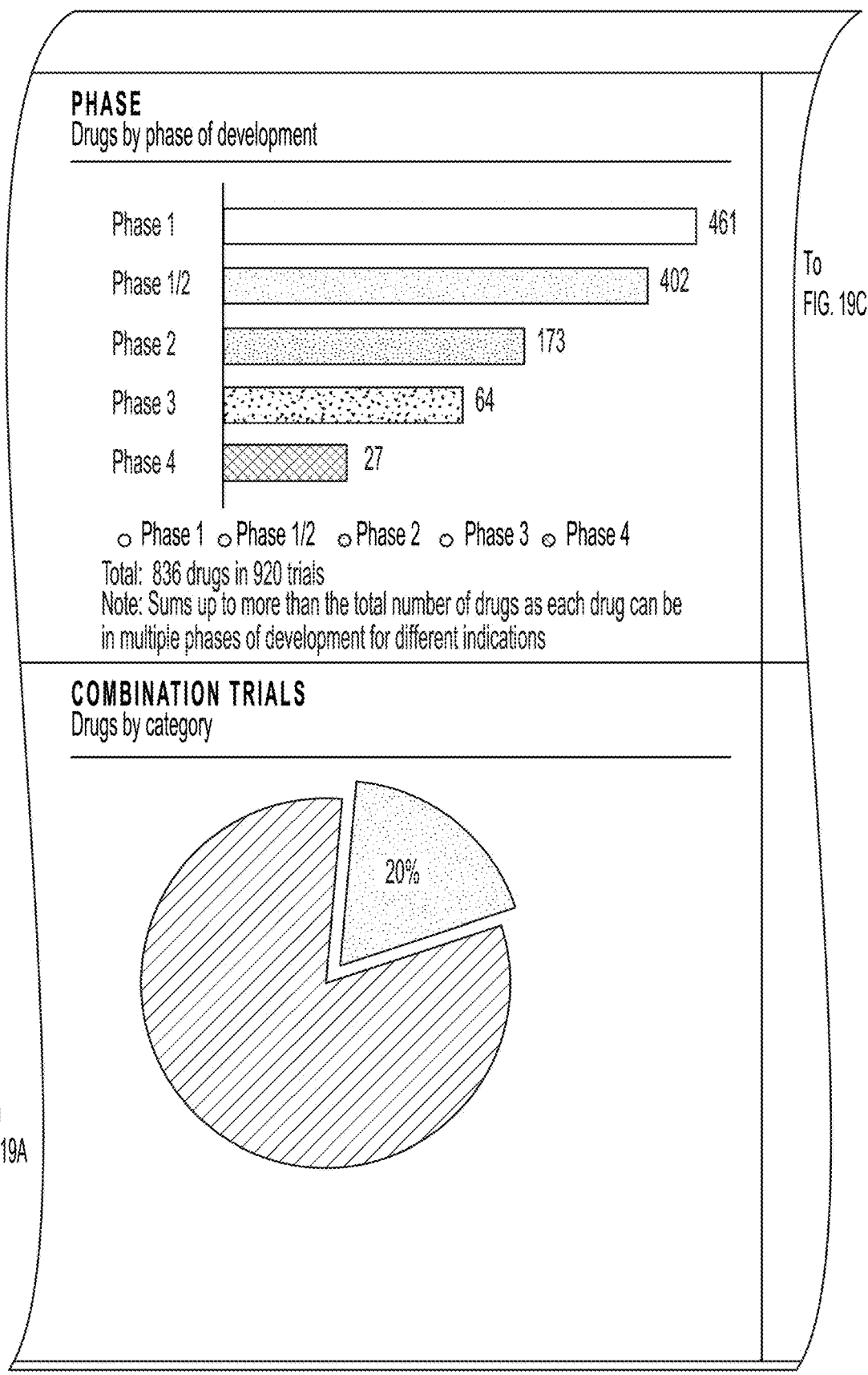
Figure 19C:
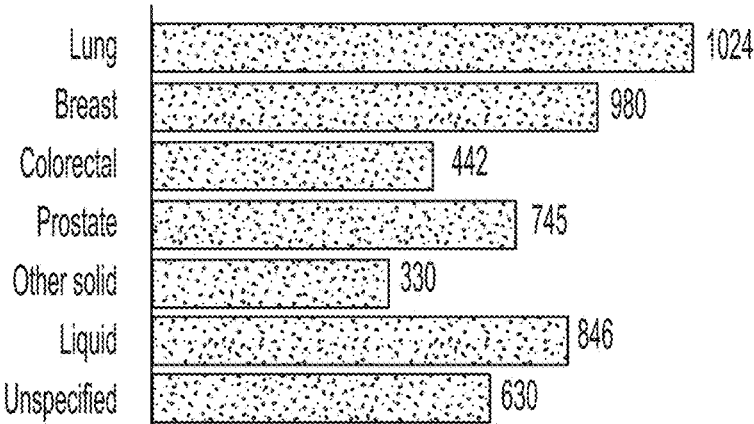
Figure 19C:
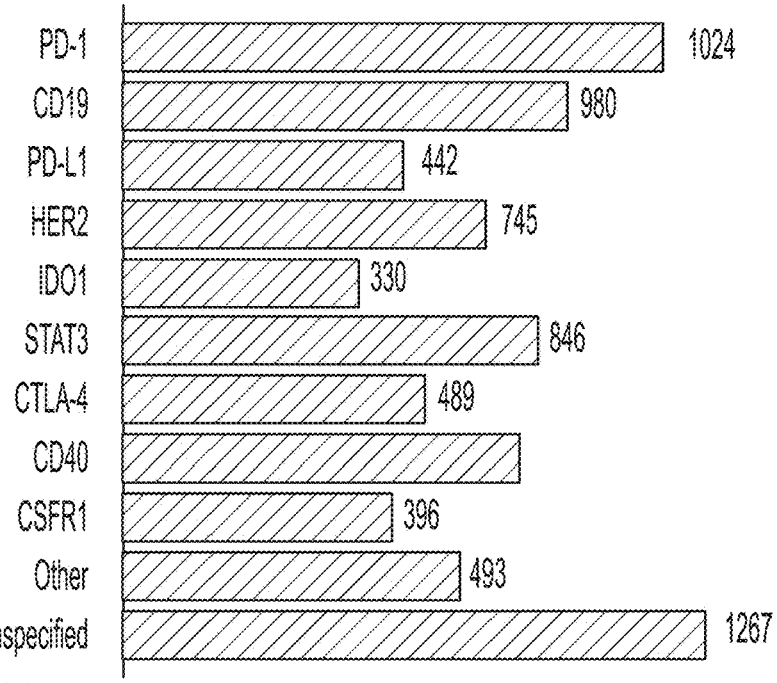

FIGS. 18A-18C show an example user interface an example dashboard view that provides content based on the stakeholder according to some embodiments. In FIGS. 19A-19C include an example user interface that shows an example dashboard view that provides content when a particular stakeholder type (e.g., "Big Pharmaceutical Company") is selected according to some embodiments.

Figure 20A:
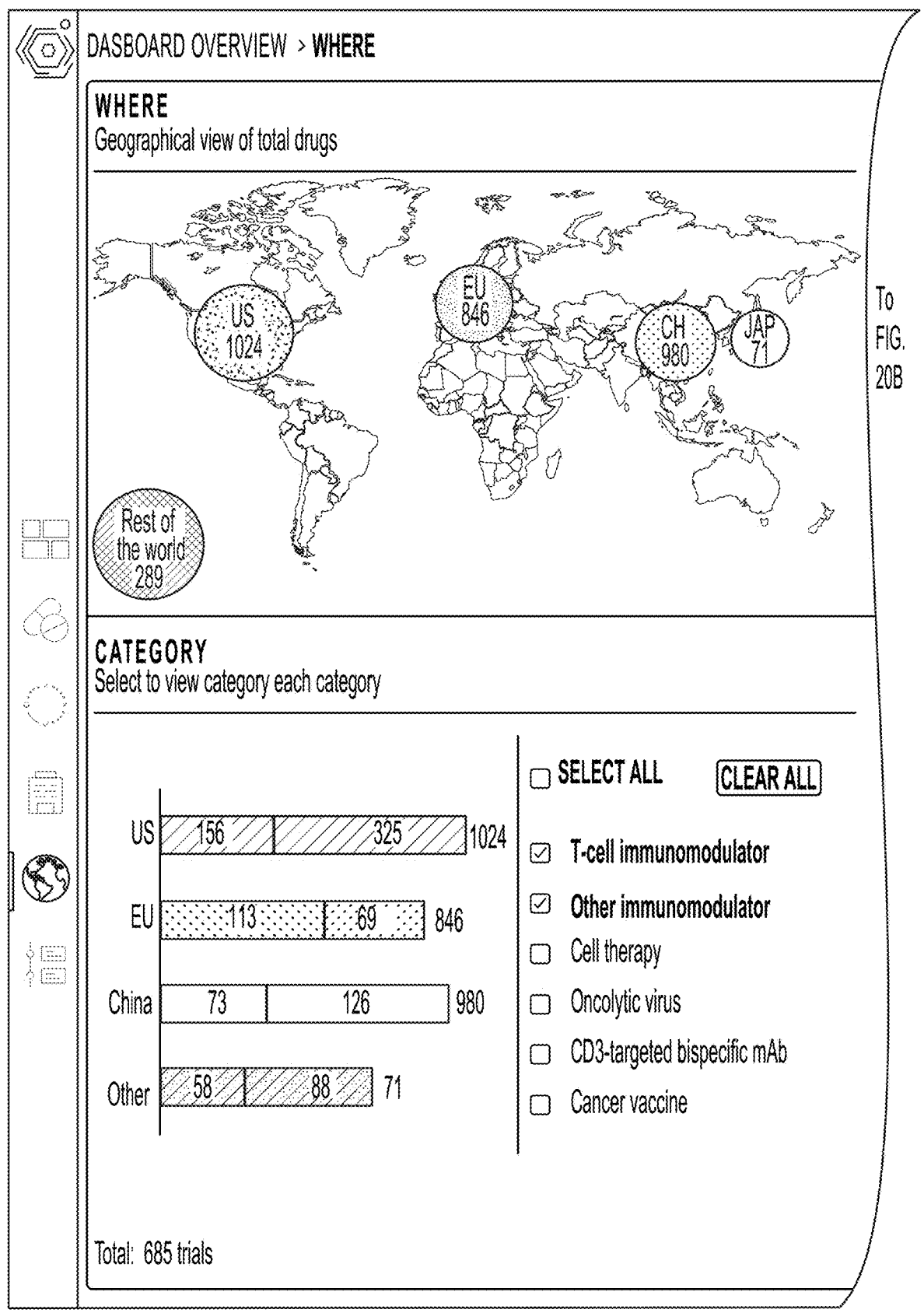
FIGS. 20A-20B show an example user interface showing another example dashboard view identifying where the clinical trials are being conducted according to some embodiments.
Figure 20B:
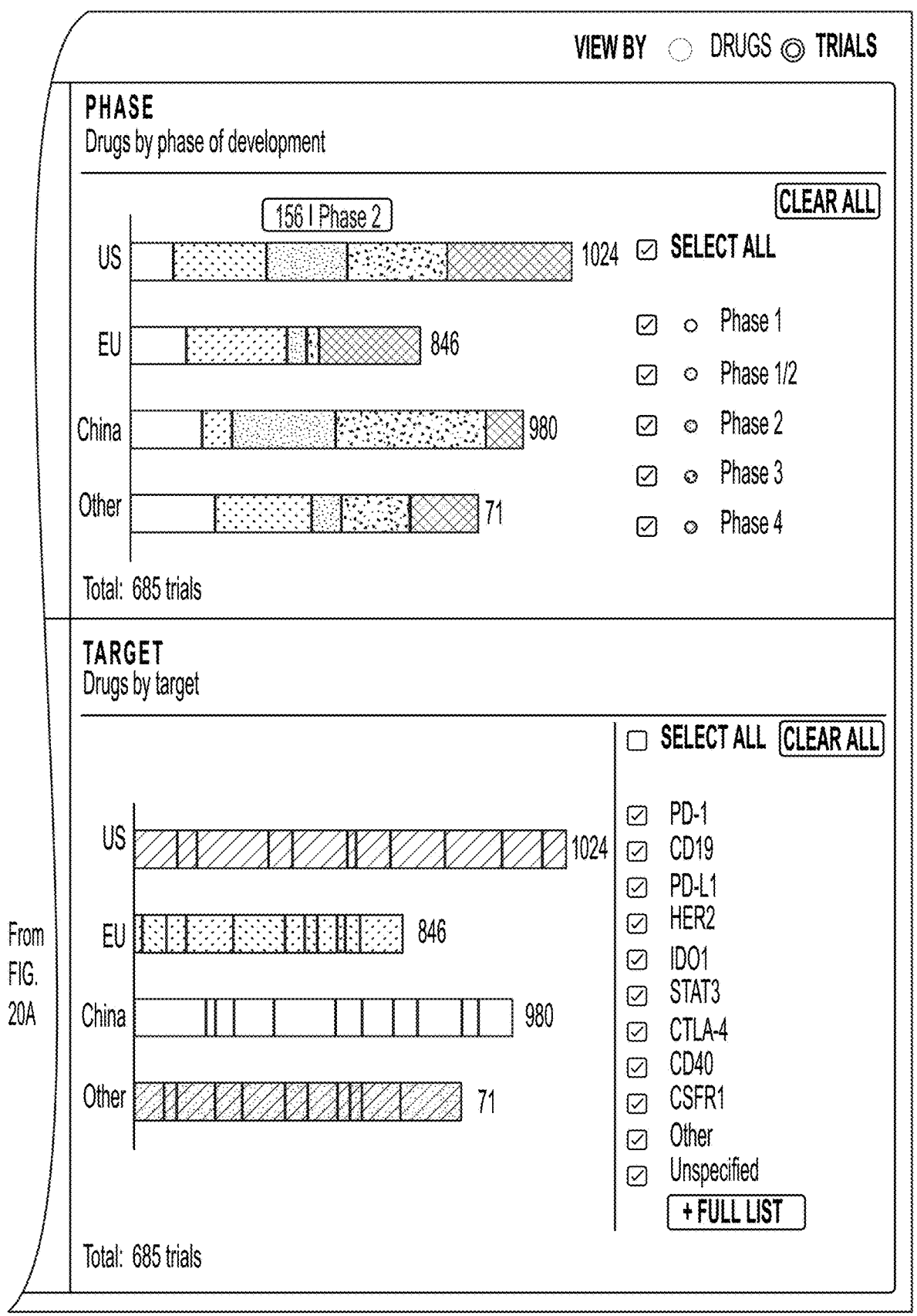
Figure 21A:
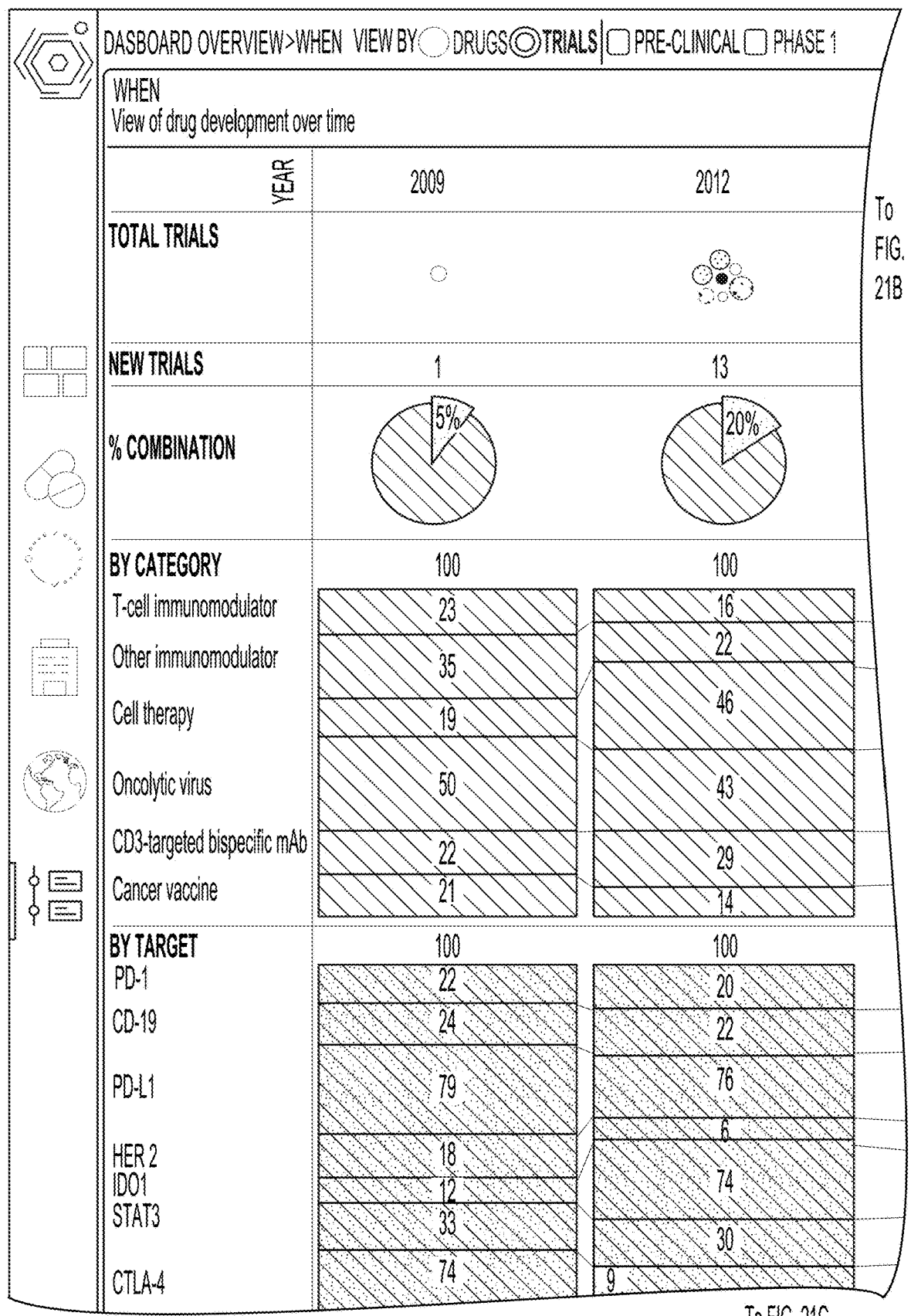
FIGS. 21A-21D show an example user interface showing another example dashboard view according to some embodiments.
Figure 21B:
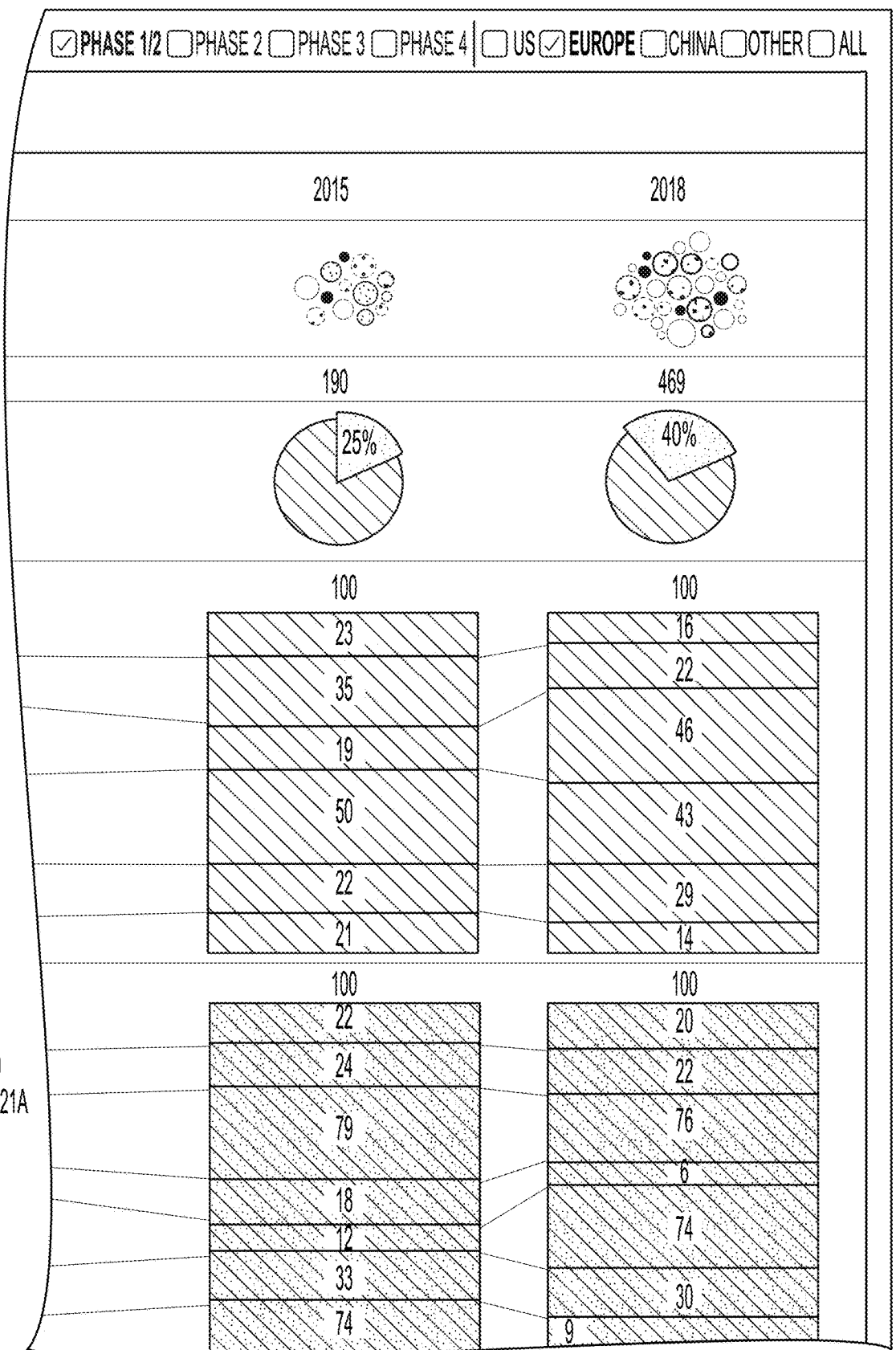
Figure 21C:
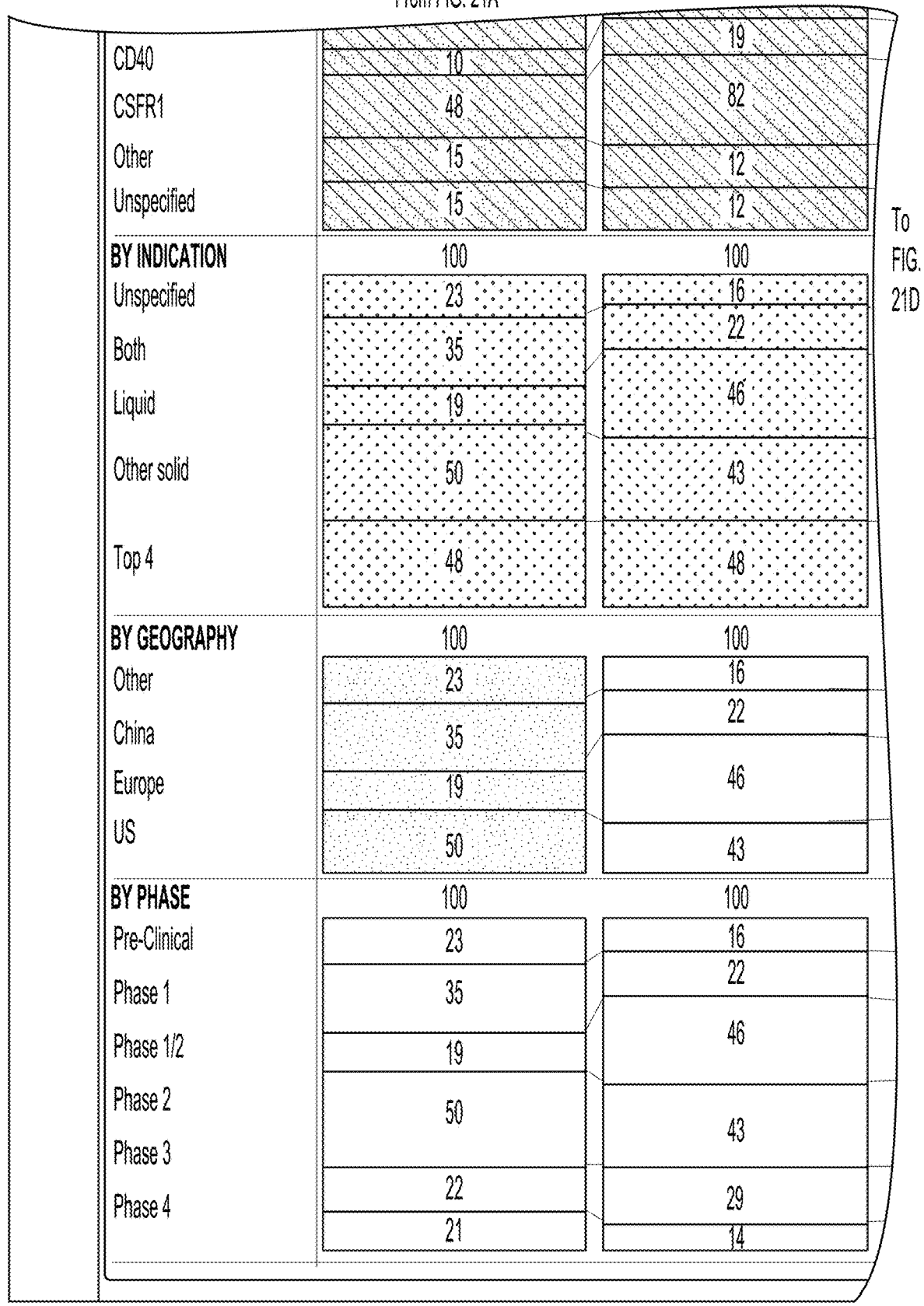
Figure 21D:
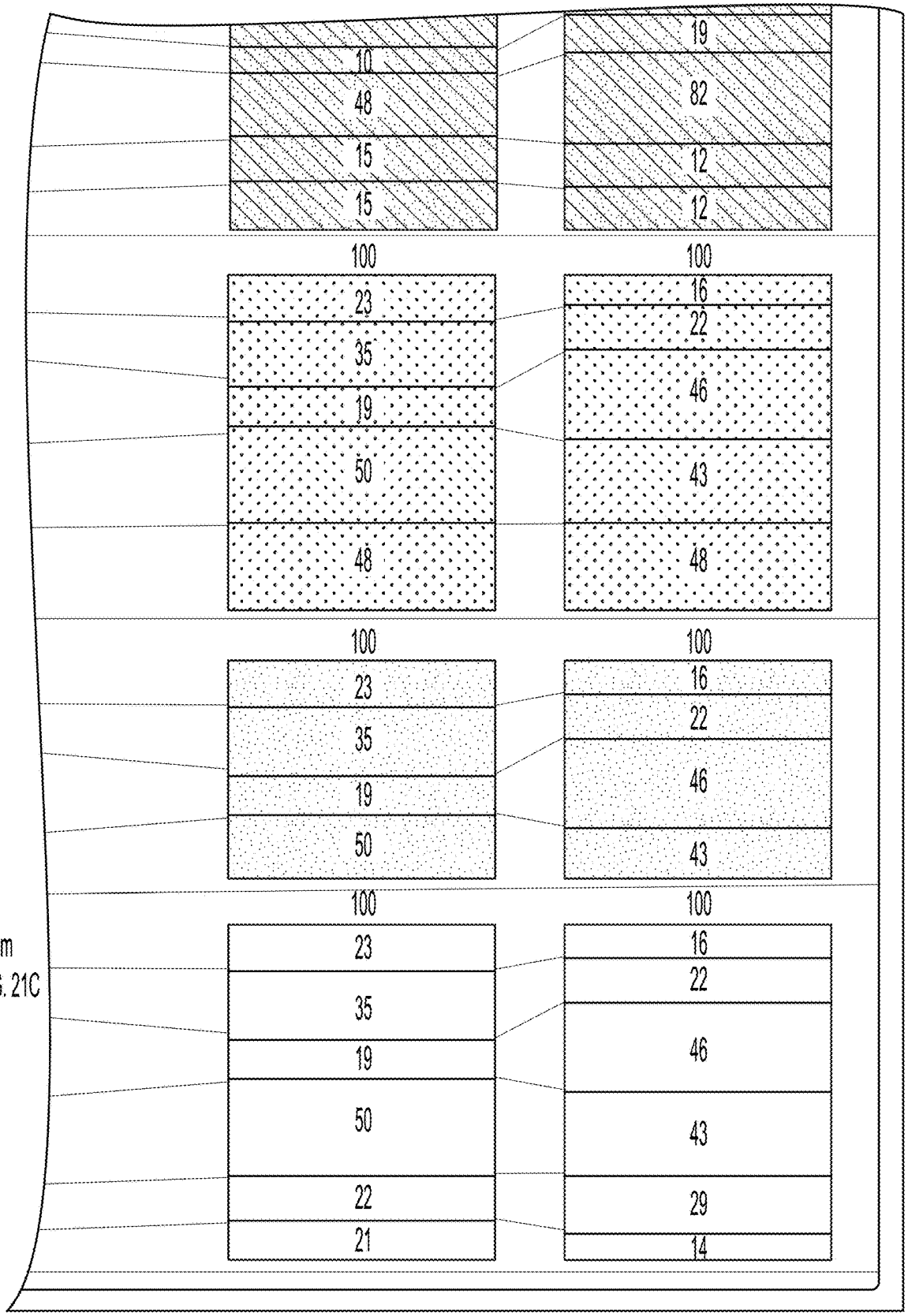

FIGS. 20A-20B show—an example user interface showing another example dashboard view identifying where the clinical trials are being conducted according to some embodiments; and FIGS. 21A-21D show an example user interface showing another example dashboard view according to some embodiments.

Techniques operating according to the principles described herein may be implemented in any suitable manner. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

Further, some techniques described above comprise acts of storing information (e.g., data and/or instructions) in certain ways for use by these techniques. In some implementations of these techniques—such as implementations where the techniques are implemented as computer-executable instructions—the information may be encoded on a computer-readable storage media. Where specific structures are described herein as advantageous formats in which to store this information, these structures may be used to impart a physical organization of the information when encoded on the storage medium. These advantageous structures may then provide functionality to the storage medium by affecting operations of one or more processors interacting with the information; for example, by increasing the efficiency of computer operations performed by the processor(s).

In some, but not all, implementations in which the techniques may be embodied as computer-executable instructions, these instructions may be executed on one or more suitable computing device(s) operating in any suitable computer system, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

A computing device may comprise at least one processor, a network adapter, and computer-readable storage media. A computing device may be, for example, a desktop or laptop personal computer, a personal digital assistant (PDA), a smart mobile phone, a server, or any other suitable computing device. A network adapter may be any suitable hardware and/or software to enable the computing device to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media may be adapted to store data to be processed and/or instructions to be executed by processor. The processor enables processing of data and execution of instructions. The data and instructions may be stored on the computer-readable storage media.

A computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

What is claimed is:

1. A system, comprising:
    at least one processor in communication with a memory storing instructions configured to cause the at least one processor to perform:
        storing, in a database, a plurality of sets of data of clinical trials of a plurality of drugs, wherein data for each of the clinical trials in the plurality of sets of data comprises at least:
            a drug of the clinical trial;
            an outcome of the clinical trial for the drug;
            data regarding patients of the clinical trial used to evaluate the drug; and
            at least one of regulatory data associated with the clinical trial, drug molecule characteristics of the drug, and design information of the clinical trial;
        training a plurality of different types of machine learning models using training data of clinical trials of the plurality of drugs from the plurality of sets of data to generate a plurality of trained machine learning models, wherein each of the plurality of different types of machine learning models is trained to take as input a drug of interest and an indication of interest and to generate as output a predicted outcome of a new clinical trial for the drug of interest and the indication of interest;
        testing the plurality of trained machine learning models, comprising executing each trained machine learning model of the plurality of different types of machine learning models on testing data from the plurality of sets of data of clinical trials of the plurality of drugs to determine a prediction of a particular trial outcome and to generate associated performance data for each trained machine learning model;
        selecting, based on the performance data associated with each trained machine learning model, at least one trained machine learning model and an associated type of machine learning model, comprising comparing the performance data associated with each trained machine learning model using an area under the ROC curve (AUC) metric to select the at least one trained machine learning model as performing better than at least one other model of the trained machine learning models;
        executing the at least one trained machine learning model by inputting input data to the trained machine learning model for a particular clinical trial under investigation for an associated particular drug and a particular indication of the particular clinical trial and receiving as output from execution of the at least one trained machine learning model a likelihood that the particular clinical trial associated with the particular drug and the particular indication will result in the particular drug being approved to treat the particular indication;
        displaying, via an interface, to an entity, a measure of the likelihoods;
        displaying, via the interface, a set of parameters for the particular clinical trial under investigation, wherein:
            the set of parameters were used to execute the at least one trained machine learning model for the particular clinical trial under investigation; and
            the set of parameters relate to patients of the particular clinical trial, design information of the particular clinical trial, or both;
        receiving, from a user, a modification of one or more parameters of the set of parameters from one or more input controls;
        responsive to receiving the one or more modified parameters, executing the at least one trained machine learning model for the particular clinical trial of interest with the modified one or more parameters and receiving as output from the trained machine learning model a modified likelihood that the particular clinical trial associated with the particular drug will result in the particular drug being approved to treat the particular indication; and displaying, to the entity, a measure of the modified likelihood.

2. The system according to claim 1, wherein the instructions are further configured to cause the at least one processor to perform optimizing the at least one trained machine learning model to maximize the likelihood.

3. The system according to claim 2, wherein the instructions are further configured to cause the at least one processor to perform selectively changing one or more parameters of a design of the particular clinical trial to maximize the likelihood.

4. The system according to claim 3, wherein the instructions are further configured to cause the at least one processor to perform modifying at least one of the one or more parameters of the particular clinical trial design including, without limitation, a number of patients in the particular clinical trial, a number of arms of the particular clinical trial, a number of comparators, a number of sites, and/or a number and type of endpoints in the particular clinical trial.

5. The system according to claim 1, wherein the instructions are further configured to cause the at least one processor to perform retrieving data associated with the plurality of drugs and corresponding clinical trials from one or more data sources.

6. The system according to claim 1, wherein the instructions are further configured to cause the at least one processor to perform permitting a user to select at least one user interface control that when selected, causes the interface to modify one or more parameters of the particular clinical trial associated with the particular drug.

7. The system according to claim 1, wherein the instructions are further configured to cause the at least one processor to perform identifying and selecting at least one variable based at least in part on a feature selection algorithm.

8. A method, comprising:
storing, in a database, a plurality of sets of data of clinical trials of a plurality of drugs, wherein data for each of the clinical trials in the plurality of sets of data comprises at least:
a drug of the clinical trial;
an outcome of the clinical trial for the drug;
data regarding patients of the clinical trial used to evaluate the drug; and
at least one of regulatory data associated with the clinical trial, drug molecule characteristics of the drug, and design information of the clinical trial;
training a plurality of different types of machine learning models using training data of clinical trials of the plurality of drugs from the plurality of sets of data to generate a plurality of trained machine learning models, wherein each of the plurality of different types of machine learning models is trained to take as input a drug of interest and an indication of interest and to generate as output a predicted outcome of a new clinical trial for the drug of interest and the indication of interest;
testing the plurality of trained machine learning models, comprising executing each trained machine learning model of the plurality of different types of machine learning models on testing data from the plurality of sets of data of clinical trials of the plurality of drugs to determine a prediction of a particular trial outcome and to generate associated performance data for each machine learning model;
selecting, based on the performance data associated with each trained machine learning model, at least one trained machine learning model and an associated type of machine learning model, comprising comparing the performance data associated with each trained machine learning model using an area under the ROC curve (AUC) metric to select the at least one trained machine learning model as performing better than at least one other model of the trained machine learning models;
executing the at least one trained machine learning model by inputting input data to the trained machine learning model for a particular clinical trial under investigation for an associated particular drug and a particular indication of the particular clinical trial and receiving as output from execution of the at least one trained machine learning model a likelihood that the particular clinical trial associated with the particular drug and the particular indication will result in the particular drug being approved to treat the particular indication;
identifying via an interface to an entity, a measure of the likelihood;
displaying, via the interface, a set of parameters for the particular clinical trial under investigation, wherein:
the set of parameters were used to execute the at least one trained machine learning model for the particular clinical trial under investigation; and
the set of parameters relate to patients of the particular clinical trial, design information of the particular clinical trial, or both;
receiving, from a user, a modification of one or more parameters of the set of parameters from one or more input controls;
responsive to receiving the one or more modified parameters, executing the at least one trained machine learning model for the particular clinical trial of interest with the modified one or more parameters and receiving as output from the trained machine learning model a modified likelihood that the particular clinical trial associated with the particular drug will result in the particular drug being approved to treat the particular indication; and
identifying, to the entity, a measure of the modified likelihood.

9. The method according to claim 8, further comprising maximizing the likelihood using the at least one trained machine learning model.

10. The method according to claim 9, further comprising selectively changing one or more parameters of a design of the particular clinical trial to maximize the likelihood.

11. The method according to claim 10, further comprising modifying at least one of the one or more parameters of the particular clinical trial design including, without limitation, a number of patients in the particular clinical trial, a number of arms of the particular clinical trial, a number of comparators, a number of sites, and/or a number and type of endpoints in the particular clinical trial.

12. The method according to claim 8, further comprising retrieving data associated with the plurality of drugs and corresponding clinical trials from one or more data sources.

13. The method according to claim 8, further comprising permitting a user to select at least one user interface control that when selected, causes the interface to modify one or more parameters of the particular clinical trial associated with the particular drug.

14. The method according to claim 8, further comprising identifying and selecting at least one variable based at least in part on a feature selection algorithm.

15. A non-volatile computer-readable medium encoded with instructions for execution on a computer system, the instructions when executed by at least one processor, cause the at least one processor to perform:

storing, in a database a plurality of sets of data of clinical trials of a plurality of drugs, wherein data for each of the clinical trials in the plurality of sets of data comprises at least:
        a drug of the clinical trial;
        an outcome of the clinical trial for the drug;
        data regarding patients of the clinical trial used to evaluate the drug; and
            at least one of regulatory data associated with the clinical trial, drug molecule characteristics of the drug, and design information of the clinical trial;
    training a plurality of different types of machine learning models using training data of clinical trials of the plurality of drugs from the plurality of sets of data to generate a plurality of trained machine learning models, wherein each of the plurality of different types of machine learning models is trained to take as input a drug of interest and an indication of interest and to generate as output a predicted outcome of a new clinical trial for the drug of interest and the indication of interest;
    testing the plurality of trained machine learning models, comprising executing each trained machine learning model of the plurality of different types of machine learning models on testing data from the plurality of sets of data of clinical trials of the plurality of drugs to determine a prediction of a particular trial outcome and to generate associated performance data for each trained machine learning model;
    selecting, based on the performance data associated with each trained machine learning model, at least one trained machine learning model and an associated type of machine learning model, comprising comparing the performance data associated with each trained machine learning model using an area under the ROC curve (AUC) metric to select the at least one trained machine learning model as performing better than at least one other model of the trained machine learning models;
    executing the at least one trained machine learning model by inputting input data to the trained machine learning model for a particular clinical trial under investigation for an associated particular drug and a particular indication of the particular clinical trial and receiving as output from execution of the at least one trained machine learning model a likelihood that the particular clinical trial associated with the particular drug and the particular indication will result in the particular drug being approved to treat the particular indication;
    identifying via an interface to an entity, a measure of the likelihood;
    displaying, via the interface, a set of parameters for the particular clinical trial under investigation, wherein:
        the set of parameters were used to execute the at least one trained machine learning model for the particular clinical trial under investigation; and
        the set of parameters relate to patients of the particular clinical trial, design information of the particular clinical trial, or both;
    receiving, from a user, a modification of one or more parameters of the set of parameters from one or more input controls;
    responsive to receiving the one or more modified parameters, executing the at least one trained machine learning model for the particular clinical trial of interest with the modified one or more parameters and receiving as output from the trained machine learning model a modified likelihood that the particular clinical trial associated with the particular drug will result in the particular drug being approved to treat the particular indication; and
    identifying, to the entity, a measure of the modified likelihood.

* * * * *

UNITED STATES PATENT AND TRADEMARK OFFICE
CERTIFICATE OF CORRECTION

PATENT NO. : 11,948,667 B2
APPLICATION NO. : 16/793565
DATED : April 2, 2024
INVENTOR(S) : Evangelos Vergetis et al.

It is certified that error appears in the above-identified patent and that said Letters Patent is hereby corrected as shown below:

In the Claims

Claim 1, at Column 20, Line 47, please replace "the likelihoods;" with -- the likelihood; --.

Signed and Sealed this
Tenth Day of December, 2024

Katherine Kelly Vidal
*Director of the United States Patent and Trademark Office*